(12) United States Patent
Young et al.

(10) Patent No.: US 9,732,349 B2
(45) Date of Patent: *Aug. 15, 2017

(54) **IN VIVO UNNATURAL AMINO ACID EXPRESSION IN THE METHYLOTROPHIC YEAST *PICHIA PASTORIS***

(71) Applicant: The Scripps Research Institute, La Jolla, CA (US)

(72) Inventors: Travis Young, San Diego, CA (US); Peter G. Schultz, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/165,199

(22) Filed: Jan. 27, 2014

(65) Prior Publication Data

US 2014/0287464 A1     Sep. 25, 2014

Related U.S. Application Data

(63) Continuation of application No. 12/734,995, filed as application No. PCT/US2008/013568 on Dec. 10, 2008, now Pat. No. 8,647,840.

(60) Provisional application No. 61/007,341, filed on Dec. 11, 2007.

(51) Int. Cl.
| | |
|---|---|
| *C07K 16/00* | (2006.01) |
| *C12N 15/81* | (2006.01) |
| *C12N 9/00* | (2006.01) |
| *C12P 21/02* | (2006.01) |
| *A61K 47/48* | (2006.01) |

(52) U.S. Cl.
CPC ...... *C12N 15/815* (2013.01); *A61K 47/48384* (2013.01); *C12N 9/93* (2013.01); *C12P 21/02* (2013.01); *C07K 2319/00* (2013.01); *C07K 2319/55* (2013.01)

(58) Field of Classification Search
CPC combination set(s) only.
See application file for complete search history.

(56) References Cited

U.S. PATENT DOCUMENTS

| | | |
|---|---|---|
| 6,927,042 B2 | 8/2005 | Schultz et al. |
| 7,045,337 B2 | 5/2006 | Schultz et al. |
| 7,083,970 B2 | 8/2006 | Schultz et al. |
| 7,129,333 B2 | 10/2006 | Schultz et al. |
| 7,183,082 B2 | 2/2007 | Schultz et al. |
| 7,199,222 B2 | 4/2007 | Shultz et al. |
| 7,217,809 B2 | 5/2007 | Schultz et al. |
| 7,238,510 B2 | 7/2007 | Schultz et al. |
| 7,262,040 B2 | 8/2007 | Schultz et al. |
| 7,385,028 B2 | 6/2008 | Miao et al. |
| 8,957,187 B2 | 2/2015 | Sidhu et al. |
| 2004/0198637 A1 | 10/2004 | Schultz et al. |
| 2004/0265952 A1 | 12/2004 | Deiters et al. |
| 2005/0009049 A1 | 1/2005 | Chin et al. |
| 2005/0136513 A1 | 6/2005 | Zhang et al. |
| 2005/0208536 A1 | 9/2005 | Schultz et al. |
| 2005/0227318 A1 | 10/2005 | Alfonta et al. |
| 2005/0250183 A1 | 11/2005 | Schultz et al. |
| 2005/0272121 A1 | 12/2005 | Xie et al. |
| 2006/0063244 A1 | 3/2006 | Schultz et al. |
| 2006/0073507 A1 | 4/2006 | Deiters et al. |
| 2006/0110784 A1 | 5/2006 | Deiters et al. |
| 2006/0110796 A1 | 5/2006 | Schultz et al. |
| 2006/0134746 A1 | 6/2006 | Deiters et al. |
| 2006/0160175 A1 | 7/2006 | Anderson et al. |
| 2006/0177900 A1 | 8/2006 | Anderson et al. |
| 2006/0217532 A1 | 9/2006 | Miao et al. |
| 2006/0246509 A1 | 11/2006 | Deiters et al. |
| 2007/0009990 A1 | 1/2007 | Alfonta et al. |
| 2007/0020634 A1 | 1/2007 | Anderson et al. |
| 2007/0042461 A1 | 2/2007 | Anderson et al. |
| 2007/0111193 A1 | 5/2007 | Zhang et al. |
| 2007/0117184 A1 | 5/2007 | Schultz et al. |
| 2007/0154952 A1 | 7/2007 | Chin et al. |
| 2007/0160598 A1 | 7/2007 | Dennis et al. |
| 2007/0166791 A1 | 7/2007 | Chin et al. |
| 2007/0172915 A1 | 7/2007 | Schultz et al. |
| 2007/0178448 A1 | 8/2007 | Tsao et al. |
| 2007/0184517 A1 | 8/2007 | Schultz et al. |
| 2007/0202552 A1 | 8/2007 | Sidhu et al. |
| 2007/0238152 A1 | 10/2007 | Wang et al. |
| 2007/0281335 A1 | 12/2007 | Ryu et al. |
| 2008/0102124 A1 | 5/2008 | Cho et al. |
| 2010/0297693 A1 | 11/2010 | Young et al. |

FOREIGN PATENT DOCUMENTS

| | | |
|---|---|---|
| JP | 2011-527886 A | 11/2011 |
| WO | WO 02/085923 A2 | 10/2002 |
| WO | WO 2004/094503 A1 | 11/2004 |
| WO | WO 2004/094593 A2 | 11/2004 |
| WO | WO 2006/068802 A2 | 6/2006 |
| WO | WO 2007/136778 A2 | 11/2007 |
| WO | WO 2008/066583 A2 | 6/2008 |
| WO | WO 2008/137471 A2 | 11/2008 |
| WO | WO 2009/075847 A2 | 6/2009 |

OTHER PUBLICATIONS

Montigny, et al. (2000) "Genomic Exploration of the Hemlascomycetous Yeasts: 15. *Pichia sorbltophllla.*" *FEBS Letters*, 487(1):87-90.
Clare, et al. (1991) "High-level expression of tetanus toxin fragment C in Pichia pastoris strains containing multiple tandem integrations of the gene." *Biotechnology*, 9(5):455-460.
Office Action dated Jul. 8, 2014 for related Japanese application No. 2010-537955 (corresponding to international application No. PCT/US2008/013568).

(Continued)

*Primary Examiner* — Kagnew H Gebreyesus
(74) *Attorney, Agent, or Firm* — Quine Intellectual Property Law Group, P.C.

(57) ABSTRACT

The invention provides orthogonal translation systems for the production of polypeptides comprising unnatural amino acids in methylotrophic yeast such as *Pichia pastoris*. Methods for producing polypeptides comprising unnatural amino acids in methylotrophic yeast such as *Pichia pastoris* are also provided.

14 Claims, 17 Drawing Sheets

(56) References Cited

OTHER PUBLICATIONS

Office Action dated Jun. 20, 2014 for related Indian application No. 4071/CHENP/2010 (corresponding to international application No. PCT/US2008/013568).
Cregg, et al. (2000) "Recombinant Protein Expression in *Pichia pastoris.*" *Mol. Biotechnol.*, 16:23-52.
Office Action dated Nov. 15, 2014, from related Chinese Patent Application No. 200980156791.4.
U.S. Appl. No. 12/316,370, filed Dec. 10, 2008 by Young et al.
U.S. Appl. No. 12/653,274, filed Dec. 9, 2009 by Young et al.
U.S. Appl. No. 13/133,629, filed Dec. 9, 2009 by Young et al.
U.S. Appl. No. 12/734,995, filed Jun. 8, 2010 by Young et al.
U.S. Appl. No. 14/065,111, filed Oct. 28, 2013 by Young et al.
Buckholz and Gleeson (1991) "Yeast systems for the commercial production of heterologous proteins." *Biotechnology*, 9(11): 1067-1072.
Cereghino and Cregg (2000) "Heterologous protein expression in the methylotrophic yeast *Pichia pastoris.*" *FEMS Microbiology Reviews*, 24(1): 45-66.
Cereghino et al. (2001) "Expression of Foreign Genes in the yeast *Pichia pastoris.*" *Genetic Engineering*, 23: 157-169.
Chen et al. (2007)"An Improved System for the Generation and Analysis of Mutant Proteins Containing Unnatural Amino Acids in *Saccharomyces cerevisiae.*" *Journal of Molecular Biology*, 371(1): 112-122.
Chin et al. (2002) "Addition of p-Azido-L-phenylalanine to the Genetic Code of *Escherichia coli.*" *Journal of the American Chemistry Society*, 124: 9026-9027.
Chin et al. (2003) "An Expanded Eukaryotic Genetic Code." *Science*, 301(5635): 964-967.
Cos et al. (2006) "Operational strategies, monitoring and control of heterologous protein production in the methylotropic yeast *Pichia pastoris* under different promoters: A review." 5(17): 1-20.
Daly (2004) "Expression of heterologous proteins in *Pichia pastoris*: a useful experimental tool in protein engineering and production" *Journal of Molecular Recognition*, 18: 119-138.
De Montigny et al. (2000) "Genomic Exploration of the Hemiascomycetous Yeasts: 15. *Pichia sorbitophila.*" *FEBS Letters*, 487: 87-90.
Deiters et al. (2003) "Adding amino acids with novel reactivity to the genetic code of *Saccharomyces cerevisiae.*" *Journal of the American Chemistry Society*, 125(39): 11782-11783.
Dirksen et al. (2006) "Nucleophilic Catalysis of Oxime Ligation." *Angewandte Chemie International Eddition English*, 45(45): 7581-7584.
European Search Repot, dated Apr. 19, 2011 from EP application No. 08860799.9.
Hani and Feldmann (1998) "tRNA genes and retoelements in the yeast genome." *Nucleic Acids Research*, 26(3): 689-696.
Hendrickson et al. (2004) "Incorporation of Nonnatural Amino Acids Into Proteins." *Annual Review of Biochemistry*, 73: 147-176.
Higgins (1995) "Overview of Protein Expression in Pichia pastoris." *Current Protocols in Protein Science*, 5.7.1-5.7.18, Supplemental 2 Unit.
Invitrogen (2009) "Multi-Copy Pichia Expression Kit," User Manual for the Isolation and Expression of Recombinant Proteins from Pichia pastoris Strains Containing Multiple Copies of a Particular Gene by Invitrogen Life Technologies.
Kim et al. (2003) "Development and Characterization of a Glucagon-Like Peptide 1-Albumin Conjugate." *Diabetes*, 52: 751-759.

Kratz (2008) "Albumim as a drug carrier: Design of prodrugs, drug conjugates and nanoparticles." *Journal of Controlled Release*, 132: 171-183.
Kupcsulik and Sevella (2005) "Optimization of Specific Product Formation Rate by Statistical and Formal Kinetic Model Descriptions of an HAS Producing Pichia pastoris $Mut^s$ Strain." *Chemical and Biochemical Engineering Quarterly*, 19(1): 99-108.
Lemke et al. (2007) "Control of protein phosphorylation with a genetically encoded photocaged amino acid." *Nature Chemical Biology*, 3(12): 769-772.
Li et al. (2006) "Optimization of humanized IgGs in glycoengineered Pichia pastoris." *Nature Biotechnology*, 24: 210-215.
Neundorf et al. (2008) "Detailed Analysis Concerning the Biodistribution and Metabolism of Human Calcitonin-Derived Cell-Penetrating Peptides." *Bioconjugate Chemistry*, 19: 1596-1603.
Ohya et al. (2005) "Optimization of human serum albumin production in methylotropic yeast *Pichia pastoris* by repeated fed-batch fermentation." *Biotechnology and Bioengineering*. 90(7): 876-887.
Pastrnak et al. (2000) "A new orthogonal suppressor tRNA/Amino-acyl-tRNA synthetase pair for evolving an organism with an expanded genetic code." *Helvetica Chimica Acta* 83: 2277-2286.
Sakamoto et al. (2002) Site-specific incorporation of an unnatural amino acid into proteins in mammalian cells. *Nucl. Acids Res.* 30(21): 4692-4699.
Shen et al. (1998) "A strong nitrogen sourse-regulated prompter for controlled expression of forein genes in the yeast *Pichia pastois.*" *Gene*, 216(1): 93-102.
Sreekirshna et al. (1989) "High-level expression, purification, and characterization of recombinant human tumor recrosis factor synthesized in the methylotropic yease *Pichia pastoris.*" *Biochemistry* 28(9): 4117-4125.
Strable et al. (2008) "Unnatural Amino Acid Incorporation into Virus-Like Particles." *Bioconjugate Chemistry*, 19: 866-875.
Summerer et al. (2006) "A Genetically Encoded Fluorescent Amino Acid." *Proceedings of the National Academy of Sciences*, USA, 103(26): 9785-9789.
Veronese and Pasut (2005) "PEGylation, successful approach to drug delivery." *Drug Discovery Today*, 10(21): 1451-1458.
Wang and Wang (2008) "New methods enabiling efficient incorporation of unnatural amino acids in yeast." *Journal of the American Chemistry Society*, 130(19): 6066-6067.
Wang et al. (2002) "Addition of the keto functiona; group to the genetic code of Escheri." *Proceedings of the National Academy of Sciences*, USA, 100(1): 56-61.
Wang et al. (2007) Evolved orthogonal ribosomes enhance the efficiency of synthetic genetic code. *Nat. Biotechnol.* 25(17): 770-777.
Xie and Schultz (2005) "Adding amino acids to the genetic repertoire." *Current Opinion in Chemical Biology*, 9: 548-55.
Young et al. (2009) "Expanding the Genetic Repertoire of the Methylotrophic Yease *Pichia pastoris* dagger." *Biochemistry*, 48(12): 2643-2653.
Japanese office action dated Apr. 14, 2015, for related application No. JP 2010-537955.
Crane and Gould (1994) "The Pichia pastoris HIS4 gene: nucleotide sequence, creation of a non-reverting his4 deletion mutant, and development of HIS4-based replicating and integrating plasmids."*Curr Genet.*, 26(5-6): 443-450.
Resina, et al. (2005) "Developing high cell density fed-batch cultivation strategies for heterologous protein production in Pichia pastoris using the nitrogen source-regulated FLD1 Promoter." *Biotechnol Bioeng.*, 91(6): 760-767.
Office Action dated Dec. 1, 2015 in related European Application No. EP08860799.9.

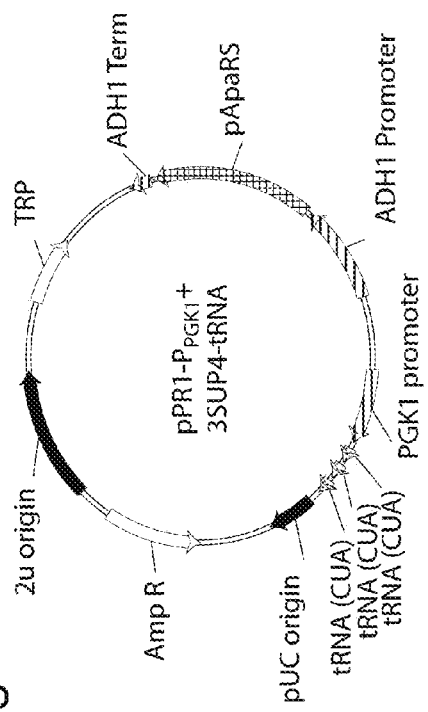
Fig. 6A
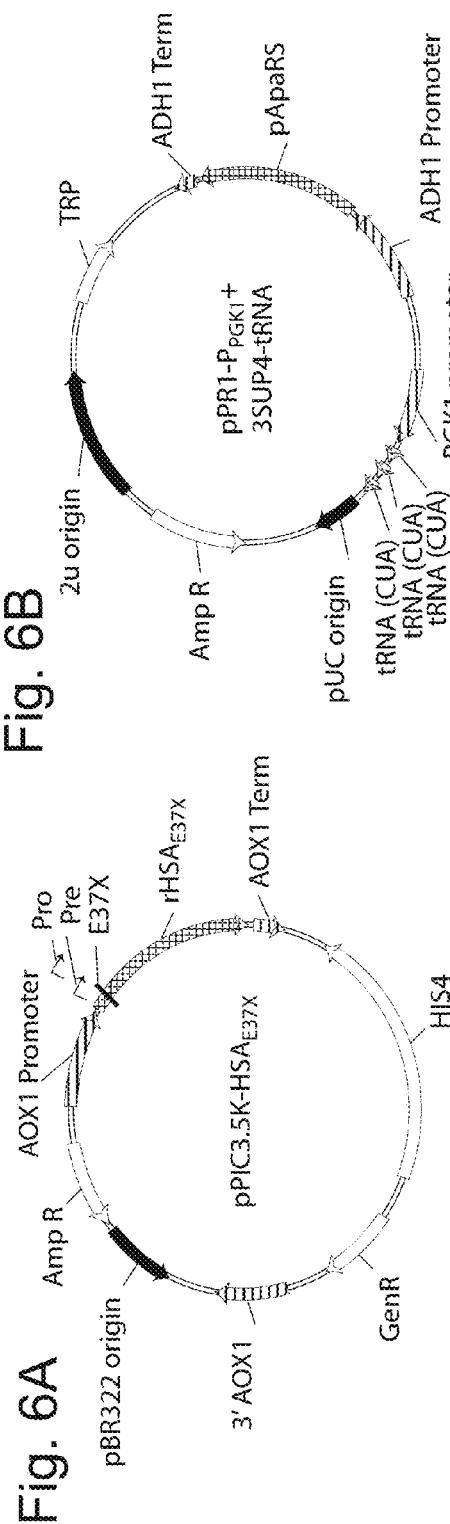
Fig. 6B
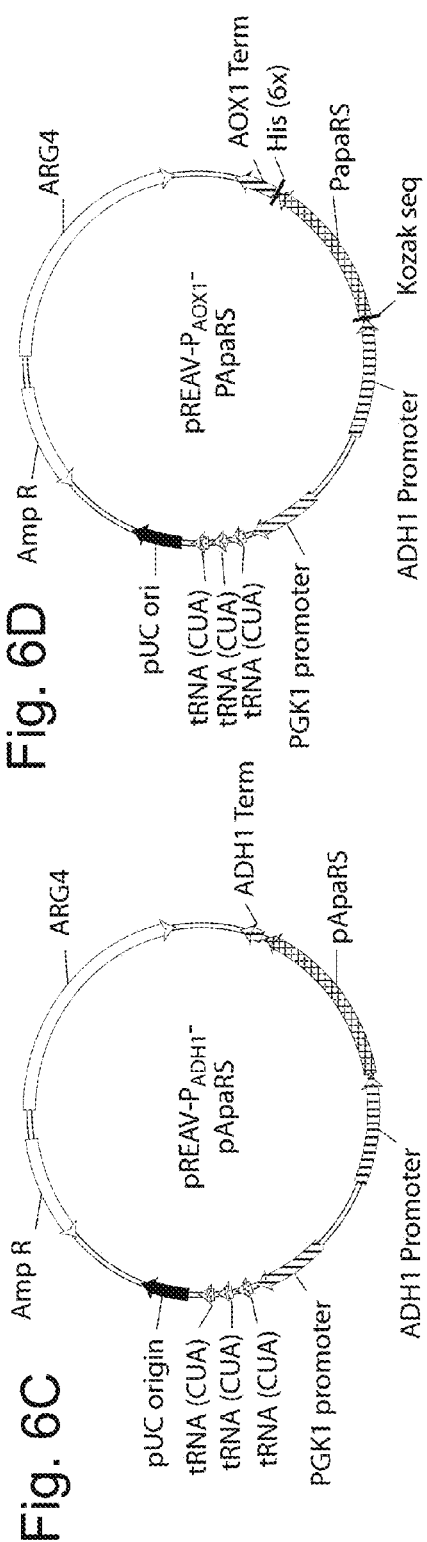
Fig. 6C
Fig. 6D
Fig. 6E mkwvtfisllflfssaysrgvfrrdahksevahrfkdlgeenfkalviafaqylqqcpfxdhvk···

SEQUENCE LISTING

<160> NUMBER OF SEQ ID NOS: 44

<210> SEQ ID NO 1
<211> LENGTH: 21
<212> TYPE: PRT
<213> ORGANISM: Artificial Sequence
<220> FEATURE:
<223> OTHER INFORMATION: Peptide derived from HSA
<220> FEATURE:
<221> NAME/KEY: X
<222> LOCATION: (17)..(17)
<223> OTHER INFORMATION: Xaa = p-azidophenylalanine

<400> SEQUENCE: 1

Ala Leu Val Leu Ile Ala Phe Ala Gln Tyr Leu Gln Gln Cys Pro Phe
1               5                   10                  15

Xaa Asp His Val Lys
            20

<210> SEQ ID NO 2
<211> LENGTH: 38
<212> TYPE: DNA
<213> ORGANISM: Artificial Sequence
<220> FEATURE:
<223> OTHER INFORMATION: Oligonucleotide

<400> SEQUENCE: 2
gacagacctt accaaagtcc acacggaatg ctgccatg                            38

<210> SEQ ID NO 3
<211> LENGTH: 48
<212> TYPE: DNA
<213> ORGANISM: Artificial Sequence
<220> FEATURE:
<223> OTHER INFORMATION: Oligonucleotide

<400> SEQUENCE: 3
ggtaaggtct gtcactaact tggaaacttc tgcaaactca gctttggg                 48

<210> SEQ ID NO 4
<211> LENGTH: 37
<212> TYPE: DNA
<213> ORGANISM: Artificial Sequence
<220> FEATURE:
<223> OTHER INFORMATION: Oligonucleotide

<400> SEQUENCE: 4
catggagacc tgcttgaatg tgctgatgac agggcgg                             37

<210> SEQ ID NO 5
<211> LENGTH: 34
<212> TYPE: DNA
<213> ORGANISM: Artificial Sequence
<220> FEATURE:
<223> OTHER INFORMATION: Oligonucleotide

<400> SEQUENCE: 5
caagcaggtc tccatggcag cattccgtgt ggac                                34

<210> SEQ ID NO 6
<211> LENGTH: 46
<212> TYPE: DNA
<213> ORGANISM: Artificial Sequence
<220> FEATURE:
<223> OTHER INFORMATION: Oligonucleotide

<400> SEQUENCE: 6
gattgccttt gctcagtatc ttcagcagtg tccattttag gatcat             46

<210> SEQ ID NO 7
<211> LENGTH: 53
<212> TYPE: DNA
<213> ORGANISM: Artificial Sequence
<220> FEATURE:
<223> OTHER INFORMATION: Oligonucleotide

<400> SEQUENCE: 7
gtttttgcaa attcagttac ttcattcact aattttacat gatcctaaaa tgg       53

<210> SEQ ID NO 8
<211> LENGTH: 51
<212> TYPE: DNA
<213> ORGANISM: Artificial Sequence
<220> FEATURE:
<223> OTHER INFORMATION: Oligonucleotide

<400> SEQUENCE: 8
atccgaggat ccaaacgatg aagtgggtaa cctttatttc ccttctttt c         51

<210> SEQ ID NO 9
<211> LENGTH: 43
<212> TYPE: DNA
<213> ORGANISM: Artificial Sequence
<220> FEATURE:
<223> OTHER INFORMATION: Oligonucleotide

<400> SEQUENCE: 9
gctaacgaat tcattataag cctaaggcag cttgacttgc agc                 43

<210> SEQ ID NO 10
<211> LENGTH: 48
<212> TYPE: DNA
<213> ORGANISM: Artificial Sequence
<220> FEATURE:
<223> OTHER INFORMATION: Oligonucleotide

<400> SEQUENCE: 10
taccactaga agcttggaga aaataccgca tcaggaaatt gtaaacgt            48

<210> SEQ ID NO 11
<211> LENGTH: 49
<212> TYPE: DNA
<213> ORGANISM: Artificial Sequence
<220> FEATURE:
<223> OTHER INFORMATION: Oligonucleotide

<400> SEQUENCE: 11
gtgagggcag gtaccgttct gtaaaaatgc agctcagatt ctttgtttg           49

<210> SEQ ID NO 12
<211> LENGTH: 33
<212> TYPE: DNA
<213> ORGANISM: Artificial Sequence
<220> FEATURE:
<223> OTHER INFORMATION: Oligonucleotide

<400> SEQUENCE: 12
aaatatggta cctgccctca cggtggttac ggt                            33

```
<210> SEQ ID NO 13
<211> LENGTH: 41
<212> TYPE: DNA
<213> ORGANISM: Artificial Sequence
<220> FEATURE:
<223> OTHER INFORMATION: Oligonucleotide

<400> SEQUENCE: 13
catttcaagc ttctagtggt aggaattctg taccggttta c                              41

<210> SEQ ID NO 14
<211> LENGTH: 46
<212> TYPE: DNA
<213> ORGANISM: Artificial Sequence
<220> FEATURE:
<223> OTHER INFORMATION: Oligonucleotide

<400> SEQUENCE: 14
ttctgagaat tcaccatggc aagcagtaac ttgattaaac aattgc                         46

<210> SEQ ID NO 15
<211> LENGTH: 66
<212> TYPE: DNA
<213> ORGANISM: Artificial Sequence
<220> FEATURE:
<223> OTHER INFORMATION: Oligonucleotide

<400> SEQUENCE: 15
taggctcggc cgcttagtgg tggtggtggt ggtgtttcca gcaaatcaga cagtaattct          60
ttttac                                                                     66

<210> SEQ ID NO 16
<211> LENGTH: 42
<212> TYPE: DNA
<213> ORGANISM: Artificial Sequence
<220> FEATURE:
<223> OTHER INFORMATION: Oligonucleotide

<400> SEQUENCE: 16
atcgtactta aggaaagcgt actcaaacag acaaccattt cc                             42

<210> SEQ ID NO 17
<211> LENGTH: 36
<212> TYPE: DNA
<213> ORGANISM: Artificial Sequence
<220> FEATURE:
<223> OTHER INFORMATION: Oligonucleotide

<400> SEQUENCE: 17
ttctcaggcg cgccatcgcc cttcccaaca gttgcg                                    36

<210> SEQ ID NO 18
<211> LENGTH: 48
<212> TYPE: DNA
<213> ORGANISM: Artificial Sequence
<220> FEATURE:
<223> OTHER INFORMATION: Oligonucleotide

<400> SEQUENCE: 18
atcgtactta agagatctaa catccaaaga cgaaaggttg aatgaaac                       48

<210> SEQ ID NO 19
<211> LENGTH: 48
<212> TYPE: DNA
<213> ORGANISM: Artificial Sequence
```

```
<220> FEATURE:
<223> OTHER INFORMATION: Oligonucleotide

<400> SEQUENCE: 19
tgcacaggcg cgccaagctt gcacaaacga acttctcact taatcttc        48

<210> SEQ ID NO 20
<211> LENGTH: 33
<212> TYPE: DNA
<213> ORGANISM: Artificial Sequence
<220> FEATURE:
<223> OTHER INFORMATION: Oligonucleotide biotinylated at 5' end

<400> SEQUENCE: 20
catttcaaga ctgtcgcctt aaccactcgg cca                         33

<210> SEQ ID NO 21
<211> LENGTH: 34
<212> TYPE: DNA
<213> ORGANISM: Artificial Sequence
<220> FEATURE:
<223> OTHER INFORMATION: Oligonucleotide biotinylated at 5' end

<400> SEQUENCE: 21
gaaccagcgc gggcagagcc caacacattt caag                        34

<210> SEQ ID NO 22
<211> LENGTH: 34
<212> TYPE: DNA
<213> ORGANISM: Artificial Sequence
<220> FEATURE:
<223> OTHER INFORMATION: Oligonucleotide biotinylated at 5' end

<400> SEQUENCE: 22
ctgcatcctt cgccttaacc actcggccat cgta                        34

<210> SEQ ID NO 23
<211> LENGTH: 34
<212> TYPE: DNA
<213> ORGANISM: Artificial Sequence
<220> FEATURE:
<223> OTHER INFORMATION: Oligonucleotide biotinylated at 5' end

<400> SEQUENCE: 23
acacgagcag ggttcgaacc tgcgcgggca gagc                        34

<210> SEQ ID NO 24
<211> LENGTH: 32
<212> TYPE: DNA
<213> ORGANISM: Artificial Sequence
<220> FEATURE:
<223> OTHER INFORMATION: Oligonucleotide biotinylated at 5' end

<400> SEQUENCE: 24
ggaaggattc gaaccttcga agtcgatgac gg                          32

<210> SEQ ID NO 25
<211> LENGTH: 32
<212> TYPE: DNA
<213> ORGANISM: Artificial Sequence
<220> FEATURE:
<223> OTHER INFORMATION: Oligonucleotide biotinylated at 5' end

<400> SEQUENCE: 25
tctgctccct ttggccgctc gggaacccca cc                          32
```

-continued

```
<210> SEQ ID NO 26
<211> LENGTH: 49
<212> TYPE: DNA
<213> ORGANISM: Artificial Sequence
<220> FEATURE:
<223> OTHER INFORMATION: Oligonucleotide

<400> SEQUENCE: 26
gtatcgctta agtccaagat aggctatttt tgtcgcataa attttgtc        49

<210> SEQ ID NO 27
<211> LENGTH: 51
<212> TYPE: DNA
<213> ORGANISM: Artificial Sequence
<220> FEATURE:
<223> OTHER INFORMATION: Oligonucleotide

<400> SEQUENCE: 27
cgttagccat ggttttctca gttgatttgt ttgtgggat ttagtaagtc g      51

<210> SEQ ID NO 28
<211> LENGTH: 47
<212> TYPE: DNA
<213> ORGANISM: Artificial Sequence
<220> FEATURE:
<223> OTHER INFORMATION: Oligonucleotide

<400> SEQUENCE: 28
gtatcgctta agcatatgat gagtcacaat ctgcttccac agacgag           47

<210> SEQ ID NO 29
<211> LENGTH: 49
<212> TYPE: DNA
<213> ORGANISM: Artificial Sequence
<220> FEATURE:
<223> OTHER INFORMATION: Oligonculeotide

<400> SEQUENCE: 29
cgttagccat gggactgcta ttatctctgt gtgtatgtgt gtattgggc         49

<210> SEQ ID NO 30
<211> LENGTH: 45
<212> TYPE: DNA
<213> ORGANISM: Artificial Sequence
<220> FEATURE:
<223> OTHER INFORMATION: Oligonucleotide

<400> SEQUENCE: 30
gtatcgctta aggaattcgg acaaatgtgc tgttccggta gcttg             45

<210> SEQ ID NO 31
<211> LENGTH: 50
<212> TYPE: DNA
<213> ORGANISM: Artificial Sequence
<220> FEATURE:
<223> OTHER INFORMATION: Oligonucleotide

<400> SEQUENCE: 31
cgttagccat ggtcttgata tacttgatac tgtgttcttt gaattgaaag        50

<210> SEQ ID NO 32
<211> LENGTH: 44
<212> TYPE: DNA
<213> ORGANISM: Artificial Sequence
<220> FEATURE:
<223> OTHER INFORMATION: Oligonucleotide
```

<400> SEQUENCE: 32
gtatcgctta aggcatgcag gaatctctgg cacggtgcta atgg                44

<210> SEQ ID NO 33
<211> LENGTH: 49
<212> TYPE: DNA
<213> ORGANISM: Artificial Sequence
<220> FEATURE:
<223> OTHER INFORMATION: Oligonucleotide

<400> SEQUENCE: 33
cgttagccat ggtgtgaata tcaagaattg tatgaacaag caaagttgg             49

<210> SEQ ID NO 34
<211> LENGTH: 49
<212> TYPE: DNA
<213> ORGANISM: Artificial Sequence
<220> FEATURE:
<223> OTHER INFORMATION: Oligonucleotide

<400> SEQUENCE: 34
gtatcgctta agggatcctt ttttgtagaa atgtcttggt gtcctcgtc             49

<210> SEQ ID NO 35
<211> LENGTH: 50
<212> TYPE: DNA
<213> ORGANISM: Artificial Sequence
<220> FEATURE:
<223> OTHER INFORMATION: Oligonucleotide

<400> SEQUENCE: 35
cgttagccat ggtgtgtttt gatagttgtt caattgattg aaatagggac            50

<210> SEQ ID NO 36
<211> LENGTH: 22
<212> TYPE: DNA
<213> ORGANISM: Artificial Sequence
<220> FEATURE:
<223> OTHER INFORMATION: Oligonucleotide with biotinylated 5' end

<400> SEQUENCE: 36
tgagacgctg cttaaccgct tc                                         22

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide with biotinylated 5' end

<400> SEQUENCE: 37
taaagaagta ttcaggatcg gactg                                      25

<210> SEQ ID NO 38
<211> LENGTH: 34
<212> TYPE: DNA
<213> ORGANISM: Artificial Sequence
<220> FEATURE:
<223> OTHER INFORMATION: Oligonucleotide

<400> SEQUENCE: 38
aaggaagcta gcctcttttt caattgtata tgtg                            34

-continued

```
<210> SEQ ID NO 39
<211> LENGTH: 37
<212> TYPE: DNA
<213> ORGANISM: Artificial Sequence
<220> FEATURE:
<223> OTHER INFORMATION: Oligonucleotide

<400> SEQUENCE: 39
cgtacacgcg tctgtacaga aaaaaagaa aaatttg                              37

<210> SEQ ID NO 40
<211> LENGTH: 36
<212> TYPE: DNA
<213> ORGANISM: Artificial Sequence
<220> FEATURE:
<223> OTHER INFORMATION: Oligonucleotide

<400> SEQUENCE: 40
attcacacca tggaagagca ataccgcccg gaagag                              36

<210> SEQ ID NO 41
<211> LENGTH: 47
<212> TYPE: DNA
<213> ORGANISM: Artificial Sequence
<220> FEATURE:
<223> OTHER INFORMATION: Oligonucleotide

<400> SEQUENCE: 41
ttaattcgcg gccgcttagc caacgaccag attgaggagt ttacctg                  47

<210> SEQ ID NO 42
<211> LENGTH: 13
<212> TYPE: PRT
<213> ORGANISM: Artificial Sequence
<220> FEATURE:
<223> OTHER INFORMATION: Chymotryptic peptide of HSA
<220> FEATURE:
<221> NAME/KEY: X
<222> LOCATION: (1)..(1)
<223> OTHER INFORMATION: Xaa = DMNB-C (e.g., cysteine analog of
      DMNB-serine)

<400> SEQUENCE: 42

Xaa Asp His Val Lys Leu Val Asn Glu Val Thr Glu Phe
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Chymotryptoc peptide of HSA
<220> FEATURE:
<221> NAME/KEY: X
<222> LOCATION: (1)..(1)
<223> OTHER INFORMATION: Xaa = isoleucine or leucine

<400> SEQUENCE: 43

Xaa Asp His Val Lys Leu Val Asn Glu Val Thr Glu Phe
1               5                   10

<210> SEQ ID NO 44
<211> LENGTH: 64
<212> TYPE: PRT
<213> ORGANISM: Artificial Sequence
<220> FEATURE:
<223> OTHER INFORMATION: Partial sequence of HSA
```

```
<220> FEATURE:
<221> NAME/KEY: X
<222> LOCATION: (60)..(60)
<223> OTHER INFORMATION: Xaa = p-benzoylphenylalanine,
    p-azidophenylalanine, p-(propargyloxy)phenylalanine,
    p-methoxyphenylalanine, p-iodophenylalanine, 4,5-dimethoxy-2-
    nitrobenzylserine, 2-amino-3-(5-(dimethylamino)naphthalene-
    1sulfonamde)propanoic

<400> SEQUENCE: 44

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Asn Asn Phe Lys Ala Leu Val Ile
        35                  40                  45

Ala Phe Ala Gln Tyr Leu Gln Gln Cys Pro Phe Xaa Asp His Val Lys
    50                  55                  60
```

IN VIVO UNNATURAL AMINO ACID EXPRESSION IN THE METHYLOTROPHIC YEAST PICHIA PASTORIS

CROSS-REFERENCE TO RELATED APPLICATIONS

This application is a continuation of U.S. Ser. No. 12/734,995, filed on Sep. 2, 2010, now allowed, which is a 371 application of PCT/US2008/013568, entitled "IN VIVO UNNATURAL AMINO ACID EXPRESSION IN THE METHYLOTROPHIC YEAST *PICHIA PASTORIS*" by Travis Young et al., filed on Dec. 10, 2008, which claims priority to and benefit of U.S. Provisional Patent Application Ser. No. 61/007,341, entitled "IN VIVO UNNATURAL AMINO ACID EXPRESSION IN THE METHYLOTROPHIC YEAST *PICHIA PASTORIS*" by Travis Young et al., filed Dec. 11, 2007, the contents of which are incorporated herein by reference in their entirety for all purposes.

STATEMENT AS TO RIGHTS TO INVENTIONS MADE UNDER FEDERALLY SPONSORED RESEARCH AND DEVELOPMENT

The invention was made with government support under grant number GM062159 awarded by the National Institutes of Health and under DE-FG03-00ER46051 awarded by the United States Department of Energy. The government has certain rights in this invention.

FIELD OF THE INVENTION

This invention relates to the field of protein chemistry, e.g., translation biochemistry. The invention relates to compositions and methods for producing polypeptides comprising unnatural amino acids in methylotrophic yeast such as *Pichia pastoris*.

BACKGROUND OF THE INVENTION

Unnatural amino acids can be site-specifically incorporated into polypeptides with high efficiency and high fidelity by means of heterologous orthogonal tRNA/aminoacyl-tRNA synthetase pairs (O-tRNA/O-RS pairs) (Deiters, et al. (2003) "Adding Amino Acids with Novel Reactivity to the Genetic Code of *Saccharomyces cerevisiae*." *J Am Chem Soc* 125: 11782-11783; Wang, et al. (2001) "Expanding the Genetic code of *Escherichia coli*." *Science* 292: 498-500; Chin, et al. (2003) "An Expanded Eukaryotic Genetic Code." *Science* 301: 964-7). These O-tRNA/O-RS pairs recognize their cognate unnatural amino acids but do not significantly cross-react with the tRNAs, aminoacyl tRNA synthetases or amino acids that are endogenous to the system in which they are being used. To date, this technology has permitted the genetically encoded incorporation of more than 30 different unnatural amino acids with unique steric and/or chemical properties into proteins synthesized in *Escherichia coli, Saccharomyces cerevisiae*, and mammalian cells (Xie, J, et al. (2006) "A chemical toolkit for proteins—an expanded genetic code." *Nature Rev Mol Cell Biol* 7:775-782; Wang, L, et al. (2005) "Expanding the genetic code." *Agnew Chem Int Edit* 44: 34-66, Liu, et al. (2007) "Genetic incorporation of unnatural amino acids into proteins in mammalian cells." *Nature Methods* 4: 239-244). This methodology can be particularly useful in the development and large-scale production of therapeutic proteins with enhanced biological properties, reduced toxicities, and/or increased half-lives.

*E. coli* and *S. cerevisiae* expression systems are widely used to synthesize heterologous proteins and can be adapted for large-scale synthesis of proteins comprising unnatural amino acids (Adding Amino Acids with Novel Reactivity to the Genetic Code of *Saccharomyces Cerevisiae*." *J Am Chem Soc* 125: 11782-11783; Wang, et al. (2001) "Expanding the Genetic code of *Escherichia coli*." *Science* 292: 498-500). However, neither of these expression systems is well suited for the production of recombinant mammalian proteins, which often require sulfation, glycosylation or post-translational modifications in order to exhibit a desired biological activity. Furthermore, neither of these hosts is optimal for the production of therapeutic proteins: Proteins produced in *E. coli* usually contain high concentrations of pyrogenic compounds, e.g., endotoxin, and proteins synthesized in *S. cerevisiae* can contain potentially antigenic α1,3 glycan linkages.

In contrast, methylotrophic yeast, such as *Pichia pastoris*, have been identified as attractive candidates for use as recombinant expression systems for heterologous proteins (Lin-Cereghino, et al. (2000) "Heterologous protein expression in the methylotrophic yeast *Pichia pastoris*." *FEMS Microbiol Rev* 24: 45-66). The eukaryotic subcellular organization of methylotrophic yeast enables them to carry out many of the posttranslational folding, processing and modification events required to synthesize biologically active mammalian proteins. Unlike proteins expressed in *S. cerevisiae*, proteins produced by methylotrophic yeast such as *P. pastoris* are less likely to contain high-mannose glycan structures that can hamper downstream processing of heterologously expressed glycoproteins. In addition, proteins synthesized in methylotrophic yeast are free of pyrogenic and antigenic compounds.

Methylotrophic yeast expression systems are particularly useful for large-scale protein synthesis. For example, the yeast *P. pastoris* enables expression of recombinant proteins at levels 10- to 100-fold higher than in *S. cerevisiae*, bacterial, insect, or mammalian systems. In addition, methylotrophs such as *P. pastoris* can be easily cultured in a simple, defined salt medium, eliminating the need for the expensive media supplements and equipment that are required for baculovirus expression systems or mammalian tissue culture. Furthermore, *P. pastoris* is amenable to genetic manipulation, and many molecular microbiological techniques that have been developed for use with *S. cerevisiae* can be adapted for use in *P. pastoris*.

What is needed in the art are new strategies for the site-specific incorporation of unnatural amino acids into proteins in a low-cost expression system that is capable of producing biologically active heterologous proteins that comprise complex posttranslational modifications. There is a need in the art for the development of O-tRNA/O-RS pairs and expression systems that function to incorporate unnatural amino acids into polypeptides synthesized in methylotrophic yeast. The invention described herein fulfills these and other needs, as will be apparent upon review of the following disclosure.

SUMMARY OF THE INVENTION

The incorporation of unnatural amino acids with unique functional groups into proteins in a site-specific manner has made it possible to generate proteins that exhibit enhanced or novel steric, chemical, or biological properties. Such proteins can find therapeutic or pharmaceutical use, and would be beneficially produced in a low-cost expression system that is capable of producing biologically active heterologous proteins that comprise complex posttranslational modifications. The present invention provides methods and compositions that are useful for the site-specific incorporation of unnatural amino acids into proteins in methylotrophic yeast, e.g., *Pichia pastoris*, expression systems.

In one aspect, the invention provides compositions for the incorporation of unnatural amino acids into polypeptides synthesized in methylotrophic yeast, e.g., *Pichia pastoris*. The compositions comprise a methylotrophic yeast cell which includes an unnatural amino acid, an orthogonal aminoacyl-tRNA synthetase (O-RS), wherein the O-RS preferentially aminoacylates an orthogonal tRNA (O-tRNA) with the unnatural amino acid in the methylotrophic yeast cell, and an orthogonal tRNA(O-tRNA), wherein the O-tRNA recognizes a selector codon and is preferentially aminoacylated with the unnatural amino acid by the O-RS in the methylotrophic yeast cell. The methylotrophic yeast cell can be, e.g., a *Candida* cell, a *Hansenula* cell, a *Torulopsis* cell, or a *Pichia* cell, e.g., a *Pichia pastoris* cell. The methylotrophic yeast cell can optionally comprise, e.g., any of the unnatural amino acids as described herein.

The O-RS and the O-tRNA of the cell can optionally be expressed from nucleic acids integrated into the genome. For example, a nucleic acid comprising a polynucleotide encoding the O-RS can optionally be integrated, e.g., at a locus encoding an ARG4 gene, an ADE1 gene, a HIS4 gene, a URA3 gene, an AOX1 gene, an AOX2 gene, or a MET2 gene, as can a nucleic acid encoding or comprising the O-tRNA. Optionally, the O-RS can be expressed from an inducible promoter, e.g., an AOX1 promoter, an AOX2 promoter, an ICL1 promoter, or an FLD1 promoter. Optionally, the O-RS can be expressed from a constitutive promoter, e.g., a YPT1 promoter or a GAP promoter. The O-tRNA can optionally be expressed from a high-level constitutive promoter, e.g., a PGK1 promoter. The O-RS and the O-tRNA of the methylotrophic yeast cell are optionally derived from a non-eukaryotic organism, e.g., an *Escherichia coli*.

The methylotrophic yeast cell can optionally comprise a nucleic acid that comprises a polynucleotide that encodes a polypeptide of interest, wherein the polynucleotide comprises a selector codon that is recognized by the O-tRNA. The nucleic acid encoding the polypeptide of interest can optionally be integrated into the genome in a single copy, and the integration can optionally be mediated via gene replacement at a locus encoding a non-essential gene, e.g., AOX1, and, as a result, producing cells with a mut$^S$ methanol utilization phenotype. Optionally, the nucleic acid encoding the polypeptide of interest can be integrated into the genome in multiple copies, producing cells with a Mut$^+$ methanol utilization phenotype. The polypeptide of interest encoded by the nucleic acid can optionally include, but is not limited to, any of the proteins and polypeptides as discussed herein. The polypeptide of interest is optionally expressed from an inducible promoter, e.g., an AOX1 promoter, an AOX2 promoter, an ICL1 promoter, or an FLD1 promoter. Optionally, the polypeptide of interest can be expressed from a constitutive promoter, e.g., a YPT1 promoter or a GAP promoter.

In another aspect, the invention provides methods for producing, in a methylotrophic yeast cell, a polypeptide of interest comprising an unnatural amino acid at a selected position. These methods comprise providing a methylotrophic yeast cell comprising an unnatural amino acid, an orthogonal aminoacyl-tRNA synthetase (O-RS) that preferentially aminoacylates an orthogonal tRNA (O-tRNA) with the unnatural amino acid in the methylotrophic yeast, an orthogonal tRNA (O-tRNA) that is preferentially aminoacylated by the O-RS with the unnatural amino acid, and a nucleic acid of interest encoding a polypeptide of interest, wherein the nucleic acid of interest comprises at least one selector codon that is recognized by the O-tRNA. The methylotrophic yeast cell can optionally be a *Candida* cell, a *Hansenula* cell, a *Torulopsis* cell, or a *Pichia* cell, e.g., a *Pichia pastoris* cell. The methods also include incorporating the unnatural amino acid at a selected position in the nucleic acid of interest during translation of the polypeptide of interest in response to a selector codon, thereby producing the polypeptide of interest comprising the unnatural amino acid at the selected position. Providing an unnatural amino acid can optionally comprise providing any of the unnatural amino acids discussed herein.

Providing an O-RS can optionally comprise integrating an O-RS polynucleotide that encodes the O-RS downstream of a promoter into the genome of the cell and expressing the encoded O-RS. Integrating the O-RS polynucleotide into the genome of the cell can optionally comprise integrating the polynucleotide at a locus encoding an ARG4 gene, an ADE1 gene, a HIS4 gene, a URA3 gene, an AOX1 gene, an AOX2 gene, or a MET2 gene. The O-RS can optionally be expressed from an inducible promoter, e.g., an AOX1 promoter, an AOX2 promoter, an ICL1 promoter, or an FLD1 promoter, or from a constitutive promoter, e.g., a YPT1 promoter or a GAP promoter.

Providing an O-tRNA includes providing an amber suppressor tRNA, an ochre suppressor tRNA, an opal suppressor tRNA, or a tRNA that recognizes a four base codon, a rare codon, or a non-coding codon. Providing an O-tRNA can optionally include integrating an O-tRNA polynucleotide, which encodes the O-tRNA downstream of a high-level constitutive promoter, into the genome of the cell and expressing the O-tRNA. Integrating the O-tRNA polynucleotide into the genome of the cell can optionally comprise integrating the polynucleotide at a locus encoding an ARG4 gene, an ADE1 gene, a HIS4 gene, a URA3 gene, an AOX1 gene, an AOX2 gene, or a MET2 gene. The O-tRNA can optionally be expressed from a PGK1 promoter.

Providing a nucleic acid of interest that encodes a polypeptide of interest can comprise providing a nucleic acid that optionally encodes, but is not limited to, any of the proteins and polypeptide discussed herein. Providing the nucleic acid of interest can optionally include placing the nucleic acid of interest under the transcriptional control of an inducible promoter, e.g., an AOX1 promoter, an AOX2 promoter, an ICL1 promoter, or an FLD1 promoter, or a constitutive promoter, e.g., a YPT1 promoter or a GAP promoter. Providing the nucleic acid of interest can also include integrating it into the genome of the cell. The nucleic acid of interest can optionally be integrated into the genome in single copy, e.g., at a locus encoding an AOX1 gene, an ADE1 gene, a HIS4 gene, a URA3 gene, an ARG4 gene, an AOX2 gene, or a MET2 gene. Optionally, the nucleic acid of interest can be integrated into the genome of the cell in multiple copies, e.g., at a locus 5' of the AOX1 gene.

Producing a polypeptide comprising an unnatural amino acid at a selected position can optionally comprise culturing an appropriately prepared methylotrophic yeast cell, e.g., a *Candida* cell, a *Hansenula* cell, a *Torulopsis* cell, or a *Pichia* cell, e.g., a *Pichia pastoris* cell, in a 1:9 ratio of buffered complex methanol media (BMMY):buffered minimal methanol (BMM), and growing the culture in a shake flask to induce expression of the polypeptide. Optionally, producing a polypeptide comprising an unnatural amino acid at a selected position can include growing the yeast culture until it reaches the consistency of a paste. The produced polypeptide can optionally comprise a disulfide bond, be sulfated and/or be glycosylated. The produced polypeptide can optionally be expressed from the culture at a concentration of up to 10 mg/L.

Producing a polypeptide comprising an unnatural amino acid at a selected position in *Pichia pastoris* can comprise inoculating YPD medium with a colony of an appropriate *Pichia pastoris* strain to produce a first culture, growing the first culture to near saturation in a shake flask that has been shaking at 280 rpm at a temperature between 29° C. and 30° C., and using the first culture to inoculate 1 liter of buffered media glycerol yeast extract (BMGY) to produce a second culture. The method includes growing the second culture to an $OD_{600}$ of 8.0, centrifuging the second culture at 1500×g for 5 minutes to form a pellet, and resuspending the pellet in 200 ml of a 1:9 ratio of buffered complex methanol media (BMMY):buffered minimal methanol (BMM) to produce a third culture. Finally, the method for producing a polypeptide comprising an unnatural amino acid at a selected position in *Pichia pastoris* includes adding methanol to the third culture to a final concentration of 0.5% every 24 hours thereafter for 120-144 hours to maintain induction of the polypeptide.

Kits are also a feature of the invention. For example, kits can contain an unnatural amino acid and a methylotrophic yeast cell of the invention. The cell can optionally comprise a nucleic acid encoding an O-tRNA and/or a nucleic acid encoding an O-RS integrated into its genome, e.g., wherein the O-RS and O-tRNA are under the transcriptional control of any of the promoters recited previously. Kits can comprise components for using the cells herein, such as instructions to integrate a nucleic acid comprising one or more selector codon, which nucleic acid encodes a polypeptide of interest into the methylotrophic yeast cell's genome. The kit can include a container to hold the kit components, instructional materials for practicing any method herein with the cells provided with the kit, e.g., for producing a polypeptide of interest comprising one or more unnatural amino acid at a selected position.

Those of skill in the art will appreciate that the methods, kits and compositions provided by the invention can be used alone or in combination. For example, a methylotrophic yeast cell of the invention can be used in the methods described herein to produce a polypeptide of interest comprising an unnatural amino acid at a selected position. Alternately or additionally, these methods can be used to produce, e.g., a sulfated polypeptide, a glycosylated polypeptide, and/or a polypeptide comprising one or more disulfide bonds, at concentrations of up to 10 mg/L. One of skill will appreciate further combinations of the features of the invention noted herein.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "an aminoacyl tRNA synthetase (RS)" optionally includes combinations of two or more RS molecules; reference to "a nucleic acid" or "a cell" optionally includes, as a practical matter, many copies of that nucleic acid or many cells.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

Cognate: The term "cognate" refers to components that function together, or have some aspect of specificity for each other, e.g., an orthogonal tRNA (O-tRNA) and an orthogonal aminoacyl-tRNA synthetase (O-RS), in which the O-RS specifically aminoacylates the O-tRNA with an unnatural amino acid.

Derived from: As used herein, the term "derived from" refers to a component that is isolated from or made using a specified molecule or organism, or sequence information from the specified molecule or organism. For example, a polypeptide that is derived from a second polypeptide can include an amino acid sequence that is identical or substantially similar to the amino acid sequence of the second polypeptide. In the case of polypeptides, the derived species can be obtained by, for example, naturally occurring mutagenesis, artificial directed mutagenesis or artificial random mutagenesis. The mutagenesis used to derive polypeptides can be intentionally directed or intentionally random, or a mixture of each. The mutagenesis of a polypeptide to create a different polypeptide derived from the first can be a random event, e.g., caused by polymerase infidelity, and the identification of the derived polypeptide can be made by appropriate screening methods, e.g., as discussed in references cited herein. Mutagenesis of a polypeptide typically entails manipulation of the polynucleotide that encodes the polypeptide.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In some aspects, the term "encode" describes the process of semi-conservative DNA replication, where one strand of a double-stranded DNA molecule is used as a template to encode a newly synthesized complementary sister strand by a DNA-dependent DNA polymerase. In another aspect, the term "encode" refers to any process whereby the information in one molecule is used to direct the production of a second molecule that has a different chemical nature from the first molecule. For example, a DNA molecule can encode an RNA molecule, e.g., by the process of transcription incorporating a DNA-dependent RNA polymerase enzyme. Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

In response to: As used herein, the term "in response to" refers to the process in which an O-tRNA of the invention recognizes a selector codon and mediates the incorporation of the unnatural amino acid, which is coupled to the tRNA, into the growing polypeptide chain.

Non-eukaryote: As used herein, the term "non-eukaryote" refers to organisms belonging to the Kingdom Monera (also termed Prokarya). Non-eukaryotic organisms, e.g., prokaryotic organisms, are generally distinguishable from eukaryotes by their unicellular organization, asexual reproduction by budding or fission, the lack of a membrane-bound nucleus or other membrane-bound organelles, a circular chromosome, the presence of operons, the absence of introns, message capping and poly-A mRNA, and other biochemical characteristics, such as a distinguishing ribosomal structure. The Prokarya include subkingdoms Eubacteria and Archaea (sometimes termed "Archaebacteria"). Cyanobacteria (the blue green algae) and mycoplasma are sometimes given separate classifications under the Kingdom Monera.

Orthogonal: As used herein, the term "orthogonal" refers to a molecule, e.g., an orthogonal tRNA (O-tRNA) and/or an orthogonal aminoacyl-tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency, e.g., 45% efficiency, 50% efficiency, 60% efficiency, 70% efficiency, 75% efficiency, 80% efficiency, 90% efficiency, 95% efficiency, or 99% or more efficiency, as compared to that of a control, e.g., a corresponding tRNA/RS endogenous pair, or an active orthogonal pair.

Orthogonal aminoacyl tRNA synthetase: As used herein, an orthogonal aminoacyl tRNA synthetase (O-RS) is an enzyme that preferentially aminoacylates the O-tRNA with an amino acid in a translation system of interest. The amino acid that the O-RS loads onto the O-tRNA can be any amino acid, whether natural, unnatural or artificial, and is not limited herein. The synthetase is optionally the same as or homologous to a naturally occurring tyrosyl amino acid synthetase, or the same as or homologous to a synthetase designated as an O-RS.

Orthogonal tRNA: As used herein, an orthogonal tRNA (O-tRNA) is a tRNA that is orthogonal to a translation system of interest, where the tRNA is, e.g., (1) identical or substantially similar to a naturally occurring tRNA, (2) derived from a naturally occurring tRNA by natural or artificial mutagenesis, (3) derived by any process that takes a sequence of a wild-type or mutant tRNA sequence of (1) or (2) into account, (4) homologous to a wild-type or mutant tRNA; (5) homologous to any example tRNA that is designated as a substrate for an orthogonal tRNA synthetase or (6) a conservative variant of any example tRNA that is designated as a substrate for an orthogonal tRNA synthetase. The O-tRNA can exist charged with an amino acid, or in an uncharged state. It is also to be understood that a "O-tRNA" optionally is charged (aminoacylated) by a cognate synthetase with an unnatural amino acid. Indeed, it will be appreciated that an O-tRNA of the invention is advantageously used to insert essentially any unnatural amino acid into a growing polypeptide, during translation, in response to a selector codon.

Polypeptide: A polypeptide is any oligomer of amino acid residues (natural or unnatural, or a combination thereof), of any length, typically but not exclusively joined by covalent peptide bonds. A polypeptide can be from any source, e.g., a naturally occurring polypeptide, a polypeptide produced by recombinant molecular genetic techniques, a polypeptide from a cell or translation system, or a polypeptide produced by cell-free synthetic means. A polypeptide is characterized by its amino acid sequence, e.g., the primary structure of its component amino acid residues. As used herein, the amino acid sequence of a polypeptide is not limited to full-length sequences, but can be partial or complete sequences. Furthermore, it is not intended that a polypeptide be limited by possessing or not possessing any particular biological activity. As used herein, the term "protein" is synonymous with polypeptide. The term "peptide" refers to a small polypeptide, for example but not limited to, from 2-25 amino acids in length.

Preferentially aminoacylates: As used herein in reference to orthogonal translation systems, an O-RS "preferentially aminoacylates" a cognate O-tRNA when the O-RS charges the O-tRNA with an amino acid more efficiently than it charges any endogenous tRNA in an expression system. That is, when the O-tRNA and any given endogenous tRNA are present in a translation system in approximately equal molar ratios, the O-RS will charge the O-tRNA more frequently than it will charge the endogenous tRNA. Preferably, the relative ratio of O-tRNA charged by the O-RS to endogenous tRNA charged by the O-RS is high, preferably resulting in the O-RS charging the O-tRNA exclusively, or nearly exclusively, when the O-tRNA and endogenous tRNA are present in equal molar concentrations in the translation system. The relative ratio between O-tRNA and endogenous tRNA that is charged by the O-RS, when the O-tRNA and O-RS are present at equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

The O-RS "preferentially aminoacylates an O-tRNA with an unnatural amino acid" when (a) the O-RS preferentially aminoacylates the O-tRNA compared to an endogenous tRNA, and (b) where that aminoacylation is specific for the unnatural amino acid, as compared to aminoacylation of the O-tRNA by the O-RS with any natural amino acid. That is, when the unnatural and natural amino acids are present in equal molar amounts in a translation system comprising the O-RS and O-tRNA, the O-RS will load the O-tRNA with the unnatural amino acid more frequently than with the natural amino acid. Preferably, the relative ratio of O-tRNA charged with the unnatural amino acid to O-tRNA charged with the natural amino acid is high. More preferably, O-RS charges the O-tRNA exclusively, or nearly exclusively, with the unnatural amino acid. The relative ratio between charging of the O-tRNA with the unnatural amino acid and charging of the O-tRNA with the natural amino acid, when both the natural and unnatural amino acids are present in the translation system in equal molar concentrations, is greater than 1:1, preferably at least about 2:1, more preferably 5:1, still more preferably 10:1, yet more preferably 20:1, still more preferably 50:1, yet more preferably 75:1, still more preferably 95:1, 98:1, 99:1, 100:1, 500:1, 1,000:1, 5,000:1 or higher.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppression activity: As used herein, the term "suppression activity" refers, in general, to the ability of a tRNA, e.g., a suppressor tRNA, to allow translational read-through of a codon, e.g., a selector codon that is an amber codon or a 4-or-more base codon, that would otherwise result in the termination of translation or mistranslation, e.g., frame-shifting. Suppression activity of a suppressor tRNA can be expressed as a percentage of translational read-through activity observed compared to a second suppressor tRNA, or as compared to a control system, e.g., a control system lacking an O-RS.

Suppression efficiency can be determined by any of a number of assays known in the art. For example, a β-galactosidase reporter assay can be used, e.g., a derivatized lacZ plasmid (where the construct has a selector codon in the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Suppressor tRNA: A suppressor tRNA is a tRNA that alters the reading of a messenger RNA (mRNA) in a given translation system, typically by allowing the incorporation of an amino acid in response to a stop codon (i.e., "read-through") during the translation of a polypeptide. In some aspects, a selector codon of the invention is a suppressor codon, e.g., a stop codon, e.g., an amber, ocher or opal codon, a four base codon, a rare codon, etc.

Translation system: The term "translation system" refers to the components that incorporate an amino acid into a growing polypeptide chain (protein). Components of a translation system can include, e.g., ribosomes, tRNAs, synthetases, mRNA and the like.

Unnatural amino acid: As used herein, the term "unnatural amino acid" refers to any amino acid, modified amino acid, and/or amino acid analogue, that is not one of the 20 common naturally occurring amino acids or the rare naturally occurring amino acids e.g., selenocysteine or pyrrolysine.

BRIEF DESCRIPTION OF THE DRAWINGS

FIG. 6 provides schematic illustrations of various plasmids that find use with the invention. Vectors for amber suppression in eukaryotes illustrating markers (maroon), replication origins (black), target proteins (orange), control elements (green), and suppressor tRNAs ("tRNA (CUA)", light blue). (a) Map of the commercially available pPIC3.5k shuttle vector[16] for in vivo multi-copy incorporation and expression in *P. pastoris*. $rHSA_{E37X}$ (orange) is subcloned between the AOX1 promoter and terminator. (b) Optimized amber suppression vector for *S. cerevisiae*[23] harboring the pApaRS/$tRNA_{CUA}^{tyr}$ pair under $P_{ADH1}$ control. $tRNA_{CUA}$ repeats are separated by regions from the SUP4 gene (not labeled) and driven by $P_{PGK1}$. (c) Modified pPR1-$P_{PGK1}$+3SUP4-tRNA plasmid where the 2μ eukaryotic origin and TRP marker were replaced by ARG4 to create pREAV-$P_{ADH1}$-pApaRS. (d) $P_{ADH1}$ and $T_{ADH1}$ were replaced by their AOX1 counterparts to create pREAV-$P_{AOX1}$-pApaRS. (e) The first 61 amino acids of $rHSA_{E37X}$. The pre-pro leader peptide (blue, green) allows export of $rHSA_{E37X}$ into the media and is cleaved during transport to yield the mature protein (rHSA, orange) beginning with an aspartic acid. The 37$^{th}$ residue (X, red) of the mature rHSA denotes the unnatural amino acid incorporated in response to the amber codon.

DETAILED DESCRIPTION OF THE INVENTION

Figure 1:
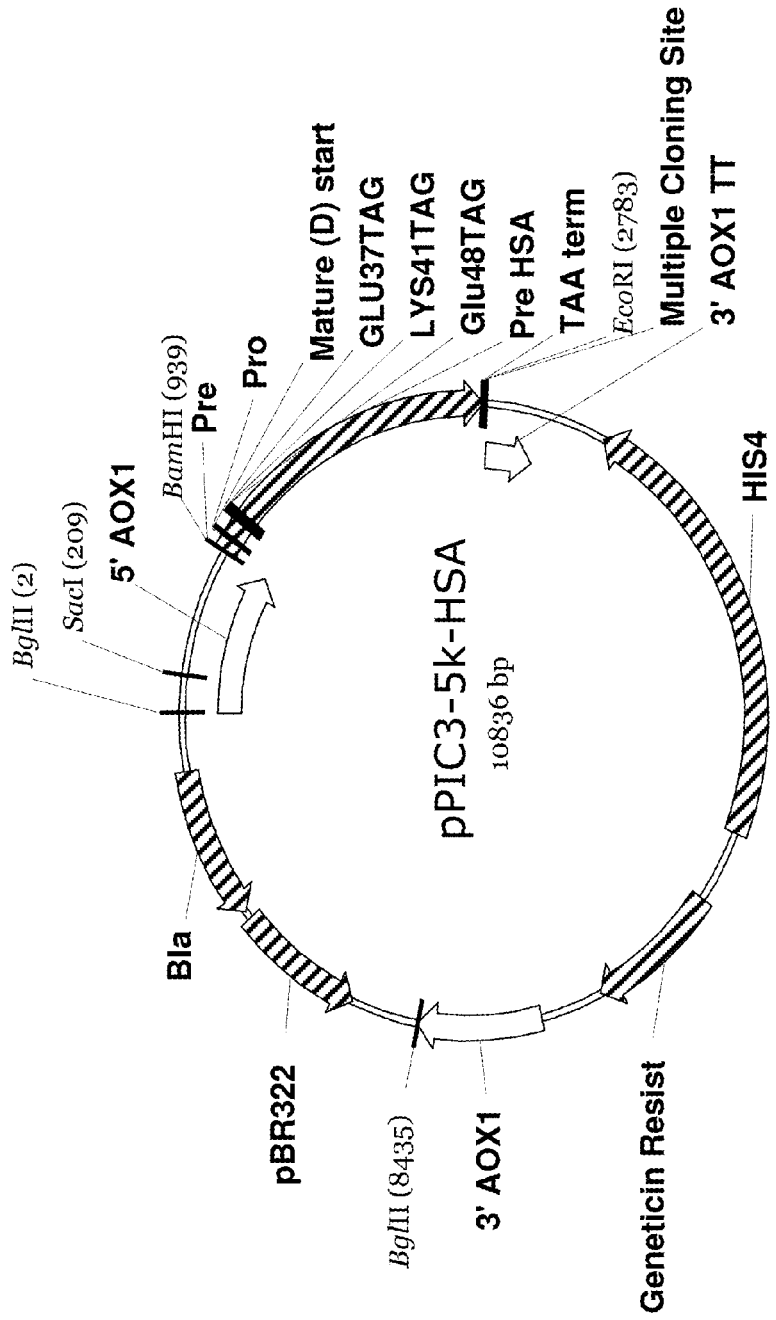
FIG. 1 depicts the plasmid that was constructed in preparation to integrate the gene encoding human serum albumin (HSA) into the *Pichia pastoris* genome.

The present invention facilitates the production of polypeptides comprising unnatural amino acids in methylotrophic yeast, e.g., *Pichia pastoris*. Polypeptides comprising unnatural amino acids can find use as therapeutic agents with novel biological properties, reduced toxicities, enhanced activities, and/or increased half-lives. The use of O-RS/O-tRNA pairs in methylotrophic yeast, e.g., *Pichia pastoris*, is characterized by several beneficial advantages over other orthogonal systems, e.g., *E. coli* or *S. cerevisiae*, for the production of such proteins. First, the eukaryotic subcellular structure of yeast, e.g., *P. pastoris*, permits the synthesis of proteins comprising unnatural amino acids (UAA) that require complex post-translational modifications, e.g., glycosylation, disulfide bond formation, sulfation, acetylation, prenylation and proteolytic processing, for biological activity, e.g., mammalian proteins such as human serum albumin (HSA) and human neutral endopeptidase (NEP). Thus, many proteins that end up as inactive inclusion bodies in bacterial systems are produced as biologically active molecules in methylotrophs, e.g., *P. pastoris*. Second, proteins comprising UAA produced in methylotrophs, e.g., *P. pastoris* do not contain high concentrations of pyrogens, e.g., lipopolysaccharides, or antigens, e.g., high-mannose oligosaccharides, that might hinder the efficacy of proteins expressly designed for therapeutic use. Third, many well established techniques and methods, e.g., gene-targeting, high-frequency DNA transformation, cloning by functional complementation, are available for the genetic manipulation of foreign genes in *P. pastoris* (Lin-Cereghino, et al, (2002) "Production of recombinant proteins in fermenter cultures of the yeast *Pichia pastoris*." *Curr Opin Biotechnol* 13: 329-332). The availability of endogenous inducible promoters and selectable markers adds flexibility to range of proteins comprising UAA that can be produced by this methylotrophic host.

In addition to these advantages, methylotrophs such as *P. pastoris* are also well suited for low-cost, large-scale synthesis of complex proteins comprising UAA. Methylotrophic yeast, e.g., *P. pastoris*, are easily cultured in a simple, defined salt medium, eliminating the need for the expensive media supplements and costly equipment that are required for, e.g., baculovirus expression systems or mammalian tissue culture. Methylotrophs such as *P. pastoris* can grow to very high cell densities, and under ideal conditions can multiply to the point where the cell suspension is the consistency of a paste. Its prolific growth rate allows recombinant *P. pastoris* strains to produce heterologous proteins, e.g., proteins comprising UAA, at high levels, e.g., 10- to 100-fold higher level than in *S. cerevisiae*. Their ease of genetic manipulation, their economy of recombinant protein production, and their abilities to perform the posttranslational modifications typically associated with eukaryotic proteins make methylotrophic yeast, e.g., *P. pastoris*, an advantageous system for the expression of heterologous proteins comprising UAA.

Orthogonal Translation System Components

An understanding of the novel compositions and methods for synthesizing proteins comprising unnatural amino acids in methylotrophic yeast are further developed through an understanding of the activities associated with orthogonal tRNA and orthogonal aminoacyl-tRNA synthetase pairs. The incorporation of unnatural amino acids into these polypeptides is accomplished by adapting an orthogonal tRNA (O-tRNA) and an orthogonal aminoacyl-tRNA synthetase (O-RS) to recognize the desired unnatural amino acid and incorporate it into proteins in response to a selector codon, e.g., an amber nonsense codon, TAG. These orthogonal components do not cross-react with endogenous components of the translational machinery of the host cell, e.g., a *P. pastoris* cell, or with naturally occurring amino acids. The orthogonal components used in one example herein include an O-RS, e.g., an O-RS derived from *E. coli* tyrosyl tRNA-synthetase, and O-tRNA, e.g., the mutant tyrosyl tRNA$_{CUA}$ amber suppressor, which function as an orthogonal pair in host cells, e.g., *P. pastoris*.

As used herein, an unnatural amino acid refers to any amino acid, modified amino acid, or amino acid analogue other than selenocysteine and/or pyrrolysine and the twenty genetically encoded alpha-amino acids. See, e.g., *Biochemistry* by L. Stryer, 3$^{rd}$ ed. 1988, Freeman and Company, New York, for structures of the twenty natural amino acids. Unnatural amino acids of the invention have side chain groups that distinguish them from the natural amino acids, although unnatural amino acids can be naturally occurring compounds other than the twenty proteinogenic alpha-amino acids. The unnatural amino acids finding use with the invention include an p-(propargyloxy)phenylalanine, p-methoxyphenylalanine, dansylalanine, DMNB-serine, O-methyl-L-tyrosine, an L-3-(2-naphthyl)alanine, an O-4-allyl-L-tyrosine, an O-propargyl-L-tyrosine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, sulfo, seleno, ester, thioacid, borate, boronate, phospho, phosphono, heterocyclic, enone, imine, aldehyde, alkoxyamine, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a sugar-substituted cysteine; a redox-active amino acid; an α-hydroxy containing acid; an amino thio acid containing amino acid; an α,α disubstituted amino acid; a β-amino acid; sulfotyrosine, 4-borono-phenylalanine, or a cyclic amino acid other than proline.

The invention optionally includes multiple O-tRNA/O-RS pairs. For example, the invention can further include an additional O-tRNA/O-RS pair where the second O-RS preferentially aminoacylates the second O-tRNA with a second unnatural amino acid, and the second O-tRNA recognizes a second selector codon. A number of different selector codons, e.g., a unique three base codon, a nonsense codon, such as a stop codon, e.g., an amber codon (UAG), or an opal codon (UGA), an unnatural codon, at least a four base codon, a rare codon, or the like, can be introduced into a gene, e.g., the coding sequence of a vector nucleic acid and/or a complementation nucleic acid. Multiple orthogonal tRNA/synthetase pairs can be used that allow the simultaneous site-specific incorporation of multiple unnatural amino acids, e.g., including at least one unnatural amino acid, using these different selector codons. Such O-tRNA/O-RS pairs can be derived from any of a variety of sources, as long as the O-tRNA/O-RS pairs retain their orthogonality in the methylotrophic yeast cell's environment Methods for producing and/or altering the specificity of O-tRNAs and/or O-RSes, unnatural amino acids, selector codons, and orthogonal translation systems that are suitable for making proteins that include one or more unnatural amino acids are generally described in, for example, International Publication Numbers WO 2002/086075, entitled "METHODS AND COMPOSITION FOR THE PRODUCTION OF ORTHOGONAL tRNA-AMINOACYL-tRNA SYNTHETASE PAIRS;" WO 2002/085923, entitled "IN VIVO INCORPORATION OF UNNATURAL AMINO ACIDS;" and WO 2004/094593, entitled "EXPANDING THE EUKARYOTIC GENETIC CODE;" WO 2005/019415, filed Jul. 7, 2004; WO 2005/007870, filed Jul. 7, 2004 and WO 2005/007624, filed Jul. 7, 2004. Each of these applications is incorporated herein by reference in its entirety. See also, Wang and Schultz "Expanding the Genetic Code," Angewandte Chemie Int. Ed., 44(1):34-66 (2005); Deiters, et al. Bioorganic & Medicinal Chemistry Letters 15:1521-1524 (2005); Chin, et al. J. Am. Chem. Soc. 2002, 124, 9026-9027; and International Publication No. WO2006/034332, filed on Sep. 20, 2005, the contents of each of which are incorporated by reference in their entirety. Additional details are found in U.S. Pat. No. 7,045,337; U.S. Pat. No. 7,083,970; U.S. Pat. No. 7,238,510; U.S. Pat. No. 7,129,333; U.S. Pat. No. 7,262,040; U.S. Pat. No. 7,183,082; U.S. Pat. No. 7,199,222; and U.S. Pat. No. 7,217,809.

Expression and Purification of Heterologous Proteins in Methylotrophic Yeast

The four known genera of methylotrophic yeast, e.g., Hansenula, Pichia, Candida, and Torulopsis, share a common metabolic pathway that enables them to use methanol as a sole carbon source. In a transcriptionally regulated response to methanol induction, several of the enzymes are rapidly synthesized at high levels. Since the promoters controlling the expression of these genes are among the strongest and most strictly regulated yeast promoters, methylotrophic yeast have become very attractive as hosts for the large scale production of recombinant proteins. The cells of these methylotrophic yeast can be grown rapidly to high densities, and the level of product expression can be regulated by simple manipulation of the medium. Expression systems have this far been developed in P. pastoris, P. methanolica, P. angusta (also known as Hansenula polymorpha) and Candida boidinii, and these systems are further elaborated in, e.g., Houard, et al. (2002)"Engineering of non-conventional yeasts for efficient synthesis of macromolecules: the methylotrophic genera." Biochimie 84: 1089-1093; Gellison (2002) Hansenula Polymorpha: Biology and Applications, 1st Ed., Wiley-VCH, N.Y.; U.S. Pat. No. 6,645,739. Gellisen (2000) "Heterologous protein production in methylotrophic yeasts." Applied Microbiology and Biotechnology 54: 741-750. Many of these systems are commercially available, e.g., Hansenula kits from Artes Biotecnology and Pichia kits from Invitrogen, for use in academic and industrial laboratories.

In a preferred embodiment, heterologous proteins are expressed and purified from the methylotroph P. pastoris. As described below, e.g., in METHODS AND STRATEGIES FOR STRAIN CONSTRUCTION IN METHYLOTROPHIC YEAST, foreign genes can be expressed in P. pastoris from the alcohol oxidase 1 (AOX1) promoter, the regulatory characteristics of which are well suited for this purpose. The AOX1 promoter is tightly repressed during growth of the yeast on most carbon sources, e.g., glycerol, glucose, or ethanol, but is highly induced during growth on methanol (Tschorp et al. (1987) "Expression of the lacZ gene from two methanol-regulated promoters in Pichia pastoris." Nucl Acids Res 15: 3859-3876). Expression of proteins encoded by genes regulated by $P_{AOX1}$ can typically reach ≥30% of the total soluble protein in P. pastoris cells grown on methanol. For the production of recombinant proteins, $P_{AOX1}$-controlled expression strains are grown initially on a repressing carbon source to generate biomass, e.g., maximize culture density, and then shifted to a methanol-containing medium, e.g., BMGY, BMMY, or BMM, as the sole energy source to induce expression of the foreign gene.

However, promoters that are not induced by methanol can also be advantageous for the expression of heterologous genes encoding certain proteins. Alternative promoters to the AOX1 promoter in this expression system are the P. pastoris GAP, FLD1, AOX2, ILC1, and YPT1 promoters. Further details regarding the regulation of these promoters, the circumstances under which it may be beneficial to express a foreign gene from these promoters, and the expression of foreign proteins in P. pastoris by these promoters are discussed in, e.g., Sears, et al. (1998) "A Versatile Set of Vectors for Constitutive and Regulated Gene Expression in Pichia pastoris." Yeast 14: 783-790; Vassileva, et al. (2001) "Expression of hepatitis B surface antigen in the methylotrophic yeast Pichia pastoris using the GAP promoter." J Biotechnology 88: 21-35; Shen, et al. (1998) "A strong nitrogen-source regulated promoter for controlled expression of foreign genes in the yeast Pichia pastoris." Gene 216: 93-102; Lin-Cereghino, et al. "Expression of foreign genes in the yeast Pichia pastoris." Genetic Engineering Principles and Methods, Vol. 23 $1^{st}$ Ed. Ed. Jane K. Setlow, Springer, N.Y.: (2005).

Although expression of heterologous proteins in *P. pastoris* or other methylotrophic yeast can be done in shake-flask culture, protein levels expressed in this system are typically much higher in fermenter cultures, because it is in fermenters that parameters such as pH, aeration, and carbon source feed rate can be controlled to achieve ultra-high cell densities, e.g., >100 g/L dry cell weight; >400 g/L wet cell weight, >500 $OD_{600}$ units/ml (see, e.g., Lin-Cereghino, et al. (2002) "Production of recombinant proteins in fermenter cultures of the yeast *Pichia pastoris.*" *Curr Opin Biotechnol* 13: 329-332. A hallmark of the *P. pastoris* expression system is the ease with which expression strains scale up from shake-flask to high-density fermenter cultures.

A three step process is typically employed to express heterologous proteins, e.g., proteins encoded by genes under the transcriptional control of $P\text{-}_{AOX1}$, in fermenter cultures of *P. pastoris* or other methylotrophic yeast. In the first step, the engineered *P. pastoris* or other methylotrophic yeast expression strain is cultured in a simple, defined, medium comprising a non-fermentable, $P_{AOX1}$-repressing carbon source to permit the cell growth. The second step comprises a transition phase during which glycerol is fed to the culture at a growth-limiting rate to further increase the culture's biomass and to prepare the cells for induction. During the third step, methanol is added to the culture at a rate that allows the cells to physiologically acclimate to metabolizing methanol and to synthesize the recombinant protein. The methanol feed rate is then adjusted upwards periodically until the desired growth rate and protein expression rate is achieved (Lin-Cereghino, et al. "Expression of foreign genes in the yeast *Pichia pastoris.*" *Genetic Engineering Principles and Methods*, Vol. 23 $1^{st}$ Ed. Ed. Jane K. Setlow, Springer, N.Y.: (2005)).

The media in which *P. pastoris* can be grown are inexpensive and highly defined, consisting of carbon sources, e.g., glycerol and/or methanol, biotin, salts, trace elements, and water. The media are free of pyrogens and toxins, and are therefore compatible with the production of pharmaceutical agents for human use.

The recombinant proteins expressed in *P. pastoris* or other methylotrophic yeast can be produced either intracellularly or extracellularly. Because this yeast secretes only low levels of endogenous protein, secreted recombinant protein can constitute the majority of protein in the medium. Therefore, directing the recombinant protein into the culture medium can serve as a first step in protein purification, eliminating the need to follow harsh yeast lysis protocols and avoiding the possibility of contamination of the recombinant protein by endogenous *P. pastoris* proteins. However, due to protein stability and folding requirements, secreting a heterologous protein into the medium is typically reserved only for those proteins that are normally secreted by their native host cells. Nevertheless, kits are available, e.g., Original *Pichia* Expression Kit (Invitrogen), Multi-Copy *Pichia* Expression Kit (Invitrogen), *Pichia* Protein Expression System (Research Corporation Technologies), in which pre-made expression cassettes allow practitioners to clone a gene of interest in frame with sequences encoding its native secretion signal, the *S. cerevisiae* α-factor prepro peptide, or the *P. pastoris* acid phosphatase (PHO1) signal to allow secretion into the culture medium. A number of techniques for the recovery of intracellular recombinant proteins from *P. pastoris* have also been developed (Shepard, et al. (2002) "Recovery of intracellular recombinant proteins from the yeast *Pichia pastoris* by cell permeabilization." *J Biotechnology* 99: 149-160; U.S. Pat. No. 6,821,752).

General Methods for Protein Purification

A variety of protein purification methods are well known in the art and can be applied to the purification and analysis of proteins comprising UAA expressed in methylotrophic yeast. These techniques, and others that are necessary for the analysis of polypeptides, include those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag, et al. (1996) *Protein Methods*, 2nd Edition Wiley-Liss, N.Y.; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* 3rd Edition Springer Verlag, N.Y.; Janson and Ryden (1998) *Protein Purification: Principles, High Resolution Methods and Applications, Second Edition* Wiley-VCH, N.Y.; and Walker (1998) *Protein Protocols on CD-ROM* Humana Press, NJ; and the references cited therein.

Methods and Strategies for Strain Construction in Methylotrophic Yeast

Shuttle vectors that are suitable for replication in *E. coli* are typically used to engineer nucleic acid constructs that place a gene of interest under the control of a highly inducible methylotrophic yeast promoter. Because plasmids are relatively unstable in methylotrophic yeast, the expression constructs are then usually linearized and transformed into e.g., a *Pichia* cell, a *Hansenula* cell, a *Candida* cell, or a *Torulopsis* cell, and integrated into the genome. Integration is generally site specific; however, high frequencies of non-homologous integration have been observed in *Hansenula polymorpha* (Agaphonov, et al. (2005) "Defect of vacuolar protein sorting stimulates proteolytic processing of human urokinase-type plasminogen activator in the yeast *Hansenula polymorpha.*" *FEMS Yeast Reseach* 5: 1029-1035). Additional details regarding the general molecular manipulation, e.g., transformation, gene targeting, cloning by functional complementation, use of available selectable markers, and the like, of methylotrophic yeast can be found in, e.g.; Peberdy, Ed. (1991) *Applied Molecular Genetics of Fungi*. Cambridge University Press, UK; *Hansenula Polymorpha: Biology and Applications*, 1st Ed., Wiley-VCH; Higgins and Cregg. *Pichia Protocols (Methods in Molecular Biology)*, 1st Ed. Humana Press: New Jersey (1998); and the references cited therein.

In a preferred embodiment, heterologous genes are expressed in the methylotroph *P. pastoris*. Expression of most foreign genes in *P. pastoris* can be performed by following three basic steps: The insertion of the gene of interest into an expression vector; the introduction of the expression vector into the *P. pastoris* genome; and analysis of the putative expression strain for production of the protein expressed by the foreign gene, methods for which are described above in METHODS AND STRATEGIES FOR STRAIN CONSTRUCTION IN METHYLOTROPHIC YEAST. Fortunately, techniques for the molecular genetic manipulation of *P. pastoris*, e.g., DNA-mediated transformation, gene targeting, gene replacement, and cloning by functional complementation, are similar to those described for *S. cerevisiae*. In contrast to *S. cerevisiae*, however, plasmids are unstable in *P. pastoris*, and expression constructs encoding a protein of interest are instead integrated into the *P. pastoris* genome via homologous recombination.

Protocols for the molecular genetic manipulation of *P. pastoris* are discussed in detail in, e.g., Cregg, et al. (1985) "*Pichia pastoris* as a host system for transformations." *Molec Cell Biol* 5: 3376-3385; Lin-Cereghino, et al. "Expression of foreign genes in the yeast *Pichia pastoris*." *Genetic Engineering Principles and Methods, Vol.* 23 1st *Ed.* Ed. Jane K. Setlow, Springer, N.Y.: (2005); Higgins and Cregg. *Pichia Protocols (Methods in Molecular Biology)*, 1st *Ed.* Humana Press: New Jersey (1998); Lin-Cereghino, et al. (2000) "Heterologous protein expression in the methylotrophic yeast *Pichia pastoris*." *FEMS Microbiol Rev* 24: 45-66, and in the references cited therein.

A variety of *P. pastoris* host strains and expression vectors are available. Virtually all *P. pastoris* expression strains are derived from NRRL-Y 111430 (Northern Regional Research Laboratories, Peoria, Ill.). Most expression strains have one or more auxotrophic markers that permit selection of expression vectors comprising the appropriate complementary markers. Host strains can differ in their abilities to metabolize methanol because of deletions in AOX1, AOX2, or both. In fact, strains carrying mutations in AOX1 and/or AOX2 can be better producers of foreign proteins than wild-type strains (Cregg. Et al. (1987) "High level expression and efficient assembly of hepatitis B antigen in the methylotrophic yeast, *Pichia pastoris*." *Bio/Technology* 5: 479-485; Chiruvolu, et al. (1997) "Recombinant protein production in an alcohol oxidase-defective strain of *Pichia pastoris* in fed-batch fermentation." *Enzyme Microb Technol* 21: 277-283). Nevertheless, even aox1⁻ strains retain the ability to induce expression of foreign proteins at high levels from the AOX1 promoter. More detailed information host strains, including protease deficient host strains in which the expression of certain recombinant proteins may be more beneficial, is available in, e.g., Brierley, et al. (1998) "Secretion of recombinant insulin-like growth factor-1 (IGF-1)." *Methods Mol Biol* 103: 149-177; White, et al. (1995) "Large-scale expression, purification, and characterization of small fragments of thrombomodulin: the roles of the sixth domain and of methionine 388." *Protein Eng* 8: 1177-1187.

Most *P. pastoris* expression vectors have been designed as *E. coli/P. pastoris* shuttle vectors, containing origins of replication for maintenance in *E. coli* and selectable markers that are functional in one or both organisms, e.g., ARG4, HIS4, ADE1, URA3, TRP1 and certain antibiotics, e.g., Zeocin™ and Geneticin®, which are selectable in *P. pastoris*, and/or any of a number of antibiotic resistance markers which are selectable in *E. coli*. Typically, an expression vector will comprise 5' AOX1 promoter sequences and AOX1-derived sequences for transcriptional termination, between which lies a multiple cloning site. Although the AOX1 promoter has been successfully used to express numerous foreign proteins, there are circumstances under which the use of this promoter may not be suitable, e.g., for the production of food products. Alternative promoters to the AOX1 promoter in this expression system are the *P. pastoris* AOX2, ICL1, GAP, FLD1, and YPT1 promoters. Generalized diagrams of expression vectors comprising any of the aforementioned promoters and lists of possible vector components are also given in, e.g., Lin-Cereghino, et al. "Expression of foreign genes in the yeast *Pichia pastoris*." *Genetic Engineering Principles and Methods, Vol.* 23 1st *Ed.* Ed. Jane K. Setlow, Springer, N.Y.: (2005) and Lin-Cereghino, et al. (2000) "Heterologous protein expression in the methylotrophic yeast *Pichia pastoris*." *FEMS Microbiol Rev* 24: 45-66. In addition, the DNA sequences of many vectors can be found at the Invitrogen website (www.invitrogen.com), and are available from Invitrogen individually and in *P. pastoris* expression kits.

General Molecular Cloning Methods and Techniques

Procedures for isolating, cloning, and amplifying nucleic acids in preparation for, e.g., cloning a gene of interest into an expression construct as described above in METHODS AND STRATEGIES FOR STRAIN CONSTRUCTION IN METHYLOTROPHIC YEAST, are replete in the literature and can be used in the present invention to, e.g., provide and express a gene of interest in a methylotrophic yeast, e.g., *P. pastoris*. Further details these techniques can be found in Berger and Kimmel, *Guide to Molecular Cloning Techniques, Methods in Enzymology* volume 152 Academic Press, Inc., San Diego, Calif. (Berger); Sambrook, et al. *Molecular Cloning—A Laboratory Manual* (3rd Ed.), Vol. 1-3, Cold Spring Harbor Laboratory, Cold Spring Harbor, N.Y., 2000 ("Sambrook"); *The Nucleic Acid Protocols Handbook* Ralph Rapley (ed) (2000) Cold Spring Harbor, Humana Press Inc (Rapley); *Current Protocols in Molecular Biology*, F. M. Ausubel, et al. eds., Current Protocols, a joint venture between Greene Publishing Associates, Inc. and John Wiley & Sons, Inc., (supplemented through 2007) ("Ausubel")); *PCR Protocols A Guide to Methods and Applications* (Innis, et al. eds) Academic Press Inc. San Diego, Calif. (1990) (Innis); Chen, et al. (ed) *PCR Cloning Protocols, Second Edition* (Methods in Molecular Biology, volume 192) Humana Press; in Viljoen, et al. (2005) *Molecular Diagnostic PCR Handbook* Springer; and Demidov and Broude (eds) (2005) *DNA Amplification: Current Technologies and Applications*. Horizon Bioscience, Wymondham, UK. Other useful references, e.g., for cell isolation and culture, e.g., for subsequent nucleic acid isolation, include Freshney (1994) *Culture of Animal Cells, a Manual of Basic Technique*, third edition, Wiley-Liss, New York and the references cited therein; Payne, et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

A plethora of kits are also commercially available for the purification of plasmids or other relevant nucleic acids from cells, (see, e.g., EasyPrep™, FlexiPrep™ both from Pharmacia Biotech; StrataClean™, from Stratagene; QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. See Sambrook, Ausubel and Berger. In addition, essentially any nucleic acid can be custom or standard ordered from any of a variety of commercial sources, such as Operon Technologies Inc. (Huntsville, Ala.).

Proteins and Polypeptides of Interest

The present invention provides compositions and methods for the incorporation of unnatural amino acids into proteins synthesized by methylotrophic yeast, e.g., *P. pas-*

*toris*. This invention can be particularly useful in the development of and large-scale production of therapeutic proteins with enhanced biological properties, reduced toxicities, and/or increased half-lives. Examples of such therapeutic, diagnostic, and other polypeptides that are most beneficially expressed by using the methods and compositions described herein include, but are not limited to, an HSA, a human neutral endopeptidase (NEP), an antibody, an Fab, an Fv, an alpha-1 antitrypsin, an angiostatin, an antihemolytic factor, an apolipoprotein, an apoprotein, an atrial natriuretic factor, an atrial natriuretic polypeptide, an atrial peptide, a C-X-C chemokine, a T39765, a NAP-2, an ENA-78, a gro-a, a gro-b, a gro-c, an IP-10, a GCP-2, a NAP-4, an SDF-1, a PF4, a MIG, a calcitonin, a c-kit ligand, a cytokine, a CC chemokine, a monocyte chemoattractant protein-1, a monocyte chemoattractant protein-2, a monocyte chemoattractant protein-3, a monocyte inflammatory protein-1 alpha, a monocyte inflammatory protein-1 beta, a RANTES, an 1309, an R83915, an R91733, an HCC1, a T58847, a D31065, a T64262, a CD40, a CD40 ligand, a c-kit ligand, a collagen, a colony stimulating factor (CSF), a complement factor 5a, a complement inhibitor, a complement receptor 1, a cytokine, an epithelial neutrophil activating peptide-78, a GROα, a MGSA, a GROβ, a GROγ, a MIP1-α, a MIP1-β, an MCP-1, a human epidermal growth factor (hEGF), an epithelial neutrophil activating peptide, an erythropoietin (EPO), an exfoliating toxin, a factor IX, a factor VII, a factor VIII, a factor X, a fibroblast growth factor (FGF), an FGF21, a fibrinogen, a fibronectin, a G-CSF, a GM-CSF, a human glucocerebrosidase, a gonadotropin variants, a growth factor, a growth factor receptor, a hedgehog protein, a hemoglobin, a hepatocyte growth factor (HGF), a Hirudin, a human serum albumin (HSA), an ICAM-1, an ICAM-1 receptor, an LFA-1, an LFA-1 receptor, a human insulin, a human insulin-like growth factor (hIGF), an hIGF-I, an hIGF-II, a human interferon, an IFN-α, an IFN-β, an IFN-γ, an interleukin, an IL-1, an IL-2, an IL-3, an IL-4, an IL-5, an IL-6, an IL-7, an IL-8, an IL-9, an IL-10, an IL-11, an IL-12, a keratinocyte growth factor (KGF), a lactoferrin, a leukemia inhibitory factor, a luciferase, a neurturin, a neutrophil inhibitory factor (NIF), a human oncostatin M (OSM), an osteogenic protein, an oncogene product, a parathyroid hormone, a PD-ECSF, a PDGF, a peptide hormone, a human growth hormone (hGH), a pleiotropin, a protein A, a protein G, a pyrogenic exotoxin A, a pyrogenic exotoxin B, a pyrogenic exotoxin C, a relaxin, a renin, an SCF/c-kit, a soluble complement receptor I, a soluble I-CAM 1, a soluble interleukin receptor, a soluble TNF receptor, a somatomedin, a somatostatin, a somatotropin, a streptokinase, a superantigen, a staphylococcal enterotoxin, an SEA, an SEB, an SEC1, an SEC2, an SEC3, an SED, an SEE, a steroid hormone receptor, a superoxide dismutase, a toxic shock syndrome toxin, a thymosin alpha 1, a tissue plasminogen activator, a tumor growth factor (TGF), a TGF-α, a TGF-β, a human tumor necrosis factor (hTNF), a human tumor necrosis factor alpha, a human tumor necrosis factor beta, a human tumor necrosis factor receptor (TNFR), a VLA-4 protein, a VCAM-1 protein, a human vascular endothelial growth factor (hVEGEF), hVEGF165, a Urokinase, a Mos, a Ras, a Raf, a Met, a p53, a Tat, a Fos, a Myc, a Jun, a Myb, a Rel, an estrogen receptor, a progesterone receptor, a testosterone receptor, an aldosterone receptor, an LDL receptor, an inflammatory molecule, a signal transduction molecule, a transcriptional activator, a transcriptional suppressor, a hyalurin, a CD44, a corticosterone, a human thyroid peroxidase (hTPO), a tetanus toxin fragment C, a bovine pancreatic trypsin inhibitor (BPTI), a human amyloid precursor protein (APP), a human antithrombin III, a BP320 antigen, a human caspase-3, a hepatitis B surface antigen, a human sex steroid-binding protein (hSBP), a human endostatin, or a gp120.

Kits

Kits are also a feature of the invention. For example, kits can contain an unnatural amino acid and a methylotrophic yeast cell of the invention. The cell can optionally comprise a nucleic acid encoding an O-tRNA and/or a nucleic acid encoding an O-RS integrated into its genome, e.g., wherein the O-RS and O-tRNA are under the transcriptional control of any of the promoters recited previously. Kits can comprise components for using the cells herein, such as instructions to integrate a nucleic acid comprising one or more selector codon, which nucleic acid encodes a polypeptide of interest into the methylotrophic yeast cell's genome. The kit can include a container to hold the kit components, instructional materials for practicing any method herein with the cells provided with the kit, e.g., for producing a polypeptide of interest comprising one or more unnatural amino acid at a selected position.

EXAMPLES

The following examples are offered to illustrate, but not to limit the claimed invention. It is understood that the examples and embodiments described herein are for illustrative purposes only and that various modifications or changes in light thereof will be suggested to persons skilled in the art and are to be included within the spirit and purview of this application and scope of the appended claims.

Example 1

Construction of a *Pichia pastoris* Expression System for Proteins Comprising Unnatural Amino Acids The incorporation of an unnatural amino acid (UAA) into a polypeptide involves the addition of a "$21^{st}$" amino acid to the current repertoire of 20 natural proteinogenic alpha-amino acids through the evolution of genetically encoded, orthogonal tRNA$_{CUA}$ (O-tRNA)/orthogonal aminoacyl tRNA synthetase (O-RS) pairs. Directed evolution is employed to alter the specificity of the *M. jannaschii* tyrRS from tyrosine to the unnatural amino acid of interest for use as an O-RS in an *E. coli* expression system. Similarly, the specificities the *E. coli* tyrRS or leuRS can be altered from tyrosine or leucine, respectively, to the unnatural amino acids of interest for use as O-RSes in an *S. cerevisiae* expression system. Via semi-rational design of mutant libraries, over 30 aminoacyl-tRNA synthetases have been successfully evolved for their corresponding unnatural amino acids in *S. cerevisiae* and *E. coli* (Xie, et al. (2005) "An expanding genetic code." *Methods* 36: 227-38; Xie, et al. (2006) "A chemical toolkit for proteins: an expanded genetic code." *Nat Rev Mol Cell Biol* 7: 775-82). This in vivo, site-directed methodology has allowed the incorporation of novel chemical functionalities into proteins that surpasses the efficiency of chemical tRNA aminoacylation or solid phase synthesis. To date, unique chemical reactivities have included photolabile groups, glycosylated amino acids, photocrosslinkers, ketone functionalities, metal chelators, and IR probes (Xie, et al. (2005) "An expanding genetic code." *Methods* 36: 227-38; Wang, et al. (2006) "Expanding the genetic code." *Annu Rev Biophys Biomolec Struct* 35: 225-249). Of interest to this research are the unique ketone residue, p-acetylphenylalanine and azide residue, p-azidophenylalanine (Zhang, et al. (2003) "A new strategy for the site-specific modification of proteins in vivo." *Biochemistry* 42: 6735-46). Incorporation of these residues into proteins allows site-specific conjugation of small molecules, peptides, or polyethylene glycol (PEG), e.g., via oxime or hydrazide ligation.

Thus far, in vivo expression of proteins comprising unnatural amino acids using evolved orthogonal synthetases has been described in *E. coli, S. cerevisiae*, and mammalian cells (Lie, et al. (2007) "The genetic incorporation of unnatural amino acids into proteins in mammalian cells." *Nature Methods* 4: 239-244). Though many recombinantly expressed proteins comprising unnatural amino acids can be produced in such *E. coli* and *S. cerevisiae* expression systems, these systems are unable to synthesize sulfated proteins, glycosylated proteins, or proteins comprising complex disulfide crosslinks, e.g., human serum albumin (HSA) and human neutral endopeptidase, or Neprilysin (NEP). Because both HSA and NEP contain complex disulfide linkages, and because glycosylation is required for the production of biologically active NEP, neither of these proteins can be expressed in high yields in either *E. coli* or *S. cerevisiae*.

To express HSA or NEP variants comprising unnatural amino acids, a novel in vivo UAA expression system must be tailored for improved heterologous protein expression. For example, it has been repeatedly demonstrated that *Pichia pastoris* expression systems can successfully synthesize sulfated, glycosylated, or highly crosslinked mammalian proteins (Lin-Cereghino, et al. (2000) "Heterologous protein expression in the methylotrophic yeast *Pichia pastoris*." *FEMS Microbiol Rev* 24: 45-66). In contrast to proteins produced in *S. cerevisiae*, proteins produced in *P. pastoris* are less likely to contain high-mannose glycan structures that can hamper downstream processing, nor do proteins produced in *P. pastoris* contain potentially antigenic α1,3 glycan linkages. In addition, the expression levels of recombinant proteins in *P. pastoris* can be several orders of magnitude higher than expression levels in *S. cerevisiae* (Lin-Cereghino, et al. (2000) "Heterologous protein expression in the methylotrophic yeast *Pichia pastoris*." *FEMS Microbiol Rev* 24: 45-66). The transfer of evolved UAA synthetases from *S. cerevisiae* to *P. pastoris* can enhance the expression of functional mammalian proteins, such as HSA and NEP, comprising unnatural amino acids.

Due to the relative instability of plasmids in *P. pastoris*, DNA constructs encoding the protein of interest, e.g., human serum albumin (HSA), and the O-RS and O-tRNA, e.g., acetyl phenylalanyl tRNA synthetase (pApaRS) and tRNA$_{CUA}$, respectively, were each recombined into the *Pichia pastoris* genome as described in the Multi-copy *Pichia* Expression Kit (Invitrogen) and elsewhere (Lin-Cereghino, et al. (2000) "Heterologous protein expression in the methylotrophic yeast *Pichia pastoris*." *FEMS Microbiol Rev* 24: 45-66). The constructs were introduced into the genome of the *Pichia pastoris* strain GS200, a kind gift from the James Cregg laboratory. GS200 is unable to grow in media lacking arginine and histidine. The HSA construct, which comprises a HIS4 gene, was integrated into the GS200 genome at the AOX1 locus, and the construct encoding the O-RS and O-tRNA, which comprises the ARG4 gene, was integrated into GS200 at the ARG4 locus.

Genomic integration of the HSA mutant HSA-Glu37TAG was carried out via two methods: aox1::HSA gene replacement, and 5' AOX1 gene insertion. This mutant was chosen for expression in *Pichia pastoris* because the unnatural amino acid incorporated into the mutant protein, e.g., in response to the selector codon TAG, would be solvent accessible in the primary helix of the HSA protein, thus permitting subsequent in vitro conjugation reactions. The nucleotide sequence of wild type HSA (WT HSA) was obtained from the National Institutes of Health, Mammalian Gene Collection (accession number BC023034) and cloned into a pYES2.1 vector in preparation for generating the aforementioned mutant, which was made according to methods described in the QuikChange® Site-Directed Mutagenesis Kit (Stratagene). The mutant HSA allele and WT HSA were each re-cloned into pPIC3.5k between the BamHI and EcoRI restrictions sites, placing both WT and mutant HSA expression under the transcriptional control of the AOX1 promoter and terminator (FIG. 1). The 24 amino acid mammalian "pre-pro" leader sequence, e.g., amino acid sequence MKWVTFISLLFLFSSAYSRGVFRR, of HSA is compatible with *P. pastoris* secretory signals and allows export of the protein into the media. This pre-pro sequence is not present on mature HSA (Yeh, et al. (1992) "Design of Yeast-Secreted Albumin Derivatives for Human Therapy: Biological and Antiviral Properties of a Serum Albumin-CD4 Genetic Conjugate." *Proc Natl Acad Sci USA* 89: 1904-8).

The pPIC3.5k-HSA constructs, each of which encode HIS4 and a Geneticin®$^R$ (Gen$^R$) marker, were linearized with either SacI, to direct insertion into the 5' AOX1 locus, yielding GS200 transformants with a Gen$^R$ His$^+$ arg$^-$ Mut$^+$ phenotype, or BglII, to direct aox1::HSA gene replacement, yielding GS200 transformants with a Gen$^R$ His$^+$ arg$^-$ mut$^s$ phenotype. The resulting fragments were used to transform competent GS200 cells via electroporation. Yeast cells were made electrocompetent using standard methods described in the Multi-copy *Pichia* Expression Kit (Invitrogen) and elsewhere (see, e.g., Sears, et al. (1998) "A Versatile Set of Vectors for Constitutive and Regulated Gene Expression in *Pichia pastoris*." *Yeast* 14: 783-790 and Becker, et al. (1991) "High Efficiency Transformation of yeast by electroporation." *Methods Enzymol* Ed. Jon Abelson, et al. 194: 182-187.) *Pichia pastoris* transformants carrying pPIC3.5k-HSA cassettes in their genomes were selected for histidine prototrophy on regeneration dextrose base (RDB) agar plates lacking histidine. The transformants were then screened for Geneticin® resistance on yeast extract peptone dextrose (YPD) agar plates supplemented with 0.25 to 4.0 mg/mL Geneticin®. Transformants arising from aox1::HSA gene replacement grew on YPD plates supplemented with 0.25 mg/mL Geneticin®, indicating one copy of the HSA-Glu27TAG cassette was present in the genome, whereas transformants arising from 5' AOX1 insertion grew on YPD plates containing 2.5 mg/mL Geneticin®, indicating multiple copies of the HSA-Glu27TAG cassette were present in the genome. One HSA-Glu37TAG transformant arising from aox1::HSA gene replacement and one HSA-Glu37TAG transformant arising from 5' AOX1 insertion were picked and made electrocompetent. A GS200 clone carrying one copy of WT HSA (mut$^s$ arg$^-$ phenotype) was frozen for use as an expression control.

Figure 2:
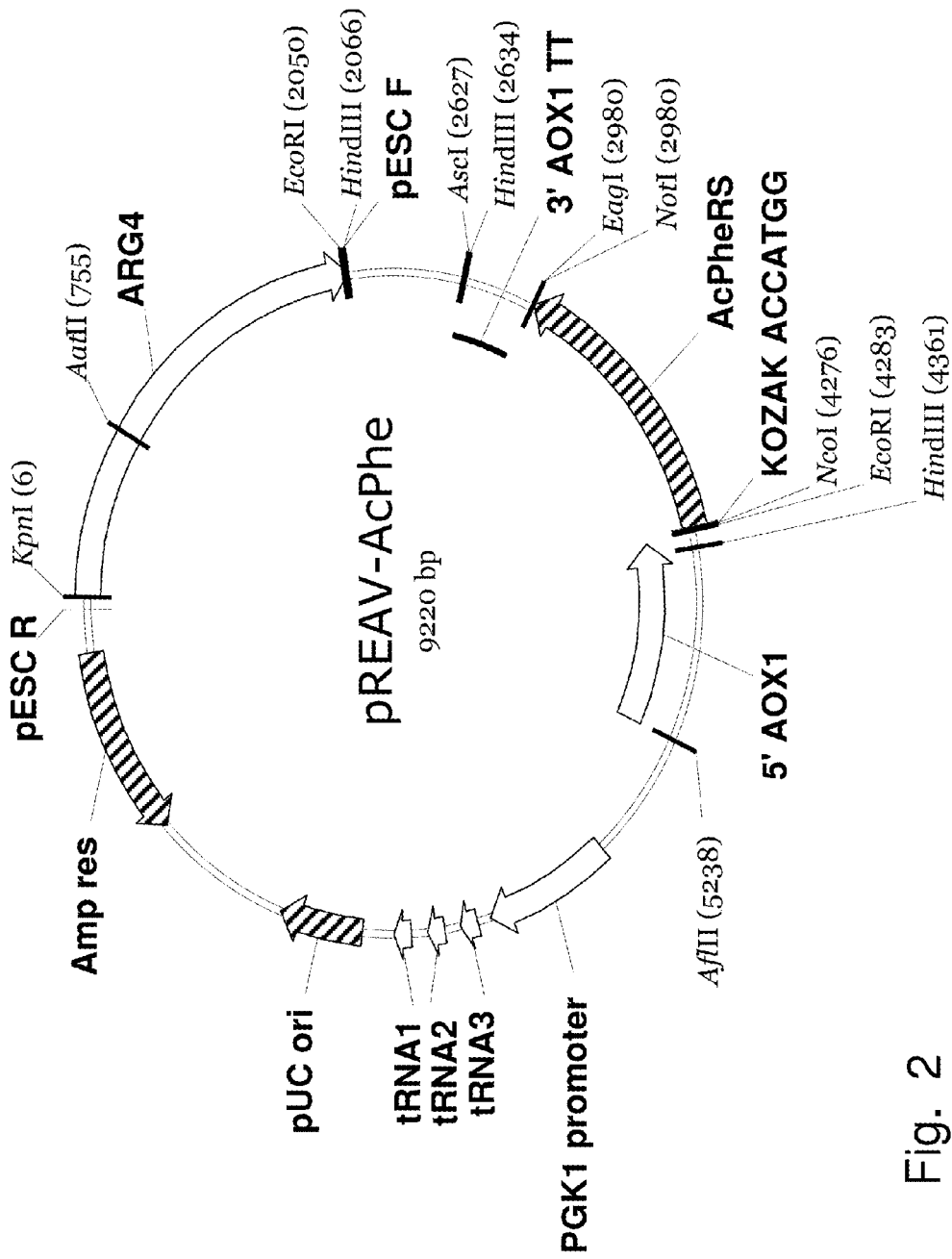
FIG. 2 depicts the plasmid that was constructed in preparation to integrate the gene encoding p-acetylphenylalanyl-tRNA synthetase (pApaRS) and a polynucleotide comprising three copies of $tRNA_{CUA}$ into the *Pichia pastoris* genome.

Plasmid pREAV was constructed from pPR1-PGK1+3SUP4-tRNA$_{CUA}$, an optimized *S. cerevisiae* expression plasmid from the Peter Schultz laboratory, to contain inserts encoding p-acetylphenylalanyl tRNA synthetase (pApaRS) and tRNA$_{CUA}$ (FIG. 2). This orthogonal aminoacyl-tRNA synthetase/orthogonal tRNA pair was derived from *Escherichia coli* and previously optimized to incorporate the unnatural amino acid p-acetylphenylalanine in an *S. cerevisiae* expression system (Chen, S. et al. (2007) "An Improved System for the Generation and Analysis of Mutant Proteins Containing Unnatural Amino Acids in *Saccharomyces cerevisiae.*" *Journal Molec Bio* 371: 112-22).

pPR1-PGK1+3SUP4ARNA$_{CUA}$ encodes three tandem copies of tRNA$_{CUA}$. To construct pREAV, PCR was performed using the pPR1-PGK1+3SUP4-tRNA$_{CUA}$ vector as a template to produce a pPR1-derived plasmid containing the restriction sites KpnI and HindIII positioned just outside of the region on the vector encoding the 2u origin and TRP marker. ARG4 (accession number AF321097) was amplified from plasmid pBLARG, a gift from the James Cregg laboratory, via PCR to generate a fragment encoding ARG4 flanked by KpnI and HindIII restriction sites. The KpnI/HindIII ARG4 fragment was ligated into the pPR1-derived vector described above, replacing the 2u origin and TRP marker. AflII and AscI restriction sites were then introduced into this construct outside of the ADH1 promoter via PCR. A NotI/EcoRI insert encoding pApaRS was cloned into a pPIC3.5K plasmid that was linearized via NotI and EcoRI digestion, placing pApaRS expression under the transcriptional control of the AOX1 promoter and terminator. A fragment comprising the AOX1 promoter, the gene encoding pApaRS, and the AOX1 transcriptional terminator was amplified from this pPIC3.5K-derived construct to generate a PAOX1-pApaRS-TAOX1 fragment flanked by AflII and AscI restriction sites. This fragment was ligated into an AflII/AscI digested pPR1-derivative described above to generate pREAV-pApaRS (FIG. 2). The final pREAV-pApaRS construct comprises an *E. coli* pUC ori, places the gene encoding pApaRS under the control of the AOX1 promoter and transcriptional terminator, and places bla, e.g., the gene encoding β-lactamase, ARG4 and the three copies of tRNA$_{CUA}$ under the transcriptional control of the PGK1 promoter (FIG. 2).

pREAV-pApaRS was then linearized via AatII digestion, and the linearized construct was used to transform the two previously isolated electrocompetent GS200 strains carrying mutant HSA alleles. Transformants were selected for arginine prototrophy on RDB plates lacking arginine, and rescreened for Geneticin® resistance on YPD plates supplemented with 0-2.5 mg/mL Geneticin®, as described above. These strains were then used in subsequent experiments described below to monitor HSA expression levels and the incorporation of unnatural amino acid pApa into mutant HSA proteins in *Pichia pastoris*.

Figure 3:
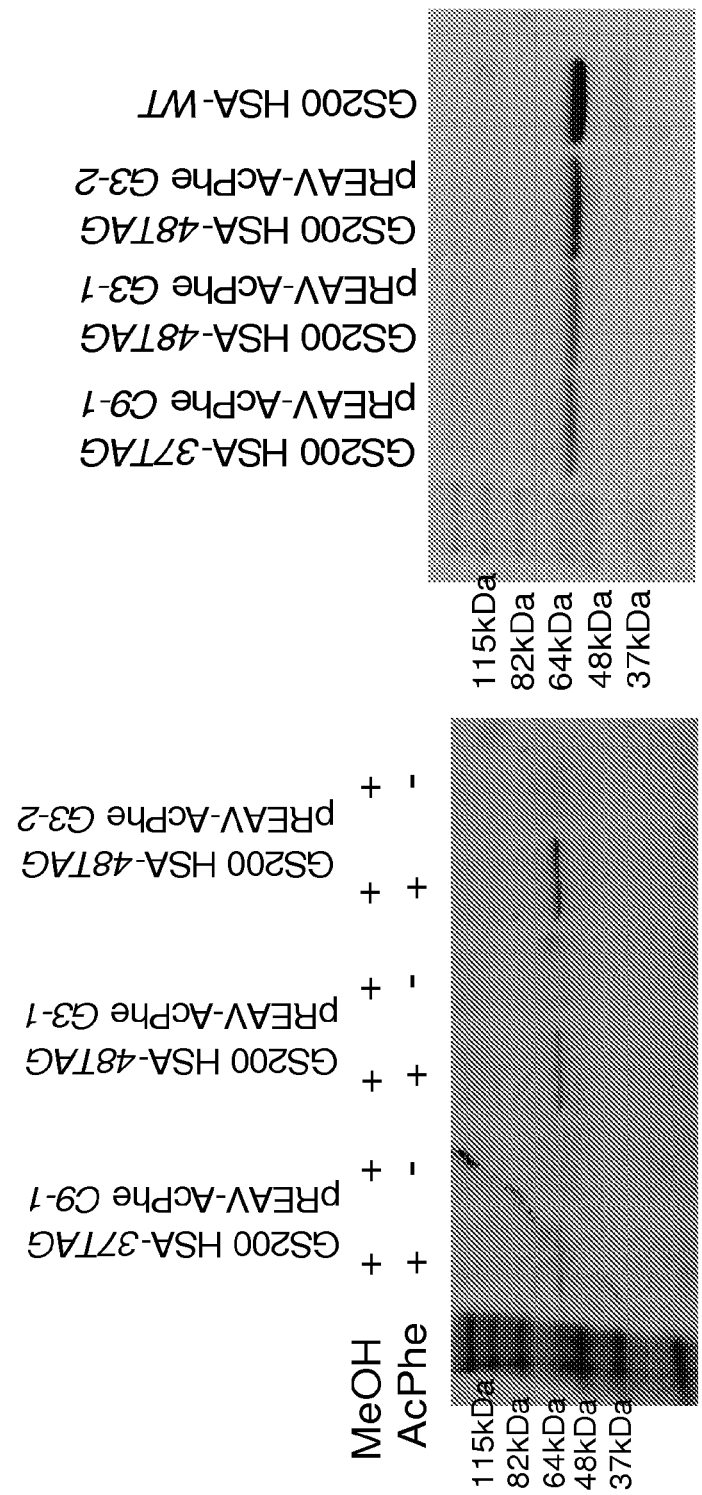
FIG. 3 illustrates the results of experiments performed under methanol induction conditions to monitor the expression of HSA in *Pichia pastoris* strains expressing p-acetylphenylalanyl-tRNA synthetase (pApaRS) and $tRNA_{CUA}$.

The transformants, e.g., 20 Mut$^+$ isolates and 20 mut$^s$ isolates, were grown under methanol induction conditions for 120-144 hours. One GS200 HSA-37TAG pREAV-pApaRS mut$^s$ isolate and one GS200 HSA-37TAG pREAV-pApaRS Mut$^+$ isolate were chosen for further analysis because each was found to express high levels of mutant HSA, indicating amber suppression of the selector codon encoded in the HSA allele by the O-tRNA. HSA expression was monitored by gel electrophoresis of 20 ul samples of centrifuged media on a denaturing polyacrylamide gel (SDS-PAGE). HSA expression was observed only in the presence of the unnatural amino acid p-acetylphenylalanine (pApa), as visualized on the Coomassie-stained polyacrylamide gel on which the samples were run (FIG. 3). Protein yields from the mut$^s$ isolate were approximately 10-12 mg/ml and yields from the Mut$^+$ isolate were 10-15 mg/ml.

These experiments were repeated with strains constructed to incorporate the unnatural amino acid p-azidophenylalanine (pAzpa) into proteins in response to a selector codon. A previously described p-azidophenylalanine synthetase (pAzpaRS), derived from *Escherichia coli* and previously optimized to incorporate the unnatural amino acid pAzpa in an *S. cerevisiae* expression system (Chen, S. et al. (2007) "An Improved System for the Generation and Analysis of Mutant Proteins Containing Unnatural Amino Acids in *Saccharomyces cerevisiae.*" *Journal Molec Bio* 371: 112-22), was cloned into pREAV that had been digested with EagI and NcoI. This construct was linearized with AatII, as previously described, and transformed into the GS200 HSA-37TAG Mut$^+$ strain. The resulting transformants were analyzed as described above, and a single GS200 HSA-37TAG pREAV-pAzpaRS Mut$^+$ isolate was chosen for use in further experiments because it was found to express high levels of HSA comprising the unnatural amino acid pAzpa. This isolate only expressed the mutant HSA protein in media supplemented with pAzpa.

To confirm incorporation of the unnatural amino acid pApa into HSA, preparations were made to increase the scale of HSA expression using methods described in the Multi-copy *Pichia* Expression Kit (Invitrogen) that were slightly modified. Briefly, one colony of the GS200 HSA-37TAG pREAV-pApaRS Mut$^+$ and one colony of GS200 HSA-WT pREAV-pApaRS were each independently grown to near saturation in liquid YPD media. These two cultures were used to inoculate 1 L each of buffered media glycerol yeast extract (BMGY) and grown, while shaking, at 29-30° C. After 16-20 hrs, the cultures had each reached an optical density (OD$_{600}$) of approximately 8.0, and they were centrifuged at 1500×g for 5 minutes. The cell pellets were resuspended in 200 mL of a 1:9 ratio of buffered complex methanol media (BMMY):buffered minimal methanol (BMM). Methanol was added to the 1:9 BMMY:BMM to a final concentration of 0.5% every 24 hours to maintain induction. One 20 ul aliquot was collected from both cultures every 24 hours for 144 hours. The samples collected from the time course were centrifuged to pellet cells, and the supernatants were run on an SDS denaturing polyacrylamide gel for analysis of protein content. After 3 days of methanol induction in a *Pichia pastoris* expression system, a band corresponding to the molecular weight of HSA is generally visible on a Coomassie-stained polyacrylamide gel. After 5 days of methanol induction, the titers of HSA expressed from the strain GS200 HSA-37TAG pREAV-pApaRS Mut$^+$ reached 10-12 mg/L, compared to 25-30 mg/L for wild type HSA, as visualized on the Coomassie-stained SDS-PAGE on which the samples were run.

The mutant HSA protein comprising pApa, as expressed by GS200 HSA-37TAG pREAV-pApaRS Mut$^+$, and WT HSA protein were purified using standard purification techniques (see, e.g., Sumi, et al. (1999) "Purification of recombinant human serum albumin: efficient purification using STREAMLINE." *Bioseparation* 8: 195-200; Wantanabe, et al. (2001) "In vitro and in vivo properties of recombinant human serum albumin from *Pichia pastoris* purified by a method of short processing time." *Pharm Res* 18: 1775-1781). Briefly, the GS200 HSA-37TAG pREAV-pApaRS Mut$^+$ and GS200 HSA-wt pREAV-pApaRS cultures were centrifuged at 3000×g for 10 minutes. The supernatants of each culture were recovered and protein was precipitated from each by the addition of ammonium sulfate to 80%, followed by centrifugation at 10,000×g for 20 minutes. The resulting pellets were resolubilized in Buffer A (25 mM Tris-HCl, 25 mM NaCl, 1 mM EDTA pH=8.5)+Roche Complete™ Protease Inhibitor Cocktail, dialyzed overnight against Buffer A+Roche Complete™ Protease Inhibitor Cocktail, and purified on a MonoQ anion exchange column via FPLC. Fractions were eluted using a linear gradient of 0-80% Buffer B (Buffer A+1M NaCl) and analyzed on an SDS PAGE for the presence of HSA. Fractions eluted between 20% and 30% Buffer B were found to contain HSA, were dialyzed to PBS (pH=7.6) and further purified on a size exclusion column. Fractions were collected during purification on the size exclusion column and analyzed via SDS PAGE for the presence of HSA. Those fractions eluted between 13 ml and 15.5 ml PBS (pH=7.6) were found to contain HSA and were concentrated and purified on a C8 reverse phase HPLC column. Fractions were eluted using a linear gradient of 40-46% Acetonitrile in water, 0.1% trifluoroacetic acid, collected, and analyzed on an SDS PAGE for the presence of HSA. Those fractions eluted form the C8 column with 42-45% Acetonitrile in water, 0.1% trifluoroacetic acid were found to contain HSA.

Figure 4:
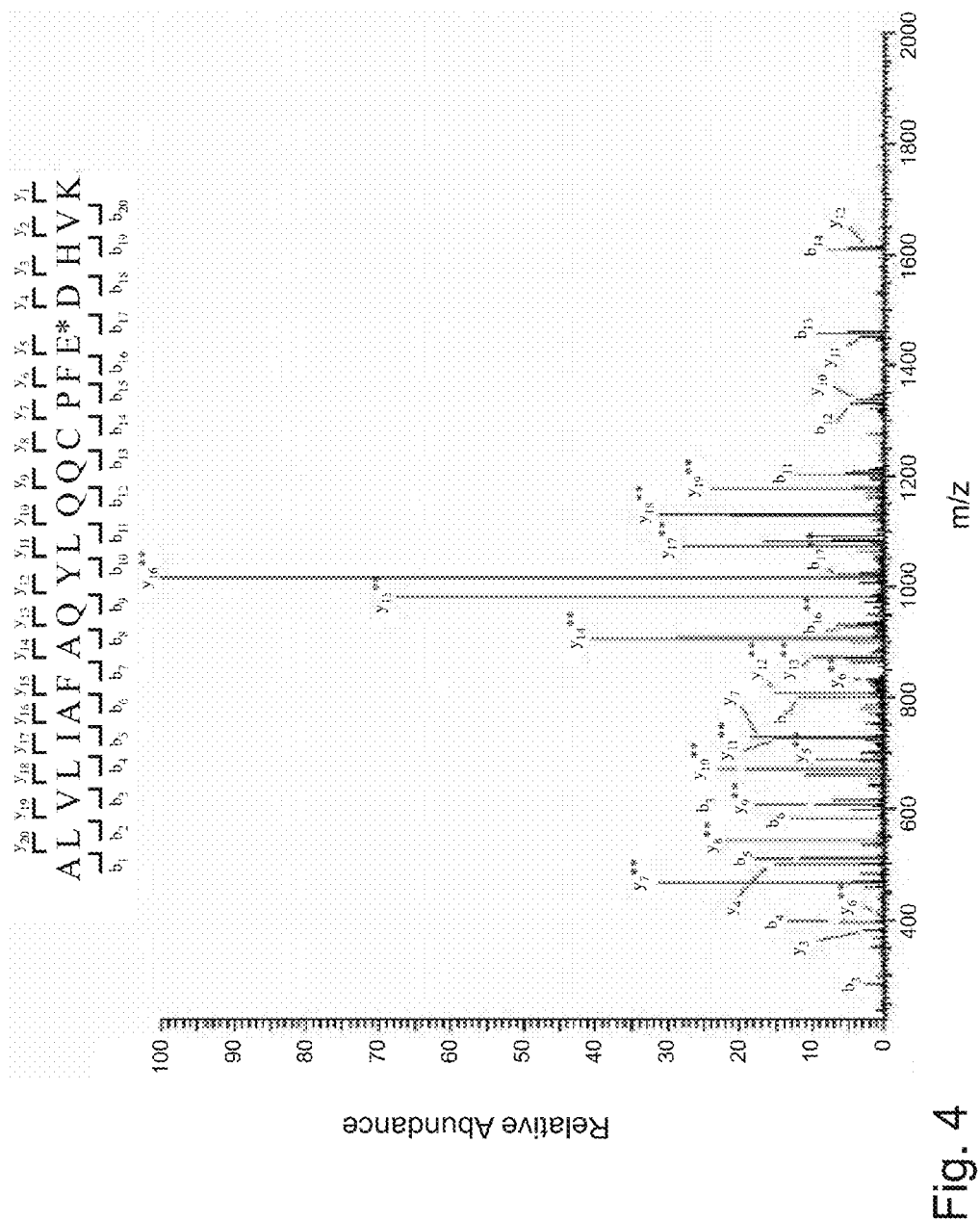
FIG. 4 illustrates the results of liquid chromatography-tandem mass spectrometry experiments performed to confirm the incorporation of the unnatural amino acid p-acetylphenylalanine (pApa) into HSA.

To confirm incorporation of pApa into HSA expressed by GS200 HSA-37TAG pREAV-pApaRS Mut$^+$, the protein was analyzed via tryptic digest followed by liquid chromatography-tandem mass spectrometry (LC-MS/MS). The results of LC-MS/MS analysis are shown in FIG. 4. FIG. 4 depicts the partially annotated tandem mass spectrum of the triply charged precursor ion (m/z=847.765) of the peracetic oxidized peptide ALVLIAFAQYLQQCPFEDHVK. E* denotes substitution of E37 in mature HSA by the pApa. The substitution is supported without ambiguity by the observed fragment ion series.

Figure 5:
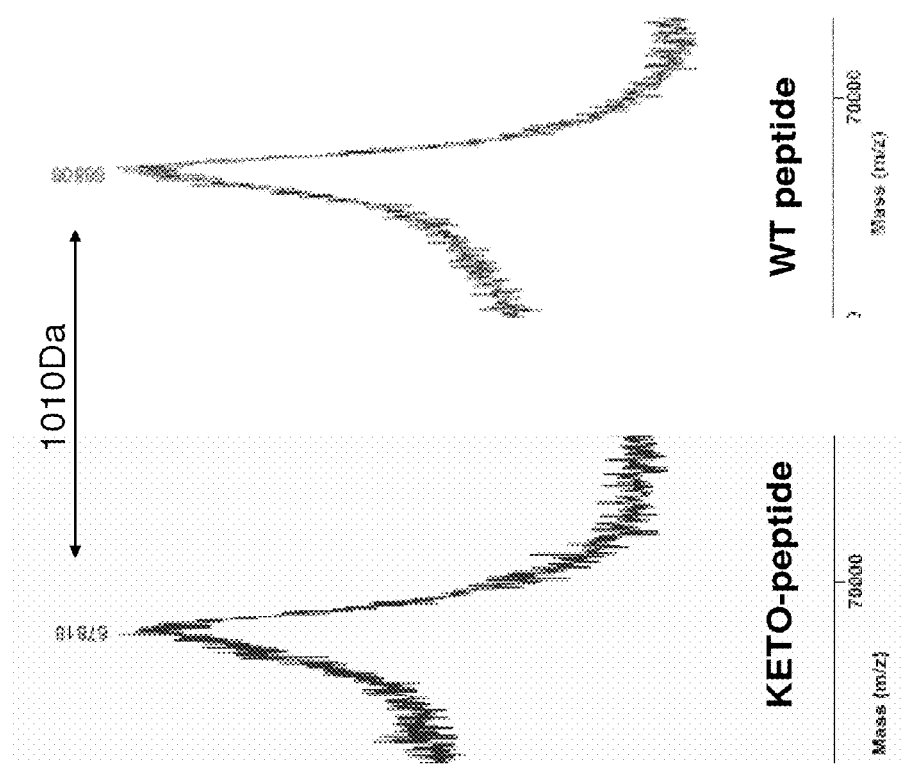
FIG. 5 illustrates the results of MALDI mass spectrometry analysis performed to confirm the incorporation of p-acetylphenylalanine (pApa) into HSA.

Additional experiments were performed to confirm the incorporation of pApa into the HSA expressed by GS200 HSA-37TAG pREAV-pApaRS Mut$^+$. The WT HSA and HSA comprising pApa at amino acid position 37 were each incubated in 150 mM NaCl, 50 mM NaOAc (pH=4.7) in the presence of a 1.1 kDa peptide that comprises an aminoxy group. The samples were then purified on a C8 reverse phase HPLC column, as described above, to remove any unreacted 1.1 kDa peptide and analyzed via matrix assisted laser desorption ionization (MALDI) mass spectrometry. At pH=4.7, aminoxy groups are known to undergo orthogonal ligation with ketones to form oxime ligations (Dirksen, et al. (2006) "Nucleophilic catalysis of oxime ligation." Angew Chem Int Ed Engl 45: 7581-4). Thus, only the mutant HSA protein comprising pApa at amino acid position 37, e.g., a solvent accessible keto group at amino acid position 37, was expected to form oxime ligations with the aforementioned 1.1 kDa peptide. Results from MALDI analysis indicate that only the HSA comprising pApa exhibits an increase in mass of approximately 1 kDa (FIG. 5). In contrast, the mass of the WT HSA remained unchanged, giving further confirmation of the site-specific incorporation of the unnatural amino acid pApa into the mutant HSA protein.

Example 2

Expanding the Genetic Repertoire of the Methylotrophic Yeast, Pichia pastoris

To increase the utility of protein mutagenesis with unnatural amino acids, a recombinant expression system in the methylotrophic yeast Pichia pastoris was developed. Aminoacyl-tRNA synthetase/suppressor tRNA (aaRS/tRNA$_{CUA}$) pairs specific for eight unnatural amino acids were inserted between eukaryotic transcriptional control elements and stably incorporated into the P. pastoris genome. Yields of mutant protein from the methylotrophic yeast were greater than 150 mg l$^{-1}$—more than an order of magnitude better than that reported in S. cerevisiae. Moreover, we show that a human serum albumin mutant containing a keto amino acid (p-acetylphenylalanine, FIG. 11, Structure 1) can be efficiently expressed in this system and selectively conjugated to a thrombospondin peptide mimetic in high yield. This methodology should allow the production of high yields of complex proteins with unnatural amino acids whose expression is not practical in existing systems.

Recently, we developed methodology that makes it possible to genetically encode a wide variety of unnatural amino acids with novel properties (including fluorophores, metal ion chelators, photocaged and photocrosslinking groups, NMR, crystallographic and IR probes, and post-translationally modified amino acids) in both prokaryotic and eukaryotic organisms[1-3]. This is accomplished through the evolution of an orthogonal aminoacyl-tRNA synthetase/suppressor tRNA (aaRS/tRNA$_{CUA}$) pair, designed to selectively insert a desired unnatural amino acid in response to a nonsense or frameshift codon. Thus far, this methodology has been employed to add more than 40 unnatural amino acids to the genetic repertoires of Escherichia coli, Saccharomyces cerevisiae, and several lines of mammalian cells[1,2,4]. Orthogonality in these systems is achieved by transplanting an orthogonal aaRS/tRNA$_{CUA}$ pair with distinct tRNA identity elements into the host organism such that no cross-aminoacylation occurs between the host aminoacylation machinery and the transplanted aaRS/tRNA pair (while still maintaining function in translation). In the current systems, this has proven most successful using aaRS/tRNA$_{CUA}$ pairs derived from the Methanococcus jannaschii tyrosyl-RS/tRNA$_{CUA}$ pair in E. colic and the E. coli tyrosyl- or leucyl-RS/tRNA$_{CUA}$ pairs in S. cerevisiae[2,6] or mammalian cells[4]. Directed evolution is then used to alter the specificity of the orthogonal aaRS so that it recognizes the unnatural amino acid of interest and not one of the common twenty amino acids.

To expand this methodology for the production of large quantities of proteins that are not easily expressed in bacterial hosts, a recombinant system is desired with low cost, scalability, and the ability to produce complex, post-translationally modified proteins. One such host is Pichia pastoris, which is capable of producing mammalian proteins in yields comparable to those of E. coli[7]. Therapeutic proteins such as tumor necrosis factor (TNF), tetanus toxin fragment C (TTC), and human serum albumin (HSA) have afforded expression levels >10 g l$^{-1}$ in high density fermentations[8-11]. P. pastoris' ability to produce proteins in such yields is attributed to its alcohol oxidase 1 promoter (P$_{AOX1}$), one of the most highly regulated and strongest promoters known[12]. In addition, P. pastoris lacks endotoxins which can contaminate therapeutic proteins expressed in E. coli, and does not produce antigenic α1,3 glycan linkages as does S. cerevisiae[13]. Additionally, it is now possible to modulate glycosylation patterns in P. pastoris, including control of silyation, an important sugar linkage in anti-inflammatory antibodies[14]. For these reasons, we undertook the development of methodology to allow unnatural amino acids to be genetically encoded in P. pastoris. Here we report that eight unnatural amino acids were site-specifically introduced into recombinant human serum albumin (rHSA) expressed in this host with high yields and fidelities.

Results

Design of a Two Gene Cassette Expression System.

Due to the relative instability of autonomously replicating plasmids in P. pastoris[15], a system was devised in which the target gene of interest and the aaRS/tRNA$_{CUA}$ pair were encoded in cassettes on two separate plasmids, and stably integrated into the genome. The double auxotroph, GS200 (arg4, his4) was used as the host strain for protein expression, and the gene of interest was inserted into the commercially available pPIC3.5k plasmid (HIS4, Gen$^R$) (FIG. 6a)[16]. rHSA was used as a model protein given its utility in producing fusion proteins or peptide bioconjugates that enhance the serum half-life of short lived therapeutic polypeptides[17-19]. Expression of rHSA in *E. coli* and *S. cerevisiae* is not practical due to the protein's complex disulfide crosslinkages. A Glu37TAG mutant rHSA (rHSA$_{E37X}$) was generated by PCR mutagenesis, and expressed under the AOX1 promoter and terminator to create pPIC3.5k-rHSA$_{E37X}$. Glu37 is in a solvent accessible helix which should facilitate the conjugation of peptides to a chemically reactive unnatural amino acid (i.e., p-acetylphenylalanine, FIG. 11, Structure 1) introduced at this site, and ensure that incorporation of relatively bulky groups minimally disrupt native protein structure and folding. The 24 amino acid mammalian "pre-pro" leader sequence of HSA (FIG. 6e) is fully compatible with expression in *P. pastoris* and allows export of the mature protein into the media[20]. As a positive control for protein expression, wild type rHSA (rHSA$_{WT}$) was used to create pPIC3.5k-HSA$_{WT}$ in a similar fashion. Linearization of this plasmid in the 5' AOX1 promoter allows genomic integration of one or more copies of the cassette; generally more copies result in higher overall yields of target protein[21]. Integration in this manner leaves the AOX1 gene intact, retaining the yeast's ability to rapidly utilize methanol (Mut$^+$ phenotype). Alternatively, gene replacement can be carried out by linearization on either side of AOX1 cassette, resulting in replacement of the AOX1 gene by the pPIC3.5k vector[16]. Yeast lacking AOX1 rely on the weaker AOX2 gene for methanol utilization and are phenotypically mut$^s$. Because expression of rHSA is commonly carried out with mut$^s$ yeast[22], pPIC3.5k-HSA$_{E37X}$ was linearized and used to replace the AOX1 gene to yield GS200-rHSA$_{E37X}$ (HIS4, arg4, Gen$^R$, mut$^s$). Successful transformants grew normally on minimal media plates lacking histidine, and on rich media plates containing up to 0.25 mg ml$^{-1}$ of the aminoglycoside antibiotic Geneticin.

To integrate the orthogonal aaRS/tRNA$_{CUA}$ pair into the genome, the previously developed pPR1-P$_{PGK1}$+3SUP4-tRNA$_{CUA}^{Tyr}$ vector[23] (FIG. 6b) for recombinant over-expression in *S. cerevisiae* was modified. The p-acetylphenylalanine (pApa, FIG. 11, Structure 1) specific aminoacyl-tRNA synthetase (pApaRS), previously evolved in *S. cerevisiae*[24], was inserted between the alcohol dehydrogenase 1 promoter (P$_{ADH1}$) and terminator (T$_{ADH1}$) with a His$_6$-tag to assay its expression. The cognate *E. coli* tRNA$_{CUA}^{Tyr}$ lacking the 5' CCA was inserted as three tandem repeats behind the phosphoglycerate kinase 1 promoter (P$_{PGK1}$). To aid in posttranscriptional processing, the tRNAs were flanked by regions from the yeast suppressor tRNA gene, SUP4, as previously described[23]. Eukaryotic downstream processing adds the 5' CCA that is required for tRNA function. The 2μ origin and orotidine 5-phosphate decarboxylase (URA3) marker of pPR1-P$_{PGK1}$+3SUP4-tRNA$_{CUA}^{tyr}$ were replaced by the arginosuccinate lyase (ARG4) coding region to give the recombinant eukaryotic ARG4 vector (pREAV-P$_{ADH1}$-pApaRS) (FIG. 6c). Propagation of this cassette is only possible in the event of genomic incorporation since it lacks a eukaryotic origin of replication. Linearization of pREAV-P$_{ADH1}$-pApaRS in the ARG4 coding region, and subsequent transformation into GS200-HSA$_{E37X}$ gave the fully prototrophic *P. pastoris* GS200-HSA$_{E37X}$/pREAV-P$_{ADH1}$-pApaRS (HIS4, ARG4, Gen$^R$, mut$^s$). As a positive control, the pREAV-P$_{ADH1}$-pApaRS vector was similarly cloned into GS200-HSA$_{WT}$ to give a fully prototrophic, mut$^s$, rHSA$_{WT}$ expressing *P. pastoris* strain.

Amber Suppression in *P. pastoris*.

Figures 7A, 7B:
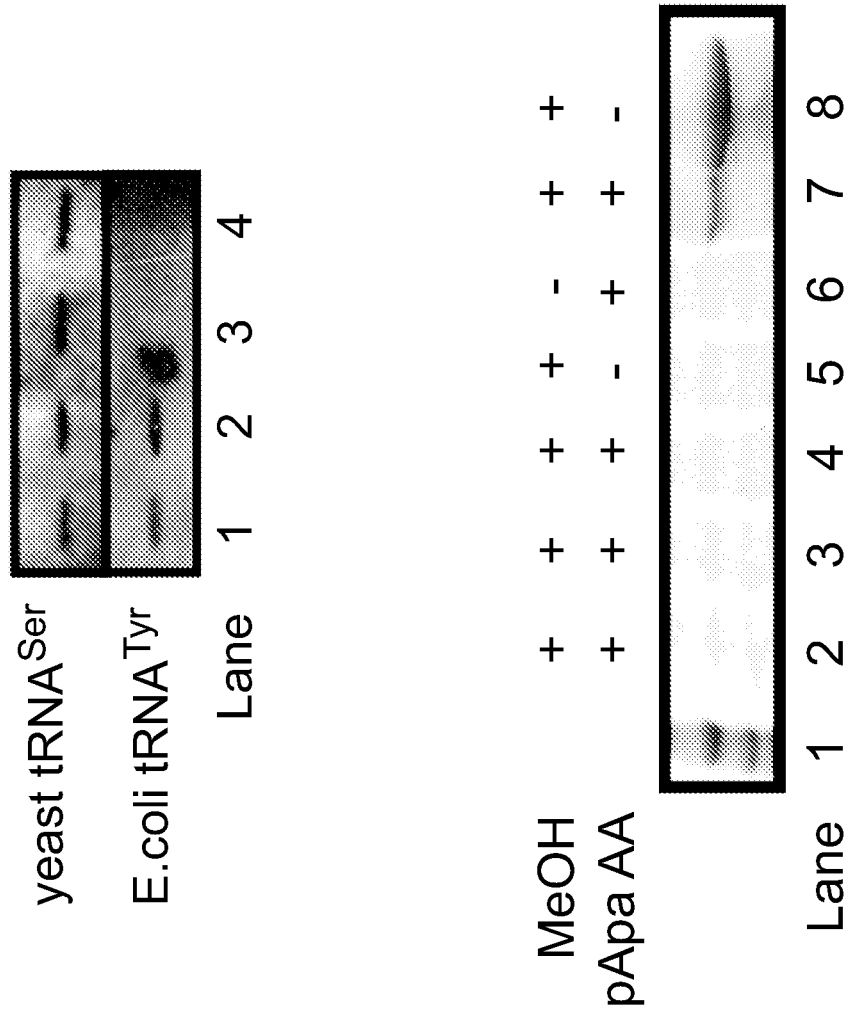
FIG. 7 shows the results of experiments that were performed to determine the fidelity and specificity with which the unnatural amino acid p-acetylphenylalanine is incorporated into HSA in response to a selector codon at amino acid position 37. Amber suppression with pApa in *P. pastoris*. (a) A Northern blot (bottom gel) was used to assay suppressor $tRNA_{CUA}^{Tyr}$ transcription in *S. cerevisiae*+pPR1-$P_{PGK1}$-3SUP4-tRNA (lane 1) and *P. pastoris*+pREAV-$P_{ADH1}$-pApaRS (lane 2). For a negative control, lanes 3 and 4 are *S. cerevisiae* and *P. pastoris* strains lacking vectors, respectively. The top gel shows a Northern blot for the endogenous serine tRNA and illustrates equal miRNA preparation in all samples. (b) To assay the fidelity of the system, 25 µl of cleared media from 6 days of growth was analyzed on a denaturing SDS-PAGE gel and stained with Coomassie. Lane 2 is GS200; lane 3 is GS200-HSA$_{E37X}$; lane 4 is GS200-pREAV-P$_{AOX1}$-pApaRS; lanes 5-7 are GS200-HSA$_{E37X}$/pREAV-P$_{AOX1}$-pApaRS; and lane 8 is GS200-HSA$_{WT}$/pREAV-P$_{ADH1}$-pApaRS. Amber suppression only occurs in yeast harboring both vectors, and grown with methanol and pApa amino acid (pApa AA). (c) MS/MS fragmentation of a tryptic peptide (top) containing the unnatural amino acid pApa (denoted E*) at residue 37 of mature rHSA$_{E37pApa}$. The substitution is supported without ambiguity by the observed fragment ion series. Sequence ions are labeled with standard nomenclature[44].
Figure 7C:
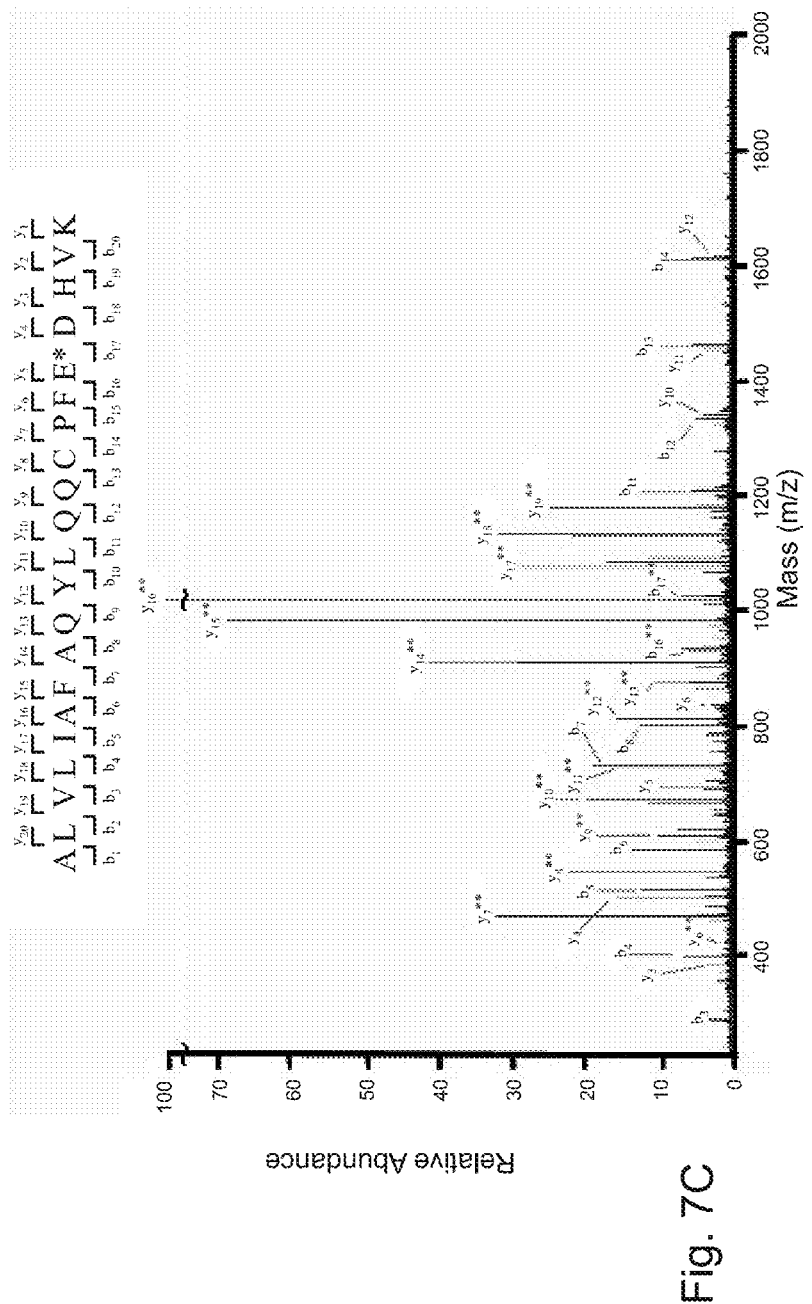
Figure 12:
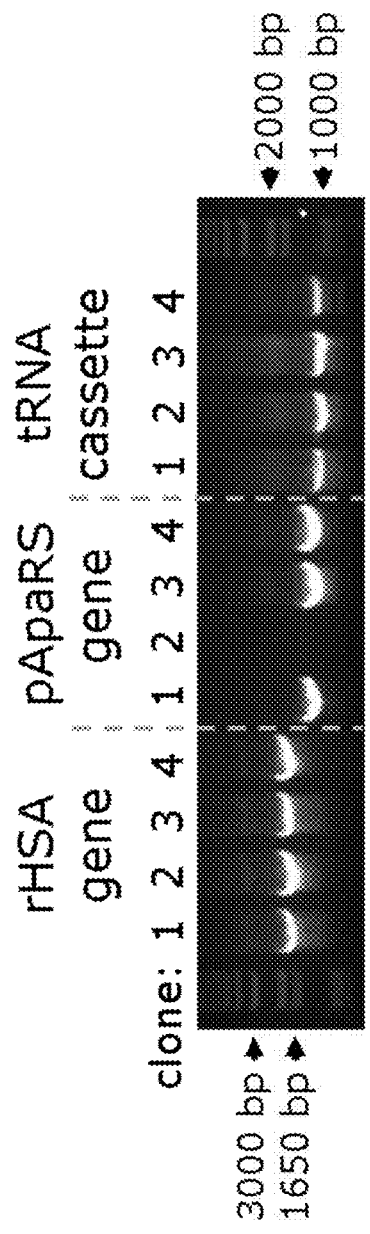
FIG. 12 depicts the results of PCR performed on 4 transformants to determine whether pPIC3.5k and pREAV cassettes were successfully incorporated into GS200-rHSA$_{E37X}$/pREAV-P$_{ADH1}$-pApaRS. 4 clones were chosen from one transformation and labeled 1-4. Expected PCR products were rHSA 1851 bp, pApaRS 1317 bp, and tRNA cassette 1100 bp. The lack of pApaRS amplification in clone 2 is likely a technical artifact.
Figure 13:
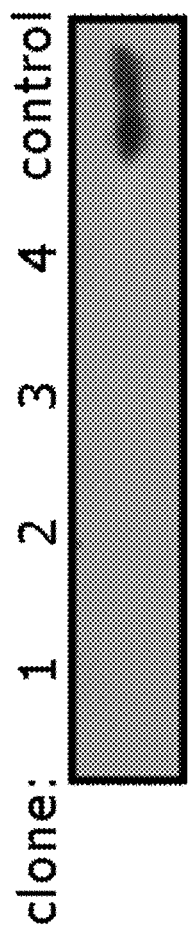
FIG. 13 depicts western blots for pApaRS-$_{His6x}$ in four separate clones of GS200-rHSA$_{E37X}$/pREAV-P$_{ADH1}$-pApaRS from a single transformation. No pApaRS protein was detectable.

Clones isolated from GS200-HSA$_{WT}$/pREAV-P$_{ADH1}$-pApaRS produced full length rHSA$_{WT}$ visible by Coomassie staining on a sodium dodecyl sulfate polyacrylamide gel-electrophoresis (SDS-PAGE) gel after two to three days when grown under methanol inducing conditions. In contrast, clones from GS200-HSA$_{E37X}$/pREAV-P$_{ADH1}$-pApaRS failed to produce full length rHSA$_{E37pApa}$ when grown for six days with methanol as the primary carbon source and pApa amino acid supplementation. Genomic integration of all constructs was confirmed by genomic PCR (FIG. 12), and transcription of the tRNA$_{CUA}$ was found to be approximately 1.5 times greater than the same cassette in *S. cerevisiae* by Northern blot analysis (FIG. 7a). However, no pApaRS was detectable by Western blot for the His$_{6x}$-tag (FIG. 13). These results indicated that the lack of amber suppression was linked to poor incorporation of the pApaRS. Therefore, pREAV was further modified to drive expression of pApaRS with the powerful P$_{AOX1}$ promoter, and an enhanced Kozak consensus sequence (ACCATGG)[25] was added to the 5' end of the pApaRS gene. The ADH1 terminator (T$_{ADH1}$) was also replaced by the AOX1 terminator (T$_{AOX1}$) to give pREAV-P$_{AOX1}$-pApaRS (FIG. 6d). Transformation into GS200-rHSA$_{E37X}$ yielded GS200-rHSA$_{E37X}$/pREAV-P$_{AOX1}$-pApaRS with the same phenotype as previously noted. Clones from this transformation produced full length rHSA$_{E37pApa}$ only in the presence of methanol and pApa amino acid, at levels approximately 10-20% of identical clones harboring rHSA$_{WT}$. Protein was visible by SDS-PAGE gel two to three days post methanol induction, and peaked six days after expression with methanol supplementation to 0.5% every 24 h (FIG. 7b). Yeast lacking the pREAV cassette, pPIC3.5k cassette, methanol supplementation, or pApa amino acid failed to produce protein detectable by Coomassie staining. The lack of protein expression in the absence of pApa amino acid indicates that no cross aminoacylation occurs between the pApaRS/tRNA$_{CUA}^{tyr}$ pair and the endogenous aminoacylation machinery. Site-specific incorporation of pApa into rHSA$_{E37X}$ was confirmed by tryptic digest, LC-MS/MS (FIG. 7c). The observed fragment ion shows that the unnatural amino acid was uniquely incorporated at residue 37.

Optimization of Expression.

Figure 8A:
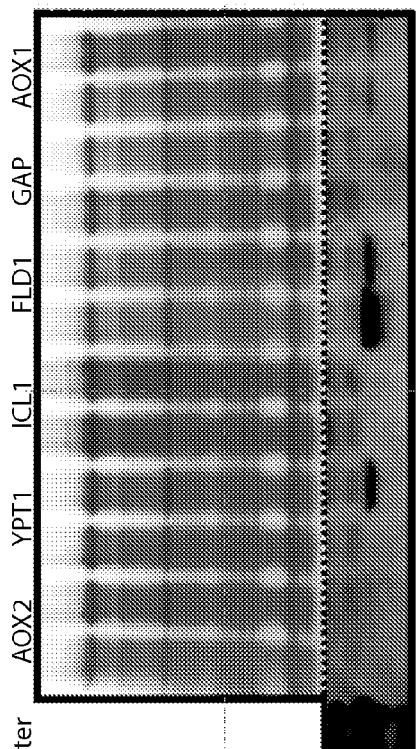
FIG. 8 shows the results of experiments that were performed to compare pApaRS promoters for optimized amber suppression. (a) Linear map of pREAV-P$_{Promoter}$-pApaRS illustrating the promoter region (green, red outline) being varied. Promoters were PCR amplified from genomic DNA (FIG. 12). (b) Two clones from each transformation of GS200-rHSA$_{E37X}$ with pREAV-P$_{Promoter}$-pApaRS were grown with methanol as the primary carbon source for 6 days, lysed, separated on an SDS-PAGE gel (top gel). The gel was stained with Coomassie to verify equal loading. Lysates were analyzed via Western blot for pApaRs-His$_{6x}$ (bottom gel). (c) The clones which produced most protein in b were analyzed by Northern blot for pApaRS mRNA transcription (bottom gel). Bands for the 18s and 28s ribosomal RNA were stained with ethidium bromide (top gel) confirm RNA integrity and equal loading. (d) Bar graph representation of b determined by density of stained band, averaging the duplicates. Error bars represent variance.
Figure 8B:
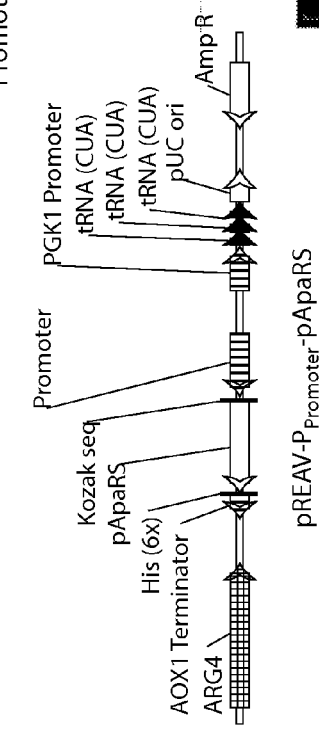
Figure 8C:
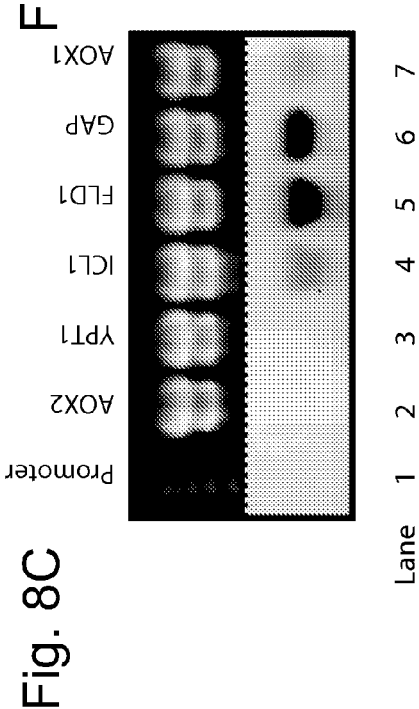
Figure 8D:
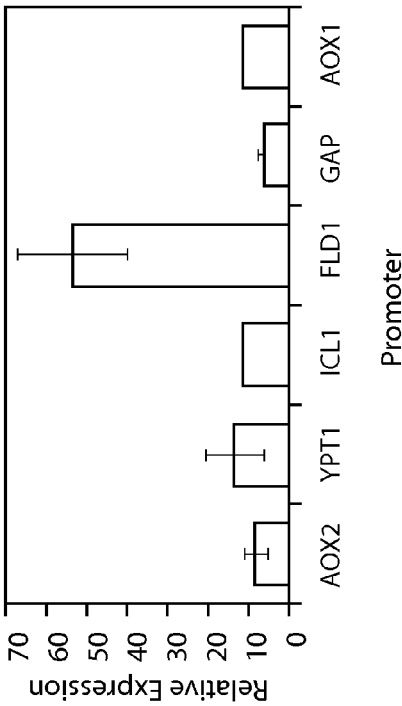
Figure 9:
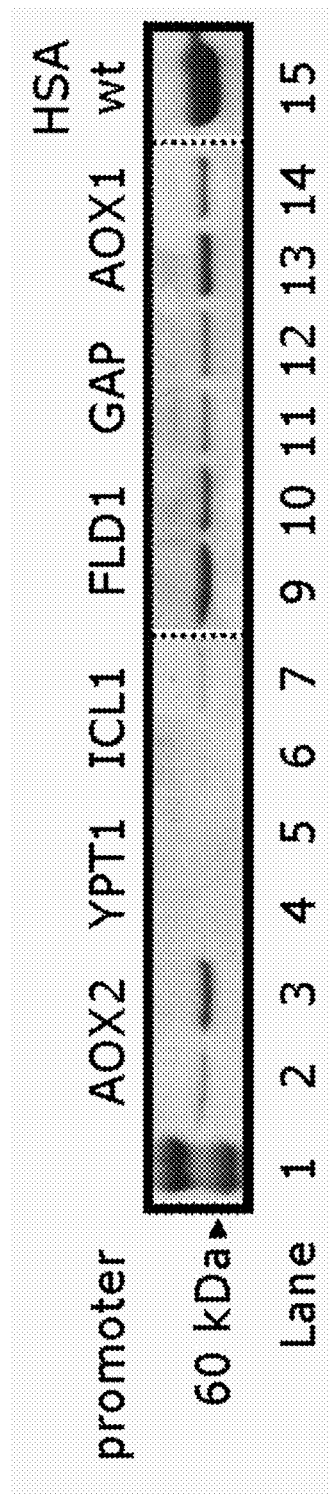
FIG. 9 shows the results of experiments that were performed to determine amber suppression levels with P$_{AOX2}$, P$_{YPT1}$, P$_{ICL1}$, P$_{FLD1}$, P$_{GAP}$, or P$_{AOX1}$ driven aaRS, as assayed by rHSA$_{E37pApa}$ levels in the media. The two clones from each promoter system were independently grown for six days with methanol as the primary carbon source and pApa amino acid. 25 µl of the cleared media was run on a denaturing SDS-PAGE gel and stained with Coomassie. rHSA$_{WT}$ (lane 15) was calculated to be 351.6 mg l$^{-1}$ by band density with BSA control (FIG. 17). By density, P$_{FLD1}$ (lanes 9 and 10 averaged) expressed 43% as much protein, or 151.2 mg l$^{-1}$ (FIG. 16).
Figure 14:
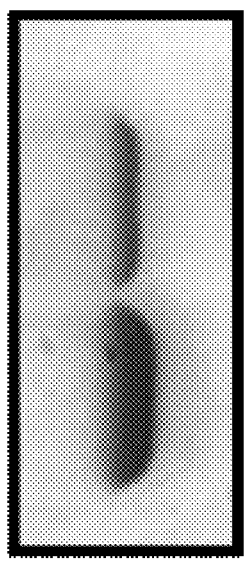
FIG. 14 depicts the results of an experiment that was performed to determine whether rHSA$_{E37X}$ is expressed more robustly in a Mut$^+$ mutant. 25 ul of cleared media from a GS200-rHSA$_{E37X}$/pREAV-P$_{AOX1}$-pApaRS (Mut$^+$) culture (lane 1) or a GS200-rHSA$_{E37X}$/pREAV-P$_{AOX1}$-pApaRS (mut$^s$) culture (lane 2) were analyzed on a SDS-PAGE gel and stained with Coomassie. The Mut$^+$ clone expresses approximately 1.5-2.0 times the amount of rHSA$_{E37X}$ as determined by band density
Figure 15:
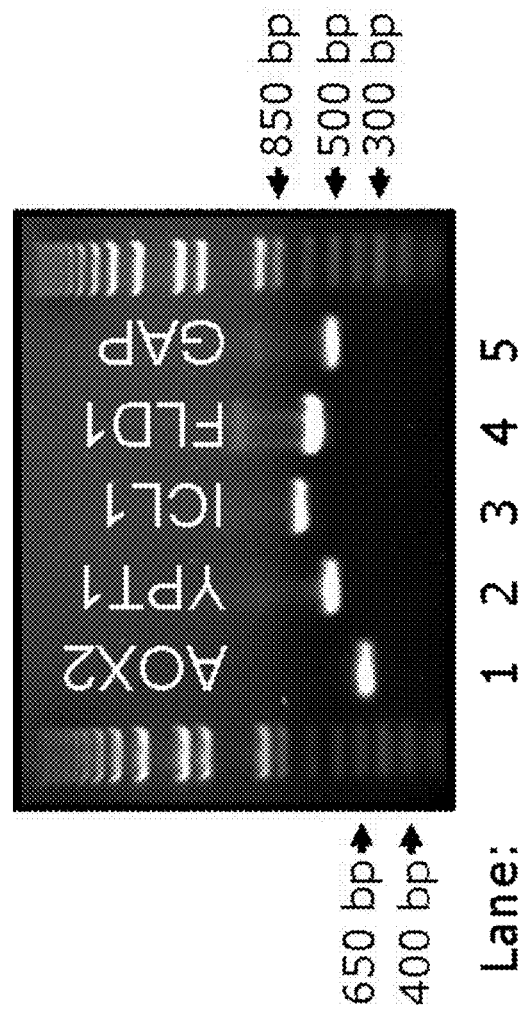
FIG. 15 depicts the results of PCR that was performed to amplify various P. pastoris gene promoters. Primers specific to 5 different promoters were used to PCR amplify their corresponding promoter from genomic DNA. Shown is an ethidium bromide stained gel with a 1 kb+ ladder flanking the PCR products. The expected lengths of the PCRS are PAOX2 342 bp, PYPT1 508 bp, PICL1 683 bp, PFLD1 597 bp, and PGAP 493 bp.
Figure 16:
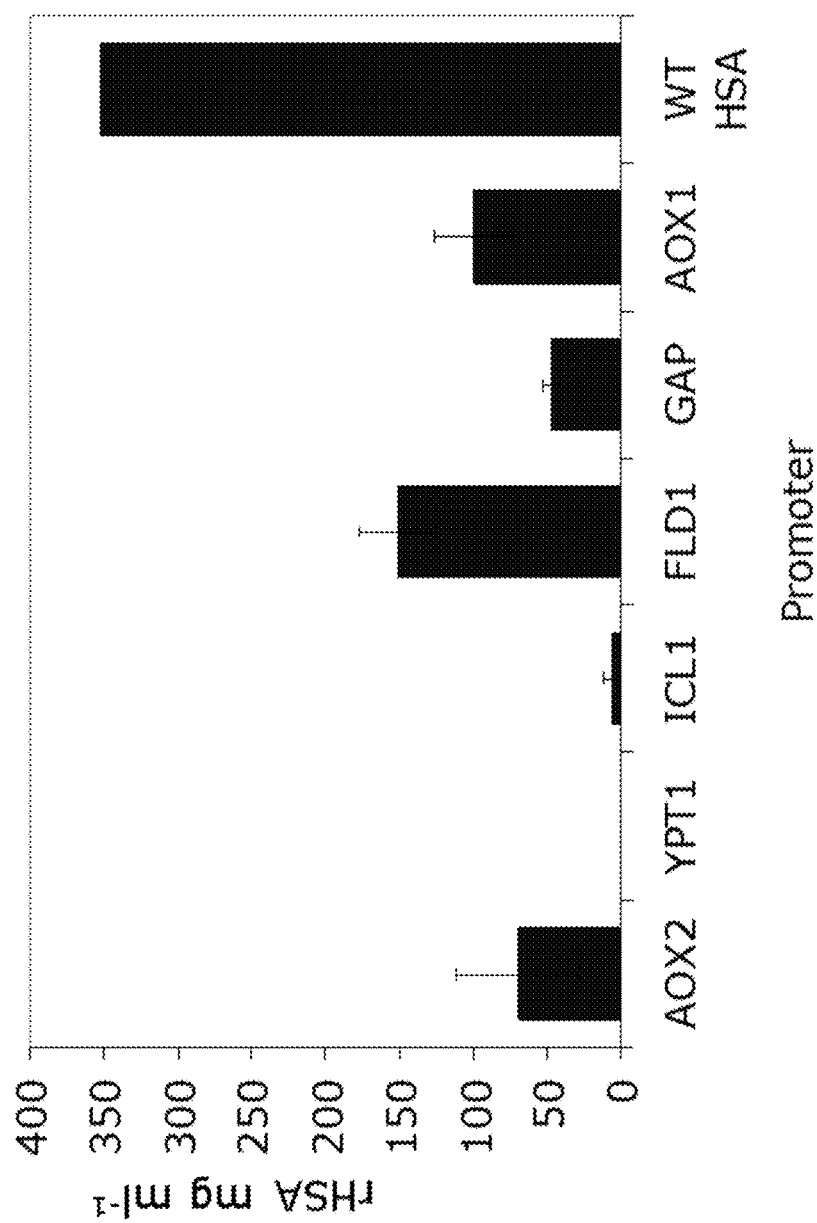
FIG. 16 provides a bar graph representation of the results of FIG. 9 showing amber suppression in rHSA$_{E37pApa}$ as a function of the promoter driving pApaRS production. Bar graph representation of FIG. 9 showing amber suppression in rHSA$_{E37pApa}$ as a function of the promoter driving pApaRS production. Protein production was determined by Coomassie band density on the SDS-PAGE gel shown in FIG. 9. rHSA$_{WT}$ was quantified as described in FIG. 17.
Figure 17:
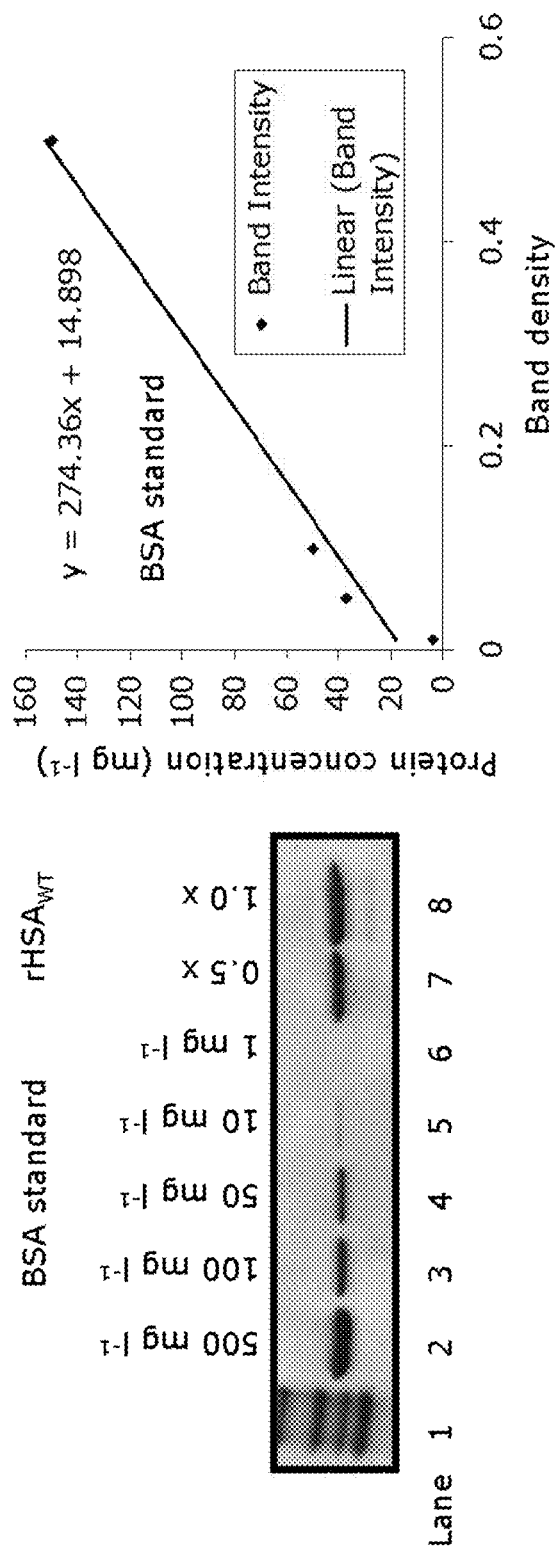
FIG. 17 shows a protein gel on which 25 µl of BSA standards or unpurified rHSA$_{WT}$ media from test protein expressions were run. 25 µl of BSA standards or unpurified rHSA$_{WT}$ media from test protein expressions was run on an SDS-PAGE gel. Lane 7 was a 1:1 dilution of the rHSA$_{WT}$ test protein expression media. BSA standard band densities (lanes 1-4) were plotted, and linearly fit. The densities for rHSA$_{WT}$ bands (2x lane 7 and lane 8) average to 83.33 or, 351.55 mg ml$^{-1}$. Yields of unnatural protein (rHSA$_{E37X}$ in other figures) were determined as a percentage of the same rHSA$_{WT}$ sample.

In an effort to optimize expression of rHSA$_{E37pApa}$, a GS200-rHSA$_{E37X}$/pREAV-P$_{AOX1}$-pApaRS (HIS4, ARG4, Gen$^R$) fast methanol utilization (Mut$^+$) mutant was created by insertion of pPIC3.5k-rHSA$_{E37X}$ into the region 5' of the AOX1 gene locus (this retains the integrity of the AOX1 gene). Genomic insertion in this manner can lead to multimerization, yielding tandem copies of both Gen$^R$ and the gene of interest[7]. The resulting clone displayed resistance to Geneticin up to 1.0 mg ml$^{-1}$, whereas the aforementioned mut$^s$ clone died above 0.25 mg ml$^{-1}$ Geneticin, consistent with the incorporation of multiple copies of the cassette[7,16]. Analysis of full length rHSA$_{E37pApa}$ expression from isolated clones in the presence of methanol and pApa amino acid showed that approximately 1.5-2.0 times more protein was produced than with the mut$^s$ counterpart (FIG. 14). To further increase yields of rHSA$_{E37pApa}$ six different promoters (including P$_{AOX1}$) were compared for their ability to drive pApaRS transcription in the pREAV vector. Transcript mRNA levels, pApaRS protein levels, and overall rHSA$_{E37pApa}$ yields were assayed. Two constitutive promoters derived from yeast GTP binding protein I (YPT1)[26,27] and glyceraldehyde-3-phosphate dehydrogenase (GAP)[12,28], and three methanol inducible promoters from alcohol oxidase II (AOX2)[29], formaldehyde dehydrogenase I (FLD1)[12], and isocitrate lyase I (ICL1)[12] were chosen based on their compatibility with methanol induction. A truncated version of P$_{AOX2}$ was used which enhances the promoter by deleting one of the two repressor binding sequences[29]. The use of the somewhat weaker $P_{YPT1}$ and $P_{GAP}$ promoters[26] could be useful in the event that over production of the synthetase is toxic to the yeast, or sequesters cellular energy away from production of $rHSA_{E37X}$. All promoters were amplified by PCR from *P. pastoris* genomic DNA along with their 5' untranslated regions (FIG. 15). After sequence confirmation, each promoter was cloned into the pREAV vector 5' of pApaRS in place of $P_{AOX1}$, and transformed into the Mut$^+$ GS200-HSA$_{E37X}$ created previously (FIG. 8a). The terminator remained $T_{AOX1}$. $P$-$_{Promoter}$-pApaRS expression levels were monitored by Northern and Western blots after 6 days of methanol induction and compared to $P_{AOX1}$-pApaRS (FIG. 8b-d). Due to inherent expression variability with *P. pastoris*, two clones were chosen for Western blot analysis, and the highest producer was analyzed by Northern blot. $P_{FLD1}$ drove pApaRS transcription four-fold better than $P_{AOX1}$ at the mRNA level, and produced five-fold more pApaRS protein. $P_{GAP}$, $P_{YPT1}$, $P_{ICL1}$, and $P_{AOX2}$ all showed lower pApaRS expression than $P_{FLD1}$. Consistent with this result, the overall amber suppression was highest with $P_{FLD1}$-pApa as measured by $rHSA_{E37pApa}$ expression into the media (FIG. 9). Maximum yields were >150 mg l$^{-1}$ or approximately 43% of $rHSA_{WT}$ yields (352 mg l$^{-1}$) (FIGS. 16, 17).

Oxime Ligation to $rHSA_{E37pApa}$.

Figure 10:
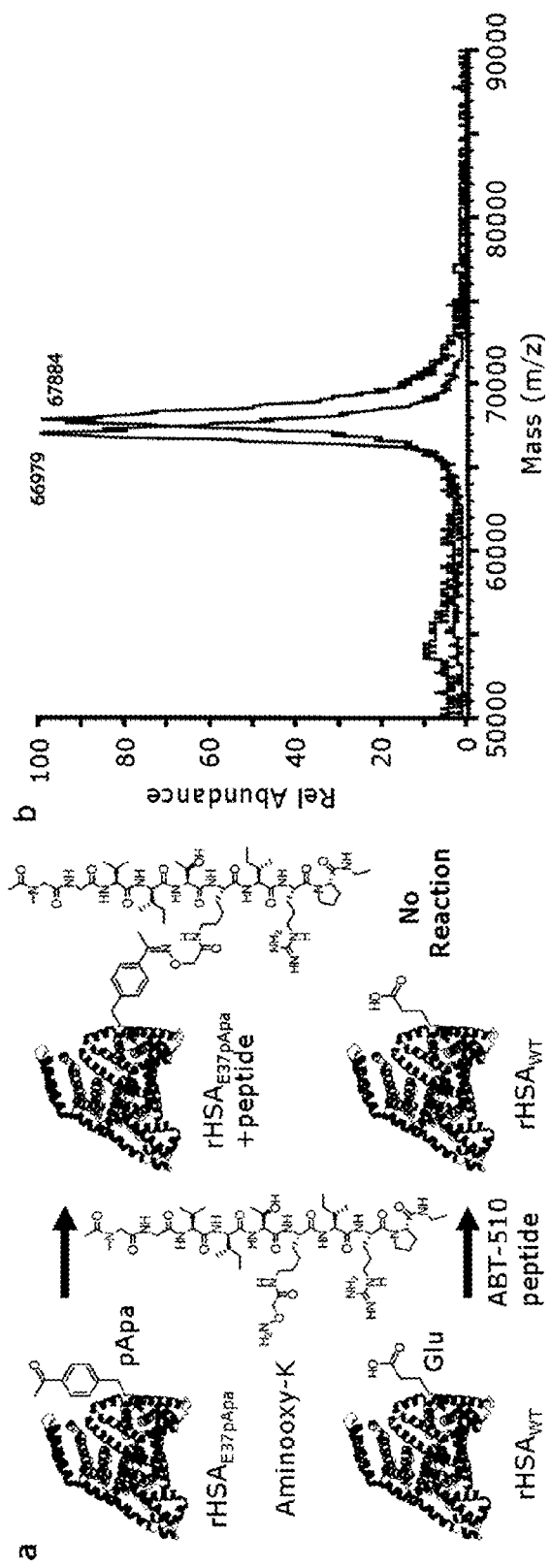
FIG. 10a shows a schematic of oxime ligation of ABT-510 peptide to rHSA$_{E37pApa}$.
FIG. 10b shows the results of MALDI mass spectrometry that was performed to determine the extent of conjugation. (a) Schematic representation of ligation. The ABT-510 peptide harbors an ε-(2-(aminooxy)acetyl)-L-lysine as the sixth residue. Incubation of 75 µM rHSA$_{E37pApa}$ (blue) with 2.25 mM peptide overnight at 37° C., results in the formation of an oxime linkage (top right). No reaction occurs with rHSA$_{WT}$ (red) under identical conditions. (b) MALDI mass spectrometry shows the extent of conjugation. Incubation of peptide with keto containing rHSA$_{E37pApa}$ (blue) results in a 905 Da mass shift compared with incubation with rHSA$_{WT}$ (red), indicating approximately 77% of rHSA$_{E37pApa}$ is linked to ABT-510.

To demonstrate the utility of this modified rHSA as a carrier for bioactive peptides, an oxime ligation was carried out between the unique keto side chain of $rHSA_{E37pApa}$ and the antiangiogenic peptide ABT-510 (FIG. 10). This thrombospondin-1 (TSP-1) properdin type 1 repeat mimetic exhibits its potent anti-tumor activity in humans, but suffers from rapid clearance by the kidneys when administered intravenously[30-32]. A nine amino acid peptide mimetic was synthesized with a unique ε-(2-(aminooxy)acetyl)-L-lysine UAA in place of the sixth L-norvaline residue. Based on the known structure-activity relationships of TSP-1, modifications at this position are not expected to significantly alter biological activity[33]. At pH<5 the aminooxy group undergoes a selective oxime ligation with the keto group of pApa to covalently link the ABT-510 peptide to residue 37 of $rHSA_{E37pApa}$ (FIG. 10a, top). Previous conjugation protocols used an aniline catalyst for efficient ligation[34,35]; however, oxime couplings to $rHSA_{E37pApa}$ proceeded in approximately 77% yield without the use of aniline in an overnight reaction using 75 μM $rHSA_{E37pApa}$ and a thirty-fold excess of the peptide. The extent of derivatization of $rHSA_{E37pApa}$ with the peptide was confirmed by matrix assisted laser desorption ionization (MALDI) mass spectrometry (FIG. 10b). No conjugation was observed by MALDI mass spectrometry when $rHSA_{WT}$ (glutamic acid at residue 37) was treated with the amino-oxy modified ABT-510 peptide under identical conditions.

Addition of 8 UAAs to the Genetic Repertoire.

Figure 11:
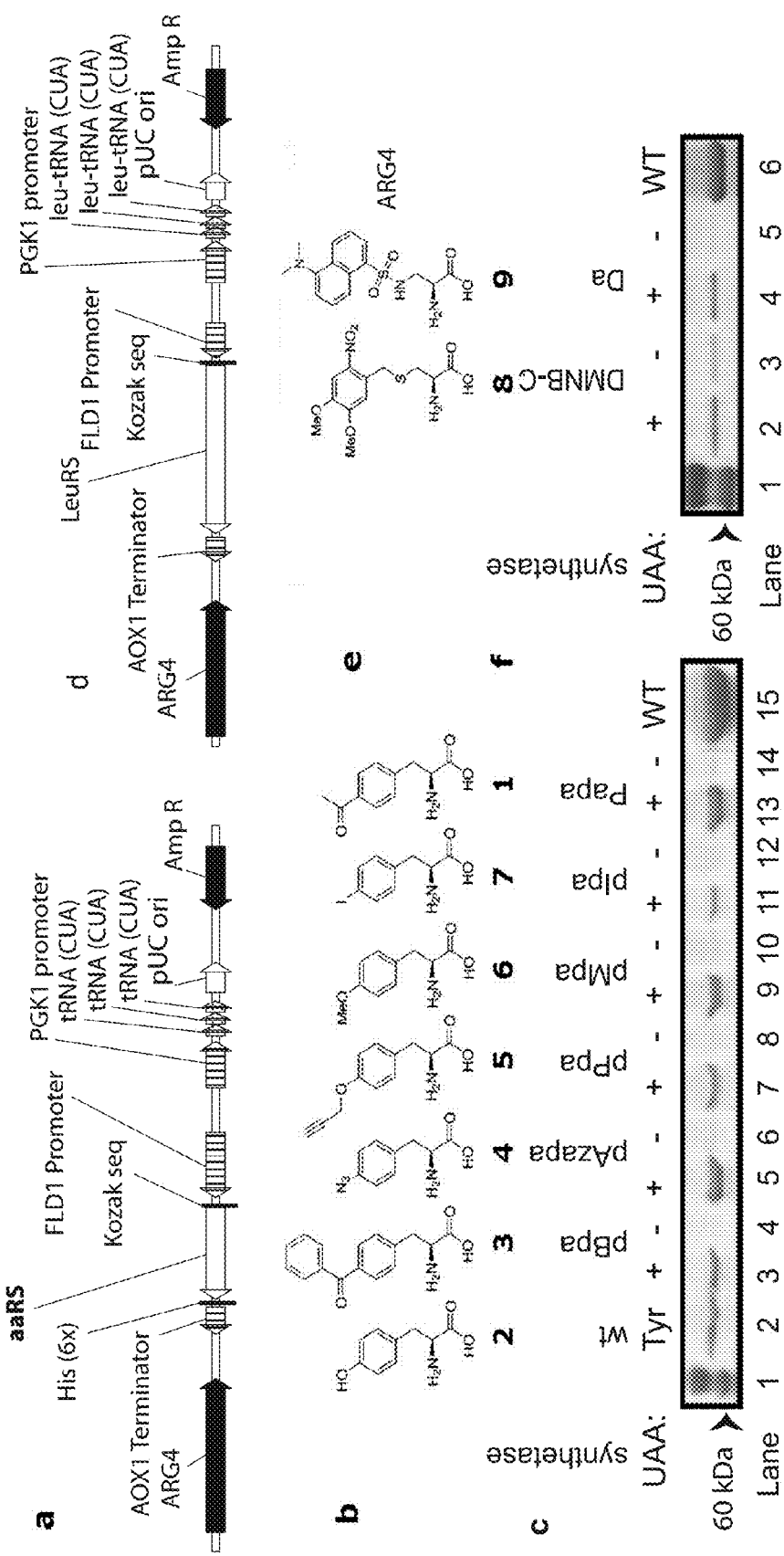
FIG. 11 depicts experiments performed to illustrate that the orthogonal translation system of the invention can be used to incorporate unnatural amino acids other than pApa (e.g., Structures 3-9) into rHSA$_{E37X}$ in P. pastoris. (a) Schematic of the optimized pREAV-P$_{FLD1}$ vector with E. coli tyrosyl-RS gene (orange) and tyrosyl suppressor tRNA cassette (tRNA (CUA), light blue). (b) Structures of six unnatural amino acids (1, 3-7, described in text) and tyrosine (2) with specific E. coli tyrosyl-RS. (c) Expression of rHSA$_{E37X}$ (where X is defined as the unnatural amino acid) in the presence (+) and absence (-) of unnatural amino acids 1, 3-7 with their corresponding aaRS. 25 µl of unpurified cleared media was run on a SDS-PAGE gel and stained with Coomassie. Lane 2 is rHSA$_{E37Y}$ expression with the wild type (wt) tyrosyl-RS. Lane 15 is expression of rHSA$_{WT}$. (d) Schematic of the optimized pREAV$_{leu}$-P$_{FLD1}$ vector with E. coli leucyl-RS gene (LeuRS, orange) and leucyl suppressor tRNA cassette (leu-tRNA (CUA), light blue, red outline). (e) Structure of the DMNB-C and dansyl unnatural amino acids (8, 9, described in text) with specific E. coli leucyl aaRSs. (f) Expression of rHSA$_{E37X}$ in the presence (+) and absence (-) of unnatural amino acids, 8, 9, with their corresponding LeuRS. 25 µl of unpurified cleared media from each protein expression was analyzed on an SDS-PAGE gel and stained with Coomassie. Lane 4 is expression of rHSA$_{WT}$, also after three days.

To illustrate the generality of this newly created recombinant expression system, unnatural aaRSes evolved by the *S. cerevisiae* methodology were inserted into pREAV-$P_{FLD1}$. The aaRSes specific for p-benzoylphenylalanine (pBpa, photocrosslinker, FIG. 11, Structure 3)[2], p-azidophenylalanine (pAzapa, photocrosslinker, chemically reactive, FIG. 11, Structure 4)[36], p-(propargyloxy)phenylalanine (pPpa, chemically reactive, FIG. 11, Structure 5)[36], p-methoxyphenylalanine (pMpa, structure/function probe, FIG. 11, Structure 6)[2], and p-iodophenylalanine (pIpa, heavy atom, FIG. 11, Structure 7)[2] were all inserted behind $P_{FLD1}$ in the optimized pREAV-$P_{FLD1}$ vector (FIG. 11 a,b). For comparison, wild type *E. coli* tyrosyl-RS (wt, FIG. 11, Structure 2) was also inserted into the new expression vector. After transformation into GS200-HSA$_{E37X}$ (HIS4, arg4, Gen$^R$, Mut$^+$), selected clones were compared to the strain harboring pREAV-$P_{FLD1}$-pApaRS in their ability to suppress the amber mutation at position 37 in $rHSA_{E37X}$. Suppression yields were similar for the pApa and pAzapa mutants (40-45% the yield of $rHSA_{WT}$); all other mutants with the exception of pIpa expressed >25% the yield of $rHSA_{WT}$. No protein expression was observed in the absence of the cognate amino acid, demonstrating the high orthogonality of this new system (FIG. 11c).

Figure 18:
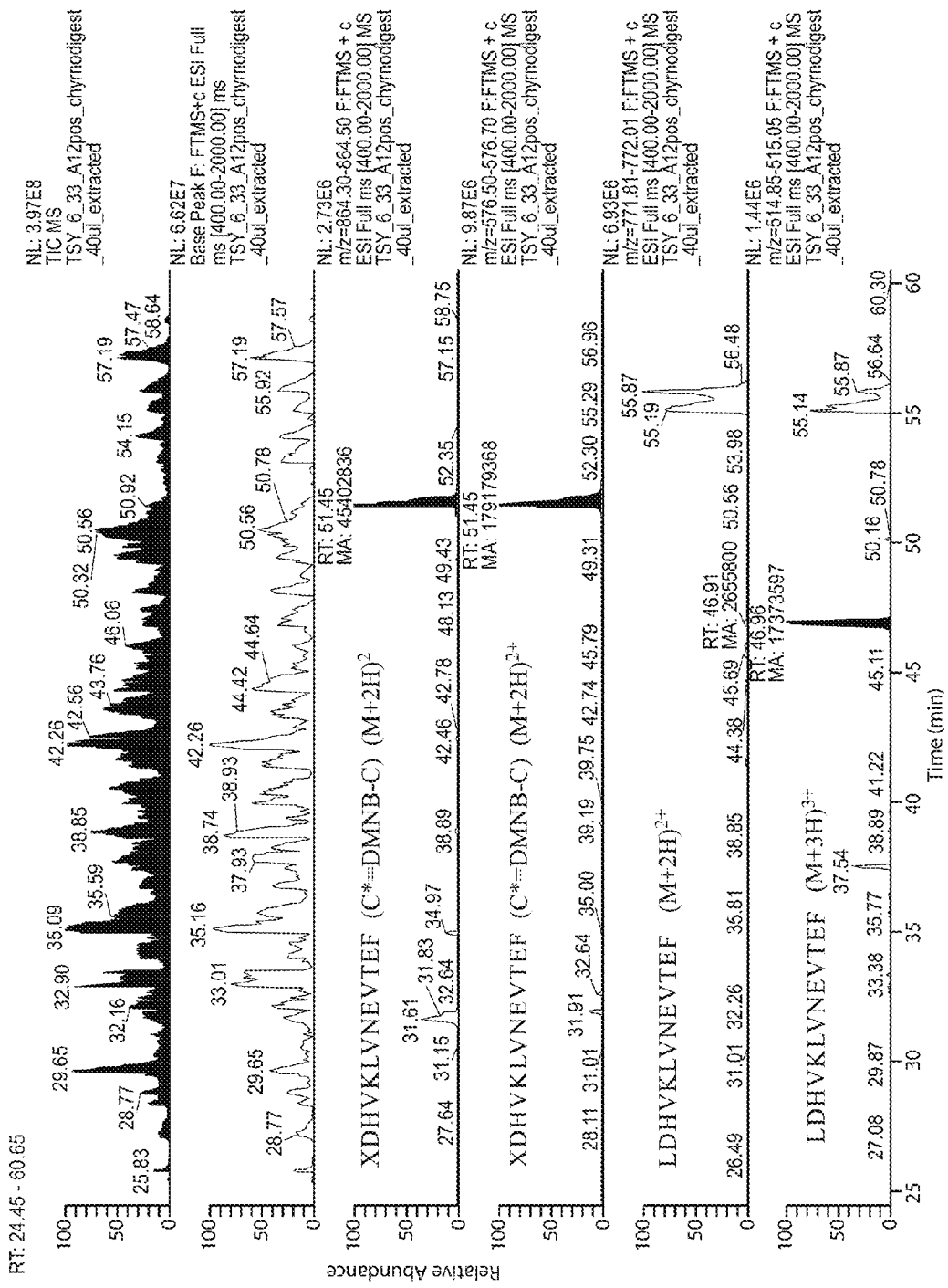
FIG. 18 shows LC-MS/MS of chymotrypsin-digested rHSA$_{E37DMNB-C}$ protein from lane 2 of FIG. 11f. rHSA$_{E37DMNB-C}$ protein from lane 2 of FIG. 11f was subjected to tryptic digest followed by LC-MS/MS as described under the methods section except chymotrypsin replaced trypsin in the digest. The top chromatogram (black) illustrates the total ion count (TIC) for the LC-MS/MS run between minutes 24.45, and 60.05. The third (green) and fourth (blue) chromatograms are ion extractions for the 2+ and 3+ charged species, respectively, corresponding to chymotryptic peptide, XDHVKLVNEVTEF, where X (the 37$^{th}$ residue of rHSA) is DMNB-C (total area under the peaks, "MA"=224582204). The fifth (mustard) and sixth (purple) chromatograms are ion extractions for the 2+ and 3+ charged species, respectively, corresponding to chymotryptic peptide, XDHVKLVNEVTEF, where X is isoleucine of leucine (total area under the peaks "MA"=20029397). Calculations were done as follows: percent E37DMNB-C=224582204/(224582204+20029397)*100=91.8% and percent E37L=20029397/(224582204+20029397)*100=8.2%. Ion species corresponding to the incorporation of other natural amino acids at X were not detected in appreciable amounts.

Recently, a second orthogonal *E. coli* leucyl-derived RS/tRNA$_{CUA}$ pair (aaRS denoted as LeuRS) was generated to incorporate additional unnatural amino acids into proteins in *S. cerevisiae*[37,38]. To accommodate unnatural LeuRSes derived from this orthogonal pair in the new *P. pastoris* expression system, the tRNA region of pREAV-$P_{FLD1}$ plasmid was modified. The existing tRNA$_{CUA}^{Tyr}$ cassette downstream of $P_{PGK1}$ was excised and replaced by a coding region corresponding to three tandem repeats of tRNA$_{CUA}^{Leu5}$ lacking the 5' CCA and separated by SUP4 segments, as previously described, to create pREAV$_{leu}$-$P_{FLD1}$. LeuRS mutants specific for 4,5-dimethoxy-2-nitrobenzylserine (DMNB-S, photocaged serine, FIG. 11, Structure 8)[37] and 2-amino-3-(5-(dimethylamino)naphthalene-1sulfonamide)propanoic acid (dansylalanine, dansyl fluorophore, FIG. 11, Structure 9)[38] were inserted behind $P_{FLD1}$ to create pREAV$_{leu}$-$P_{FLD1}$-LeuRS (FIG. 11d-f). After transformation into the Mut$^+$ GS200-rHSA$_{E37X}$, selected clones were used to express the corresponding mutant $rHSA_{E37X}$ (FIG. 11f). The LeuRS mutant specific for DMNB-S was recently shown to accept the cysteine analog of DMNB-S (DMNB-C), which was used in these expression experiments due to easier synthetic accessibility. Although small amounts of full-length protein were produced in the absence of the cognate amino acid, LC-MS/MS of a tryptic digest confirmed high fidelity of the system in the presence of the corresponding unnatural amino acid (FIG. 18). Suppression yields were approximately 37% the yield of $rHSA_{WT}$ for $rHSA_{E37DMNB-C}$ and 23% the yield of $rHSA_{WT}$ for $rHSA_{E37dansyl}$ after three days of expression.

Discussion

Previous attempts to optimize the expression of proteins containing unnatural amino acids in *S. cerevisiae* resulted in maximal yields of 8-15 mg l$^{-1}$ in model systems, more than an order of magnitude less than demonstrated in the *P. pastoris* system developed here. Work in the Wang lab has recently shown that knockdown of the nonsense-mediated mRNA decay (NMD) pathway in yeast can increase protein expression up to 2-fold[39]. Coupled with the use of a promoter derived from SNR52 to drive tRNA$_{CUA}$ transcription, they were able to achieve yields 300-fold higher yields of mutant protein than previously produced in *S. cerevisiae*, approximately 15 mg l$^{-1}$ [39]. Thus, knockout of the UPF1 gene of the NMD pathway and use of the SNR52-tRNA$_{CUA}$ promoter system may further increase yields in *P. pastoris*. Additionally, work in the Kobayashi lab has demonstrated that yields of $rHSA_{WT}$ from *P. pastoris* are more than an order of magnitude better (>10 g l$^{-1}$) when expressed in fed-batch fermentation rather than in standard shake flasks[10].

In conclusion, we have extended the methodology for the biosynthetic incorporation of unnatural amino acids into methylotrophic yeast. Two aaRS/tRNA$_{CUA}$ pairs were shown to be orthogonal in *P. pastoris* and used to express mutant proteins with eight different unnatural amino acids in response to an amber codon at residue 37 of $rHSA_{E37X}$. This level of versatility suggests that this expression system will be amenable to many other unnatural amino acids with synthetases currently being evolved in *S. cerevisiae* and is not limited to the unnatural amino acids or aaRS/tRNA$_{CUA}$ pairs discussed here. The high yields and fidelities of this new system should make it possible to obtain useful amounts of therapeutic proteins with unique biological and pharmacological properties. For example, chemistries such as oxime ligation or the copper catalyzed 1,3-cycloaddition reaction ("click chemistry") can be exploited to site-specifically PEGylate or crosslink proteins, metal ion binding amino acids can be incorporated to bind radioisotopes, and peptide or toxin conjugates can be made to carrier proteins such as HSA or targeting proteins such as antibodies, respectively. In addition, the aforementioned rHSA$_{E37pApa}$-ABT-510 conjugates are being tested in in vitro antiangiogenisis assays. Efforts to expand the use of rHSA$_{E37pApa}$ as an endogenous, non-immunogenic carrier are currently being applied to other rapidly cleared peptides including glucogen-like peptide 1 mimetics (GLP-1) and parathyroid horomone (PTH) peptides.

Methods

Construction of pPIC3.5k-rHSA.

The rHSA gene was obtained from the Mammalian Gene Collection (NIH), gene accession BC034023. For compatibility with pPIC3.5k linearization[16], BglII sites were removed from rHSA by a modified Quik Change mutagenesis (Stratagene) protocol[40] using primers (IDT): -BglII 1F, 5'-GAC AGA CCT TAC CAA AGT CCA CAC GGA ATG CTG CCA TG-3' and -BglII 1R, 5'-GGT AAG GTC TGT CAC TAA CTT GGA AAC TTC TGC AAA CTC AGC TTT GGG-3' for BglII (781), and -BglII 2F, 5'-CAT GGA GAC CTG CTT GAA TGT GCT GAT GAC AGG GCG G-3' and -BglII 2R, 5'-CAA GCA GGT CTC CAT GGC AGC ATT CCG TGT GGA C-3' for BglII (817) to create rHSA$_{WT}$. The 37$^{th}$ Glu residue was replaced by the amber codon TAG using the modified Quik Change protocol and the primers: Glu37 F', 5'-GAT TGC CTT TGC TCA GTA TCT TCA GCA GTG TCC ATT TTA GGA TCA T-3' and Glu37 R', 5'-GTT TTT GCA AAT TCA GTT ACT TCA TTC ACT AAT TTT ACA TGA TCC TAA AAT GG-3' to create rHSA$_{E37X}$. rHSA$_{WT}$ and rHSA$_{E37X}$ rHSA$_{WT}$ were amplified using primers: HSA Forward, 5'-ATC CGA GGA TCC AAA CGA TGA AGT GGG TAA CCT TTA TTT CCC TTC TTT TTC-3' and HSA Reverse, 5'-GCT AAC GAA TTC ATT ATA AGC CTA AGG CAG CTT GAC TTG CAG C-3', digested with EcoRI and BamHI (NEB) and ligated into the similarly digested pPIC3.5k vector (Invitrogen, vector map available at http://tools.invitrogen.com/content/sfs/manuals/ppic3.5kpao_man.pdf) to create pPIC3.5k-rHSA$_{WT}$ or pPIC3.5k-rHSA$_{E37X}$. Constructs were confirmed by DNA sequencing and amplified in *E. coli* DH10B (Invitrogen).

Construction of pREAV.

The pPR1-P$_{PGK1}$+3SUP4-tRNA$_{CUA}$$^{tyr}$ vector[23] harboring the pApaRS was amplified by PCR, excluding the TRP and 2μ origin regions, to add restriction sites KpnI and HindIII with primers: pESC F, 5'-TAC CAC TAG AAG CTT GGA GAA AAT ACC GCA TCA GGA AAT TGT AAA CGT-3' and pESC R, 5'-GTG AGG GCA GGT ACC GTT CTG TAA AAA TGC AGC TCA GAT TCT TTG TTT G-3' and digested with HindIII and KpnI (NEB). The ARG4 coding region was amplified from pBLARG (gift from the James Cregg laboratory, Keck Graduate Institute, Claremont, Calif.) with primers: ARG4 F new, 5'-AAA TAT GGT ACC TGC CCT CAC GGT GGT TAC GGT-3' and ARG4 R new, 5'-CAT TTC AAG CTT CTA GTG GTA GGA ATT CTG TAC CGG TTT AC-3', digested with KpnI and HindIII, and ligated into the similarly digested pPR1-P$_{PGK1}$+3SUP4-tRNA$_{CUA}$$^{tyr}$ PCR product to create the recombinant eukaryotic ARG4 vector, pREAV-P$_{ADH1}$-pApaRS. To create pREAV-P$_{AOX1}$-pApaRS, the AOX1 promoter and terminator sequences were derived from pPIC3.5k. The pApaRS was amplified with primers: KETO-Koz-F, 5'-TTC TGA GAA TTC ACC ATG GCA AGC AGT AAC TTG ATT AAA CAA TTG C-3' and KetoRS R 6×His, 5'-TAG GCT CGG CCG CTT AGT GGT GGT GGT GGT GGT GTT CCA GCA AAA TCA GAC AGT AAT TCT TTT TAC-3', digested with EcoRI and NotI (NEB) and ligated into the similarly digested pPIC3.5k to create pPIC3.5k-pApaRS. The pREAV-P$_{ADH1}$-pApaRS was amplified by PCR, excluding the P$_{ADH1}$-pApaRS-T$_{ADH1}$ region, to add restriction sites AscI and AflII with primers: pESC-AOX-KETO F, 5'-ATC GTA CTT AAG GAA AGC GTA CTC AAA CAG ACA ACC ATT TCC-3' and pESC-AOX-KETO R, 5'-TTC TCA GGC GCG CCA TCG CCC TTC CCA ACA GTT GCG-3'. The P$_{AOX1}$-pApaRS-T$_{AOX1}$ coding region was amplified from pPIC3.5k-pApaRS with primers: pPIC-keto AOX5 F, 5'-ATC GTA CTT AAG AGA TCT AAC ATC CAA AGA CGA AAG GTT GAA TGA AAC-3' and pPIC-keto AOXTT R, 5'-TGC ACA GGC GCG CCA AGC TTG CAC AAA CGA ACT TCT CAC TTA ATC TTC-3', digested with AscI and AflII (NEB) and ligated into the similarly digested pREAV-P$_{ADH1}$-pApaRS PCR product to create pREAV-P$_{AOX1}$-pApaRS. Constructs were confirmed by size mapping and sequencing.

Transformation of Cassettes into *P. pastoris*.

The double auxotrophic strain, GS200 (his4, arg4) was a gracious gift from the James Cregg lab at the Keck Graduate Institute, and used as the host *P. pastoris* strain. Protocols for yeast competency, transformation, and media recipes were found in the Multi-Copy *Pichia* Expression Kit-Version F[16] (Invitrogen, manual available at http://tools.invitrogen.com/content/sfs/manuals/pichmulti_man.pdf). Briefly, to create GS200-rHSA$_{E37X}$ (HIS4, arg4, Gen$^R$, mut$^s$) 20 μg of pPIC3.5k-rHSA$_{E37X}$ was linearized with BglII (NEB), concentrated to 10 μl by ethanol precipitation, added to 80 μl of freshly competent GS200 in a 2 mm electroporation cuvette (Fisher), and electroporated with the *P. pastoris* settings (2000 V, 25 μF, 200Ω) on a GenePulser Xcell (BioRad). Cells were recovered in 1 ml cold 1 M sorbitol. 250 μl of recovered cells was plated on regeneration dextrose Bacto agar (RDB) plates (15 cm) supplemented with 4 mg ml$^{-1}$ L-arginine (arg) and incubated at 30° C. After 3 days, colonies were picked into 96 well 2 ml blocks (Nunc) with 1 ml yeast peptone dextrose (YPD) media and grown overnight (29.2° C., 300 r.p.m.). The cultures were diluted 1:100 and 1-2 μl replica plated on YPD agar plates containing 0.25 ml$^{-1}$ Geneticin (Invitrogen) and incubated at 30° C. After 4 days, colony G3 showed good growth, was picked, and made competent. Transformations to create GS200-rHSA$_{E37X}$/pREAV-P$_{ADH1}$-pApaRS and GS200-rHSA$_{E37X}$/pREAV-P$_{AOX1}$-pApaRS (HIS4, ARG4, Gen$^R$, mut$^s$) were carried out using the aforementioned protocol with competent G3, except recovered cells were plated on RDB plates lacking L-histidine (his) and arg. After 3 days colonies were picked into 96 well 2 ml blocks and rescreened as above for resistance to 0.25 mg ml$^{-1}$ Geneticin. GS200-rHSA$_{WT}$/pREAV-P$_{ADH1}$-pApaRS (HIS4, ARG4, Gen$^R$, mut$^s$) was created in identical fashion to isolate colony F2. GS200-pREAV-P$_{AOX1}$-pApaRS (his4, ARG4, Gen$^R$, mut$^s$) was created by transforming pREAV-P$_{AOX1}$-pApaRS into GS200, but plated on RDB plates supplemented with 4 mg ml$^{-1}$ his and not further screened for Geneticin resistance.

Test Protein Expression.

All protein expression experiments followed protocols for mut[s] found in the Multi-Copy Pichia Expression Kit[16]. Briefly, 14 colonies for GS200-rHSA$_{E37X}$/pREAV-P$_{ADH1}$-pApaRS, GS200-rHSA$_{E37X}$/pREAV-P$_{AOX1}$-pApaRS or GS200-rHSA$_{WT}$/pREAV-P$_{ADH1}$-pApaRS were picked from plates containing 0.25 mg ml$^{-1}$ Geneticin and grown to near saturation (OD$_{600}$≈12-18) in 10 ml buffered glycerol-complex medium (BMGY) (29.2° C., 300 r.p.m.). Cultures were centrifuged at 1500 g (10 min), and resuspended in 2 ml buffered methanol-complex media (BMMY) with 2 mM pApa amino acid (SynChem). Growth was continued for 6 days, with methanol supplementation to 0.5% every 24 hrs. 200 µl (10% culture volume) of media or sterile water was added every 24 hrs to account for evaporation. 50 µl of media was removed every 24 hrs and cleared of cells by centrifugation at 3000 g (5 min) 25 µl of the cleared media was added to 12.5 µl of SDS loading buffer, heated for 1 min at 95° C. and run on a 4-20% Tris-Glycine SDS-PAGE gel (Invitrogen) (150 V 1 h). Bands at 66.5 kDa in GS200-rHSA$_{E37X}$/pREAV-P$_{AOX1}$-pApaRS and GS200-rHSA$_{WT}$/pREAV-P$_{ADH1}$-PApaRS expression were clearly visible by Coomassie stain (40% methanol, 10% acetic acid, 50% water, 0.1% (w/v) Coomassie Brilliant Blue R250 (Sigma-Aldrich)) after 3 days and peaked after 6 days. Clone G3-2 for GS200-rHSA$_{E37X}$/pREAV-P$_{AOX1}$-pApaRS and F2-wt for GS200-rHSA$_{WT}$/pREAV-P$_{ADH1}$-pApaRS showed highest expression and were used in further comparisons. No clones from GS200-rHSA$_{E37X}$/pREAV-P$_{ADH1}$-pApaRS showed expression by Coomassie stain. To confirm amber suppression was specific for pApa, clones from GS200, G3, GS200-pREAV-P$_{AOX1}$-pApaRS, G3-2, and F2-wt were expressed as described above in the presence or absence of 2 mM pApa, and 0.5% methanol (FIG. 7b).

tRNA Northern Blot.

Two P. pastoris clones, G3-2 and GS200, and two S. cerevisiae clones, SCY4-pPR1-P$_{PGK1}$+2SUP4-tRNA, and SCY4, were grown under their respective expression conditions, and micro RNA (miRNA) harvested via the protocols and reagents found in the Purelink miRNA Isolation Kit (Invitrogen). 2 µg of RNA from each sample was loaded onto two 6% Novex TBE-Urea gel (Invitrogen), and run at 180 V for 1 h. RNA was transferred to a Biodyne B nylon membrane (Pall Life Science) using an XCell Surelock Mini-Cell (Invitrogen) in 0.5×TBE buffer (Invitrogen) and accompanying protocols. The membranes were auto cross-linked with UV Stratalinker 2400 (Stratagene). Hybridization and detection was carried out with protocols and reagents found in the North2South Chemiluminescent Hybridization and Detection Kit (Pierce). Briefly, one blot was incubated with biotinylated probes specific for tRNA$^{ser}$: tRNAser cere 1,5'-/5Biosg/CAT TTC AAG ACT GTC GCC TTA ACC ACT CGG CCA T-3', tRNAser cere 2,5'-/5Biosg/GAA CCA GCG CGG GCA GAG CCC AAC ACA TTT CAA G-3', tRNAser pich 1,5'-/5Biosg/CTG CAT CCT TCG CCT TAA CCA CTC GGC CAT CGT A-3', tRNAser pich 2,5'-/5Biosg/ACA CGA GCA GGG TTC GAA CCT GCG CGG GCA GAG C-3' and the second blot incubated with biotinylated probes specific for tRNA$_{CUA}^{tyr}$: tRNA 5' biot, 5'-/5Biosg/GGA AGG ATT CGA ACC TTC GAA GTC GAT GAC GG-3' and tRNA 3' biot, 5'-/5Biosg/TCT GCT CCC TTT GGC CGC TCG GGA ACC CCA CC-3'. Probes were incubated overnight at 55° C., bound to a streptavidin-horseradish peroxidase (HRP) conjugate, and detected with a luminol/enhancer—stable peroxide solution (Pierce) (FIG. 7a). Relative tRNA amounts were determined by band density using Photoshop CS2 (Adobe).

Scaled Expression, Purification, and Mass Spectrometry of rHSA$_{E37X}$.

For scaled expression of rHSA$_{E37pApa}$, the test expression protocol was modified. 1 L of BMGY was inoculated with 20 ml of saturated G3-2 culture in YPD and grown (~24 h, 29.2° C., 300 r.p.m.) to OD$_{600}$≈12-18. The culture was centrifuged at 1500 g, and resuspended in 200 ml buffered minimal methanol (BMM) supplemented with 10% BMMY and 2 mM pApa. After 6 days of growth (29.2° C., 300 r.p.m. with methanol and volume supplementation) the culture was centrifuged at 3000 g, cells discarded, media passed through a 0.22 µm filter (Milipore). The media was ammonium sulfate (NH$_4$SO) precipitated by addition of NH$_4$SO$_4$ with slow stirring at 4° C. to 50% of saturation (58.2 g), centrifugation at 20,000 g for 20 mM, and again by addition of NH$_4$SO$_4$ to 75% of saturation (31.8 g), and centrifugation at 20,000 g for 20 min. The second precipitation contained rHSA$_{E37pApa}$ and was resuspended in FPLC Buffer A (25 mM Tris-HCl, 25 mM sodium chloride, 1 mM EDTA, 1× protease inhibitor cocktail (Roche), pH=8.5). The resolubilized protein was purified with MonoQ 5/5 column (GE Healthcare) on an AKTA purifier FPLC (Amersham Biosciences) (elution at 20-35% Buffer B (Buffer A+1 M NaCl)). Fractions were analyzed by SDS-PAGE gel, combined, dialyzed with a 30 MWCO dialysis cassette (Pierce) to PBS, and purified with a Superdex 200 10/300 GL (GE Healthcare) on an AKTA purifier FPLC (elution after 14 min in PBS at 0.5 ml min$^{-1}$) Fractions were analyzed by SDS-PAGE gel, combined, and purified with a C8 Vydac HPLC column (300 mm, 200 Å, 5 µm, Grace) on a Dynamax HPLC (Rainin) (elution at 40-46% MeCN in water, 0.1% TFA). Fractions were analyzed by SDS-PAGE gel, and rHSA$_{E37pApa}$ containing fractions flash frozen and lyophilized to a white powder. Purification of rHSA$_{WT}$ from F2-wt was done in similar fashion.

Tryptic Digest, Nano-RP LC-MS/MS.

Purified rHSA$_{E37X}$ was digested overnight with trypsin under reducing conditions (10 mM TCEP, 1M guanidinium HCl, 100 mM triethanolamine HCl, pH=7.8). The digest was purified by reversed-phase solid-phase extraction (Sep-Pak, C18, Waters) and lyophilized. Oxidation of cysteines to cysteic acid and methionine to methionine sulfone was performed by incubation of lyophilized peptides with performic acid (9 parts conc. formic acid+1 part 30% H$_2$O$_2$)[41] for 1 h on ice. The reaction was quenched by addition of an excess of mercaptoethanol and 20× dilution with water. Nano-RP LC-MS/MS was performed with a HPLC system (Agilent Technologies) equipped with an LTQ Orbitrap hybrid mass spectrometer (ThermoElectron). Tryptic digests were loaded onto the precolumn (4 cm, 100 µm i.d., 5 µm, Monitor C18, Column Engineering) of a vented column setup[42] at a flow rate of ~2 µl min$^{-1}$. After a load/wash period of 10 min gradient elution was started by switching the precolumn in line with the analytical column (10 cm, 75 µm i.d., 5 µm C18). The chromatographic profile was from 100% solvent A (0.1% aqueous acetic acid) to 50% solvent B (0.1% acetic acid in acetonitrile) in 40 mM at ~100 nl min$^{-1}$ Data-dependent MS/MS acquisitions were performed following a top 10 scheme in which the mass spectrometer was programmed to first record a high-resolution Orbitrap scan (m/z 500-2,000) followed by 10 data-dependent MS/MS scans (relative collision energy=35%; 3 Da isolation window). The raw data was searched against the SwissProt 51.6 database using MASCOT (Matrixscience, London, UK) for protein identification with pApa as a variable modification.

Creation of Mut+ Phenotype.

To create GS200-rHSA$_{E37X}$/pREAV-P$_{AOX1}$-pApaRS (HIS4, ARG4, Gen$^R$, Mut+), 20 μg of pPIC3.5k-rHSA$_{E37X}$ was linearized with SacI, or SalI (NEB) and transformed into freshly competent GS200 as previously described. Cells were recovered in 1 ml of cold 1 M sorbitol, and plated on RDB plates supplemented with 0.4 mg ml$^{-1}$ arg. Colonies were picked into a 2 ml 96 well block with 1 ml YPD, grown to saturation (29.2° C., 300 r.p.m.), diluted 1:100, and replica plated on plates containing 0 to 3.0 mg ml$^{-1}$ Geneticin. Clone 1D12 which survived up to 1.0 mg ml$^{-1}$ Geneticin, was made competent, transformed with pREAV-P$_{AOX1}$-pApaRS as previously described and plated on RDB plates lacking Arg or His. Colonies were picked into a 1 ml 96 well block, grown to saturation, diluted 1:100, and rescreened on Geneticin 1.0 mg ml$^{-1}$ plates. 14 surviving clones were picked, and tested for rHSA$_{E37pApa}$ expression in the presence of pApa amino acid and methanol. For continuity, the mut$^s$ protocol was used as described above. Clone K5 showed greatest protein expression, and was compared to G3-2 in test expressions (FIG. 14). Relative amounts of protein determined by band density using Photoshop CS2 (Adobe).

Construction of pREAV-P$_{promoter}$-PApaRS.

Five promoters, P$_{AOX2}$, P$_{YPT1}$, P$_{ICL1}$, P$_{FLD1}$, and P$_{GAP}$ were separately amplified by PCR from genomic DNA (P. pastoris GS200) using the following primers: PAOX2 F, 5'-GTA TCG CTT AAG TCC AAG ATA GGC TAT TTT TGT CGC ATA AAT TTT TGT C-3' and PAOX2 R, 5'-CGT TAG CCA TGG TTT TCT CAG TTG ATT TGT TTG TGG GGA TTT AGT AAG TCG-3'; PYPT1 F, 5'-GTA TCG CTT AAG CAT ATG ATG AGT CAC AAT CTG CTT CCA CAG ACG AG-3' and PYPT1 R, 5'-CGT TAG CCA TGG GAC TGC TAT TAT CTC TGT GTG TAT GTG TGT ATT GGG C-3'; PICL1 F, 5'-GTA TCG CTT AAG GAA TTC GGA CAA ATG TGC TGT TCC GGT AGC TTG-3' and PICL1 R, 5'-CGT TAG CCA TGG TCT TGA TAT ACT TGA TAC TGT GTT CTT TGA ATT GAA AG-3'; PFLD1 F, 5'-GTA TCG CTT AAG GCA TGC AGG AAT CTC TGG CAC GGT GCT AAT GG-3' and PFLD1 R, 5'-CGT TAG CCA TGG TGT GAA TAT CAA GAA TTG TAT GAA CAA GCA AAG TTG G-3'; PGAP1 F, 5'-GTA TCG CTT AAG GGA TCC TTT TTT GTA GAA ATG TCT TGG TGT CCT CGT C-3' and PGAP1 F, 5'-CGT TAG CCA TGG TGT GTT TTG ATA GTT GTT CAA TTG ATT GAA ATA GGG AC-3'; respectively (FIG. 15). The PCR amplified fragments were digested with AflII and NcoI (NEB) and ligated into the similarly digested pREAV-P$_{AOX1}$-pApaRS (after removal of the P$_{AOX2}$ coding region via agarose gel purification) to create the pREAV-P$_{Promoter}$-pApaRS. After sequence confirmation, the plasmids (including the previously constructed pREAV-P$_{AOX1}$-pApaRS) were linearized with AatII, transformed into freshly competent GS200-rHSA$_{E37X}$ (clone 1D12), and plated on RDB plates lacking Arg or His as previously described to create GS200-rHSA$_{E37X}$/pREAV-P$_{Promoter}$-pApaRS (HIS4, ARG4, Gen$^R$, Mut+). Surviving clones were screened for Geneticin resistance at 0.75 and 1.0 mg ml$^{-1}$. 48 clones corresponding to each promoter were picked into 1 mL 96 well blocks containing BMGY and grown to saturation (29.2° C., 24 h, 300 r.p.m.). The saturated cultures were centrifuged at 1500 g for 10 min and cells were resuspended in 200 μL BMMY+2 mM pApa amino acid. After 6 days (29.2° C., 300 r.p.m., with supplementation), the media was cleared by centrifugation at 3000 g for 10 minutes, and 1-2 μL of the cleared media spotted on a 0.45 micron nitrocellulose membrane (Bio-Rad) using a 96 well pin tool. The membrane was probed with the HSA antibody [1A9] HRP conjugate (Abcam) using standard Western blotting techniques[43], and detected with ECL HRP chemiluminescence detection reagents and protocols (GE Healthcare). The two highest expressing clones corresponding to each promoter (AOX2: A6, B7; YPT1: D11, B7; ICL1: E5, H3; FLD1: E11, F3; GAP: B7, B10; and AOX1: E3, E7) were chosen for parallel test expressions (FIG. 8).

pApaRS Northern Blot.

Top expressing clones AOX2, B7; YPT1, D11; ICL1, H3; FLD1, E11; GAP, B7; and AOX1, E3, were grown under test expression conditions for 6 days. 3×10$^8$ cells (2.5 ml at OD$_{600}$=1.0) were collected and total RNA isolated via the RiboPure—Yeast Kit (Ambion) reagents and protocols. 13 μg of each RNA sample was loaded onto a 2% formaldehyde gel (2% agarose, 20 mM MOPS, 8 mM sodium acetate, 2.2 mM formaldehyde, pH=7.0). 3 volumes of NorthernMax formaldehyde load dye (Ambion) was mixed with 1 volume of RNA, heated to 65° C. for 15 mins, and chilled on ice for 5 mins before loading. The gel was electrophoresed (50 V for 2 h) and equal loading confirmed via ethidium bromide straining of 18S and 28S rRNA (FIG. 8c, top). The RNA was drawn onto a Biodyne B nylon membrane (Pall Life Science) in 10×SSC buffer (1.5 M sodium chloride, 0.15 M sodium citrate pH=7.0) via a standard blotting apparatus. The membrane was rinsed in 2×SSC buffer, dried, and auto-crosslinked with a UV Stratalinker 2400 (Stratagene). Hybridization and detection was carried out via protocols and reagents from the North2South Chemiluminescent Hybridization and Detection Kit (Pierce). Briefly, 400-500 μg of biotinylated probes: ketoRS3 biot 5'-/5Biosg/TGA GAC GCT GCT TAA CCG CTT C-3' and ketoRS4 biot 5'-/5Biosg/TAA AGA AGT ATT CAG GAT CGG ACT G-3' were incubated overnight at 55° C., bound to a streptavidin-HRP conjugate, and detected with a luminol/enhancer—stable peroxide solution (Pierce) (FIG. 8c, bottom). Relative mRNA titers were determined by band density using Photoshop CS2.

pApaRS Western Blot.

Clones, AOX2: A6, B7; YPT1: D11, B7; ICL1: E5, H3; FLD1: E11, F3; GAP: B7, B10; and AOX1: E3, E7 were cultured under test expression conditions, pelletted (3000 g, 10 mM), and lysed with 2 ml YeastBuster (Novagen)+10 mM β-mercaptoethanol and Complete (Roche) protease inhibitor tablets. Samples were cleared at 20,000 g and 15 μl of the lysate run on a 4-20% SDS-PAGE gel (1:15 h, 150 V). The protein was transferred to a 0.45 micron nitrocellulose membrane (Bio-Rad) using a Trans-Blot SD semi-dry transfer cell (Bio-Rad) in Tobin's transfer buffer (24 mM tris base, 192 mM glycine, 20% ethanol) (2 h, 20 V, 100 mAmp). Residual protein on gel was stained with Coomassie (FIG. 8b, top) to ensure equal loading. The membrane was blotted using standard Western blotting techniques[43] with an anti His$_{6x}$-HRP conjugated antibody (Sigma-Aldrich) and detected with ECL (GE Healthcare) HRP chemiluminescence detection reagents and protocols (FIG. 8b, bottom). Relative expression rates were determined by band density using Photoshop CS2.

rHSA$_{E37X}$-ABT-510 Oxime Ligation.

An ABT-510 peptide mimetic was synthesized (Anaspec) with a ε-(2-(aminooxy)acetyl)-L-lysine replacing the sixth L-norvaline residue (sequence: Ac-Sar-Gly-Val-D-aloIle-Thr-Lys(Aoa)-Ile-Arg-Pro-NEt MW=1097.3 Da). 2.25 mM (0.5 mg) of the peptide was added to 75 μM rHSA$_{E37pApa}$ or rHSA$_{WT}$ (1.0 mg) in 200 μl oxime ligation buffer (1.5 M sodium chloride, 500 mM sodium acetate, pH=4.4) and incubated overnight at 37° C. The reactions were purified with a C8 Vydac HPLC column (300 mm, 200 Å, 5 μm, Grace) on a Dynamax HPLC (Rainin) (elution 40-46% acetonitrile in water, 0.1%). Fractions were collected, combined, and analyzed via Coomassie stained SDS-PAGE gel. Intact protein mass measurements were performed using a linear MALDI-TOF MS Biflex III (Burker Daltonics) instrument with a sinapinic acid matrix. The mass difference between rHSA$_{WT}$+peptide and rHSA$_{E37pApa}$+peptide, less 60 Da owing to the E37pApa mutation (905 Da less 60 Da=845 Da), was used to determine ligation efficiency (~77%). The mass of rHSA$_{WT}$ changed negligibly before and after treatment with the protein.

pREAV-P$_{FLD1}$-(Synthetase$_{tyr}$) Construction and Transformation:

Unnatural aaRSs specific for tyrosine (wt), pBpa, pAzapa, pPpa, pMpa, and pIpa were amplified by PCR using the primers: KETO-Koz-F and KetoRS R 6×His (described above), digested with NcoI and EagI (NEB) and ligated into the similarly digested pREAV-P$_{FLD1}$-pApaRS (after removal of the pApaRS region via agarose gel purification). After sequence confirmation, the plasmids were transformed into GS200-rHSA$_{E37X}$ clone 1D12 as previously described to create GS200-rHSA$_{E37X}$/pREAV-P$_{FLD1}$-(synthetase$_{tyr}$) (HIS4, ARG4, Gen$^R$, Mut$^+$). 12 clones were chosen from each transformation and screened via dot blot in 96 well format as previously described. The best producer was chosen from each (tyr, A9; pBpa, B7; pAzapa C9; pPpa, D6; pMpa, E6; and pIpa, F6) and compared to FLD1, E11 in test expressions (FIG. 11c). Relative protein yields were determined by band density using Photoshop CS2.

pREAV-P$_{FLD1}$-(Synthetase$_{leu}$) Construction and Transformation:

To create pREAV$_{leu}$-P$_{FLD1}$ a section corresponding to three tandem repeats of tRNA$_{CUA}$$^{Leu5}$ lacking the 5' CCA and separated by SUP4 segments was synthesized (DNA 2.0) and PCR amplified using primers: Leu tRNA F, 5'-AAG GAA GCT AGC CTC TTT TTC AAT TGT ATA TGT G-3' and Leu tRNA R, 5'-CGT ACA CGC GTC TGT ACA GAA AAA AAA GAA AAA TTT G-3'. The resulting 643 bp product was digested with NheI and MluI (NEB) and ligated into the similarly digested pREAV-P$_{FLD1}$-pApaRS (after removal of the tyrosyl tRNA via agarose gel purification), to create pREAV$_{leu}$-P$_{FLD1}$-pApaRS. aaRSs with specificity for the DMNB-S and dansyl unnatural amino acids were amplified using primers: LeuRS F, 5'-ATT CAC ACC ATG GAA GAG CAA TAC CGC CCG GAA GAG-3' and LeuRS R, 5'-TTA ATT CGC GGC CGC TTA GCC AAC GAC CAG ATT GAG GAG TTT ACC TG-3', digested with NcoI and NotI (NEB), and ligated into the similarly digested pREAV$_{leu}$-P$_{FLD1}$-pApaRS (after removal of the pApaRS coding region via agarose gel purification) to create pREAV$_{leu}$-P$_{FLD1}$-DMNB-S or pREAV$_{leu}$-P$_{FLD1}$-dansyl (FIG. 11d). After sequence confirmation, the plasmids were transformed into GS200-rHSA$_{E37X}$ (clone 1D12) and screened in 96 well dot blot format as described. Clones A:A5 (DMNB-S) and B:G12 (dansyl) were identified as successful producers grown under test expression conditions for three days post induction in buffer minimal methanol (BMM) media. rHSA$_{WT}$ was expressed for three days in BMMY for comparison (FIG. 11f). Incorporation of the dansyl and DMNB-S (analog amino acid) was further confirmed via LC-MS/MS as described above (FIG. 18). Relative band densities were determined by Photoshop CS2.

Figure Legends

FIG. 6: Vectors for amber suppression in eukaryotes illustrating markers (maroon), replication origins (black), target proteins (orange), control elements (green), and suppressor tRNAs ("tRNA (CUA)", light blue). (a) Map of the commercially available pPIC3.5k shuttle vector[16] for in vivo multi-copy incorporation and expression in P. pastoris. rHSA$_{E37X}$ (orange) is subcloned between the AOX1 promoter and terminator. (b) Optimized amber suppression vector for S. cerevisiae[23] harboring the pApaRS/tRNA$_{CUA}$$^{tyr}$ pair under P$_{ADH1}$ control. tRNA$_{CUA}$ repeats are separated by regions from the SUP4 gene (not labeled) and driven by P$_{PGK1}$. (c) Modified pPR1-P$_{PGK1}$+3SUP4-tRNA plasmid where the 2μ eukaryotic origin and TRP marker were replaced by ARG4 to create pREAV-P$_{ADH1}$-pApaRS. (d) P$_{ADH1}$ and T$_{ADH1}$ were replaced by their AOX1 counterparts to create pREAV-P$_{AOX1}$-pApaRS. (e) The first 61 amino acids of rHSA$_{E37X}$. The pre-pro leader peptide (blue, green) allows export of rHSA$_{E37X}$ into the media and is cleaved during transport to yield the mature protein (rHSA, orange) beginning with an aspartic acid. The 37$^{th}$ residue (X, red) of the mature rHSA denotes the unnatural amino acid incorporated in response to the amber codon.

FIG. 7: Amber suppression with pApa in P. pastoris. (a) A Northern blot (bottom gel) was used to assay suppressor tRNA$_{CUA}$$^{Tyr}$ transcription in S. cerevisiae+pPR1-P$_{PGK1}$-3SUP4-tRNA (lane 1) and P. pastoris+pREAV-P$_{ADH1}$-pApaRS (lane 2). For a negative control, lanes 3 and 4 are S. cerevisiae and P. pastoris strains lacking vectors, respectively. The top gel shows a Northern blot for the endogenous serine tRNA and illustrates equal miRNA preparation in all samples. (b) To assay the fidelity of the system, 25 μl of cleared media from 6 days of growth was analyzed on a denaturing SDS-PAGE gel and stained with Coomassie. Lane 2 is GS200; lane 3 is GS200-HSA$_{E37X}$; lane 4 is GS200-pREAV-P$_{AOX1}$-pApaRS; lanes 5-7 are GS200-HSA$_{E37X}$/pREAV-P$_{AOX1}$-pApaRS; and lane 8 is GS200-HSA$_{WT}$/pREAV-P$_{ADH1}$-pApaRS. Amber suppression only occurs in yeast harboring both vectors, and grown with methanol and pApa amino acid (pApa AA). (c) MS/MS fragmentation of a tryptic peptide (top) containing the unnatural amino acid pApa (denoted E*) at residue 37 of mature rHSA$_{E37pApa}$. The substitution is supported without ambiguity by the observed fragment ion series. Sequence ions are labeled with standard nomenclature[44].

FIG. 8: Comparison of pApaRS promoters for optimized amber suppression. (a) Linear map of pREAV-P$_{Promoter}$-pApaRS illustrating the promoter region (green, red outline) being varied. Promoters were PCR amplified from genomic DNA (FIG. 12). (b) Two clones from each transformation of GS200-rHSA$_{E37X}$ with pREAV-P$_{Promoter}$-pApaRS were grown with methanol as the primary carbon source for 6 days, lysed, separated on an SDS-PAGE gel (top gel). The gel was stained with Coomassie to verify equal loading. Lysates were analyzed via Western blot for pApaRs-His$_{6x}$ (bottom gel). (c) The clones which produced most protein in b were analyzed by Northern blot for pApaRS mRNA transcription (bottom gel). Bands for the 18s and 28s ribosomal RNA were stained with ethidium bromide (top gel) confirm RNA integrity and equal loading. (d) Bar graph representation of b determined by density of stained band, averaging the duplicates. Error bars represent variance.

FIG. 9: Amber suppression levels with P$_{AOX2}$, P$_{YPT1}$, P$_{ICL1}$, P$_{FLD1}$, P$_{GAP}$, or P$_{AOX1}$ driven aaRS, assayed by rHSA$_{E37pApa}$ in the media. The two clones from each promoter system were independently grown for six days with methanol as the primary carbon source and pApa amino acid. 25 μl of the cleared media was run on a denaturing SDS-PAGE gel and stained with Coomassie. rHSA$_{WT}$ (lane 15) was calculated to be 351.6 mg l$^{-1}$ by band density with BSA control (FIG. 17). By density, $P_{FLD1}$ (lanes 9 and 10 averaged) expressed 43% as much protein, or 151.2 mg l$^{-1}$ (FIG. 16).

FIG. 10: Oxime ligation of ABT-510 peptide to rHSA$_{E37pApa}$. (a) Schematic representation of ligation. The ABT-510 peptide harbors an ε-(2-(aminooxy)acetyl)-L-lysine as the sixth residue. Incubation of 75 μM rHSA$_{E37pApa}$ (blue) with 2.25 mM peptide overnight at 37° C., results in the formation of an oxime linkage (top right). No reaction occurs with rHSA$_{WT}$ (red) under identical conditions. (b) MALDI mass spectrometry shows the extent of conjugation. Incubation of peptide with keto containing rHSA$_{E37pApa}$ (blue) results in a 905 Da mass shift compared with incubation with rHSA$_{WT}$ (red), indicating approximately 77% of rHSA$_{E37pApa}$ is linked to ABT-510.

FIG. 11: Addition of eight unnatural amino acids to the genetic repertoire. (a) Schematic of the optimized pREAV-P$_{FLD1}$ vector with E. coli tyrosyl-RS gene (orange) and tyrosyl suppressor tRNA cassette (tRNA (CUA), light blue). (b) Structures of six unnatural amino acids (1, 3-7, described in text) and tyrosine (2) with specific E. coli tyrosyl-RS. (c) Expression of rHSA$_{E37X}$ (where X is defined as the unnatural amino acid) in the presence (+) and absence (−) of unnatural amino acids 1, 3-7 with their corresponding aaRS. 25 μl of unpurified cleared media was run on a SDS-PAGE gel and stained with Coomassie. Lane 2 is rHSA$_{E37Y}$ expression with the wild type (wt) tyrosyl-RS. Lane 15 is expression of rHSA$_{WT}$. (d) Schematic of the optimized pREAV$_{leu}$-P$_{FLD1}$ vector with E. coli leucyl-RS gene (LeuRS, orange) and leucyl suppressor tRNA cassette (leu-tRNA (CUA), light blue, red outline). (e) Structure of the DMNB-C and dansyl unnatural amino acids (8, 9, described in text) with specific E. coli leucyl aaRSs. (f) Expression of rHSA$_{E37X}$ in the presence (+) and absence (−) of unnatural amino acids, 8, 9, with their corresponding LeuRS. 25 μl of unpurified cleared media from each protein expression was analyzed on an SDS-PAGE gel and stained with Coomassie. Lane 4 is expression of rHSA$_{WT}$, also after three days.

FIG. 12: PCR amplification from genomic DNA of the 3 components of the unnatural amino acid suppression system, showing successful incorporation of the pPIC3.5k and pREAV cassettes into GS200-rHSA$_{E37X}$/pREAV-P$_{ADH1}$-pApaRS. 4 clones were chosen from one transformation and labeled 1-4. Expected PCR products were rHSA 1851 bp, pApaRS 1317 bp, and tRNA cassette 1100 bp. The lack of pApaRS amplification in clone 2 is likely a technical artifact.

FIG. 13: Western blot for pApaRS-$_{His6x}$ in four separate clones of GS200-rHSA$_{E37X}$/pREAV-P$_{ADH1}$-pApaRS from a single transformation. No pApaRS protein was detectable.

FIG. 14: 25 ul of cleared media from a GS200-rHSA$_{E37X}$/pREAV-P$_{AOX1}$-pApaRS (Mut$^+$) culture (lane 1) or a GS200-rHSA$_{E37X}$/pREAV-P$_{AOX1}$-pApaRS (mut$^s$) culture (lane 2) were analyzed on a SDS-PAGE gel and stained with Coomassie. The Mut$^+$ clone expresses approximately 1.5-2.0 times the amount of rHSA$_{E37X}$ as determined by band density FIG. 15: Primers specific to 5 different promoters were used to PCR amplify their corresponding promoter from genomic DNA. Shown is an ethidium bromide stained gel with a 1 kb+ ladder flanking the PCR products. The expected lengths of the PCRS are PAOX2 342 bp, PYPT1 508 bp, PICL1 683 bp, PFLD1 597 bp, and PGAP 493 bp.

FIG. 16: Bar graph representation of FIG. 9 showing amber suppression in rHSA$_{E37pApa}$ as a function of the promoter driving pApaRS production. Protein production was determined by Coomassie band density on the SDS-PAGE gel shown in FIG. 9. rHSA$_{WT}$ was quantified as described in FIG. 17.

FIG. 17: 25 μl of BSA standards or unpurified rHSA$_{WT}$ media from test protein expressions was run on an SDS-PAGE gel. Lane 7 was a 1:1 dilution of the rHSA$_{WT}$ test protein expression media. BSA standard band densities (lanes 1-4) were plotted, and linearly fit. The densities for rHSA$_{WT}$ bands (2× lane 7 and lane 8) average to 83.33 or, 351.55 mg ml$^{-1}$. Yields of unnatural protein (rHSA$_{E37X}$ in other figures) were determined as a percentage of the same rHSA$_{WT}$ sample.

FIG. 18: rHSA$_{E37DMNB-C}$ protein from lane 2 of FIG. 11f was subjected to tryptic digest followed by LC-MS/MS as described under the methods section except chymotrypsin replaced trypsin in the digest. The top chromatogram (black) illustrates the total ion count (TIC) for the LC-MS/MS run between minutes 24.45, and 60.05. The third (green) and fourth (blue) chromatograms are ion extractions for the 2+ and 3+ charged species, respectively, corresponding to chymotryptic peptide, XDHVKLVNEVTEF, where X (the 37$^{th}$ residue of rHSA) is DMNB-C (total area under the peaks, "MA"=224582204). The fifth (mustard) and sixth (purple) chromatograms are ion extractions for the 2+ and 3+ charged species, respectively, corresponding to chymotryptic peptide, XDHVKLVNEVTEF, where X is isoleucine of leucine (total area under the peaks "MA"=20029397). Calculations were done as follows: percent E37DMNB-C=224582204/(224582204+20029397)*100=91.8% and percent E37L=20029397/(224582204+20029397)*100=8.2%. Ion species corresponding to the incorporation of other natural amino acids at X were not detected in appreciable amounts.

REFERENCES

1. Wang, L., Xie, J. & Schultz, P. G. Expanding the genetic code. Annu Rev Biophys Biomol Struct 35, 225-249 (2006).
2. Chin, J. W. et al. An expanded eukaryotic genetic code. Science 301, 964-967 (2003).
3. Xie, J. & Schultz, P. G. A chemical toolkit for proteins—an expanded genetic code. Nat Rev Mol Cell Biol 7, 775-782 (2006).
4. Liu, W., Brock, A., Chen, S. & Schultz, P. G. Genetic incorporation of unnatural amino acids into proteins in mammalian cells. Nat Methods 4, 239-244 (2007).
5. Wang, L. & Schultz, P. G. A general approach for the generation of orthogonal tRNAs. Chem. Biol 8, 883-890 (2001).
6. Chin, J. W., Cropp, T. A., Chu, S., Meggers, E. & Schultz, P. G. Progress toward an expanded eukaryotic genetic code. Chem Biol 10, 511-519 (2003).
7. Cereghino, J. L. & Cregg, J. M. Heterologous protein expression in the methylotrophic yeast Pichia pastoris. FEMS Microbiol Rev 24, 45-66 (2000).
8. Shekhar, C. Pichia power: India's biotech industry puts unconventional yeast to work. Chem Biol 15, 201-202 (2008).
9. Clare, J. J., Rayment, F. B., Ballantine, S. P., Sreekrishna, K. & Romanos, M. A. High-level expression of tetanus toxin fragment C in Pichia pastoris strains containing multiple tandem integrations of the gene. Biotechnology (N Y) 9, 455-460 (1991).
10. Ohya, T., Ohyama, M. & Kobayashi, K. Optimization of human serum albumin production in methylotrophic yeast Pichia pastoris by repeated fed-batch fermentation. Biotechnol Bioeng 90, 876-887 (2005).

11. Sreekrishna, K. et al. High-level expression, purification, and characterization of recombinant human tumor necrosis factor synthesized in the methylotrophic yeast *Pichia pastoris*. *Biochemistry* 28, 4117-4125 (1989).
12. Cos, O., Ramon, R., Montesinos, J. L. & Valero, F. Operational strategies, monitoring and control of heterologous protein production in the methylotrophic yeast *Pichia pastoris* under different promoters: a review. *Microb Cell Fact* 5, 17 (2006).
13. Cregg, J. M., Vedvick, T. S. & Raschke, W. C. Recent advances in the expression of foreign genes in *Pichia pastoris*. *Biotechnology* (N Y) 11, 905-910 (1993).
14. Li, H. et al. Optimization of humanized IgGs in glycoengineered *Pichia pastoris*. *Nat Biotechnol* 24, 210-215 (2006).
15. Higgins, D. R. & Cregg, J. M. Introduction to *Pichia pastoris*. *Methods Mol Biol* 103, 1-15 (1998).
16. Invitrogen Life, T., Vol. K1750-01, Edn. F 85 (Invitrogen Life Technologies, Carlsbad, Calif. 92008; 2005).
17. Kim, J. G. et al. Development and characterization of a glucagon-like peptide 1-albumin conjugate: the ability to activate the glucagon-like peptide 1 receptor in vivo. *Diabetes* 52, 751-759 (2003).
18. Huang, Y. S. et al. Preparation and characterization of a novel exendin-4 human serum albumin fusion protein expressed in *Pichia pastoris*. *J Pept Sci* 14, 588-595 (2008).
19. Chuang, V. T., Kragh-Hansen, U. & Otagiri, M. Pharmaceutical strategies utilizing recombinant human serum albumin. *Pharm Res* 19, 569-577 (2002).
20. Kobayashi, K. Summary of recombinant human serum albumin development. *Biologicals* 34, 55-59 (2006).
21. Buckholz, R. G. & Gleeson, M. A. Yeast systems for the commercial production of heterologous proteins. *Biotechnology* (N Y) 9, 1067-1072 (1991).
22. Kupcsulik, B. & Sevella, B. Optimization of specific product formation rate by statistical and formal kinetic model descriptions of an HSA producing *Pichia pastoris* Mut(S) strain. *Chem Biochem Eng Q* 19, 99-108 (2005).
23. Chen, S., Schultz, P. G. & Brock, A. An improved system for the generation and analysis of mutant proteins containing unnatural amino acids in *Saccharomyces cerevisiae*. *J Mol Biol* 371, 112-122 (2007).
24. Zhang, Z. et al. A new strategy for the site-specific modification of proteins in vivo. *Biochemistry* 42, 6735-6746 (2003).
25. Kozak, M. Downstream secondary structure facilitates recognition of initiator codons by eukaryotic ribosomes. *Proc Nall Acad Sci USA* 87, 8301-8305 (1990).
26. Sears, I. B., O'Connor, J., Rossanese, O. W. & Glick, B. S. A versatile set of vectors for constitutive and regulated gene expression in *Pichia pastoris*. *Yeast* 14, 783-790 (1998).
27. Segev, N., Mulholland, J. & Botstein, D. The yeast GTP-binding YPT1 protein and a mammalian counterpart are associated with the secretion machinery. *Cell* 52, 915-924 (1988).
28. Waterham, H. R., Digan, M. E., Koutz, P. J., Lair, S. V. & Cregg, J. M. Isolation of the *Pichia pastoris* glyceraldehyde-3-phosphate dehydrogenase gene and regulation and use of its promoter. *Gene* 186, 37-44 (1997).
29. Ohi, H., Miura, M., Hiramatsu, R. & Ohmura, T. The positive and negative cis-acting elements for methanol regulation in the *Pichia pastoris* AOX2 gene. *Mol Gen Genet* 243, 489-499 (1994).
30. Hoekstra, R. et al. Phase I safety, pharmacokinetic, and pharmacodynamic study of the thrombospondin-1-mimetic angiogenesis inhibitor ABT-510 in patients with advanced cancer. *J Clin Oncol* 23, 5188-5197 (2005).
31. Yang, Q. et al. Thrombospondin-1 peptide ABT-510 combined with valproic acid is an effective antiangiogenesis strategy in neuroblastoma. *Cancer Res* 67, 1716-1724 (2007).
32. Reiher, F. K. et al Inhibition of tumor growth by systemic treatment with thrombospondin-1 peptide mimetics. *Int J Cancer* 98, 682-689 (2002).
33. Haviv, F. et al. Thrombospondin-1 mimetic peptide inhibitors of angiogenesis and tumor growth: design, synthesis, and optimization of pharmacokinetics and biological activities. *J Med Chem* 48, 2838-2846 (2005).
34. Dirksen, A., Hackeng, T. M. & Dawson, P. E. Nucleophilic catalysis of oxime ligation. *Angew Chem Int Ed Engl* 45, 7581-7584 (2006).
35. Dirksen, A., Dirksen, S., Hackeng, T. M. & Dawson, P. E. Nucleophilic catalysis of hydrazone formation and transimination: implications for dynamic covalent chemistry. *J Am Chem Soc* 128, 15602-15603 (2006).
36. Deiters, A. et al. Adding amino acids with novel reactivity to the genetic code of *Saccharomyces cerevisiae*. *J Am Chem Soc* 125, 11782-11783 (2003).
37. Lemke, E. A., Summerer, D., Geierstanger, B. H., Brittain, S. M. & Schultz, P. G. Control of protein phosphorylation with a genetically encoded photocaged amino acid. *Nat Chem Biol* 3, 769-772 (2007).
38. Summerer, D. et al. A genetically encoded fluorescent amino acid. *Proc Natl Acad Sci USA* 103, 9785-9789 (2006).
39. Wang, Q. & Wang, L. New methods enabling efficient incorporation of unnatural amino acids in yeast. *J Am Chem Soc* 130, 6066-6067 (2008).
40. Zheng, L., Baumann, U. & Reymond, J. L. An efficient one-step site-directed and site-saturation mutagenesis protocol. *Nucleic Acids Res* 32, e115 (2004).
41. Matthiesen, R., Bauw, G. & Welinder, K. G. Use of performic acid oxidation to expand the mass distribution of tryptic peptides. *Analytical chemistry* 76, 6848-6852 (2004).
42. Licklider, L. J., Thoreen, C. C., Peng, J. & Gygi, S. P. Automation of nanoscale microcapillary liquid chromatography-tandem mass spectrometry with a vented column. *Analytical chemistry* 74, 3076-3083 (2002).
43. Burnette, W. N. "Western blotting": electrophoretic transfer of proteins from sodium dodecyl sulfate—polyacrylamide gels to unmodified nitrocellulose and radiographic detection with antibody and radioiodinated protein A. *Anal Biochem* 112, 195-203 (1981).
44. Roepstorff, P. & Fohlman, J. Proposal for a common nomenclature for sequence ions in mass spectra of peptides. *Biomed Mass Spectrom* 11, 601 (1984).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An antibody conjugate comprising:
   an antibody or antibody fragment comprising a first unnatural amino acid residue; and,
   a therapeutic molecule comprising a second unnatural amino acid residue;
   wherein the antibody or antibody fragment and the therapeutic molecule are conjugated together through the first and second unnatural amino acid residues;
   wherein the first unnatural amino acid residue is incorporated into the antibody or antibody fragment and/or the second unnatural amino acid residue is incorporated into the therapeutic molecule in vivo in a methylotrophic yeast cell during translation using an orthogonal tRNA synthetase/tRNA (O-RS/O-tRNA) pair, and wherein the first unnatural amino acid residue is a p-acetylphenylalanine and the second unnatural amino acid residue is a ϵ-(2-(aminooxy)acetyl)-L-lysine or wherein the first unnatural amino acid residue is a ϵ-(2-(aminooxy)acetyl)-L-lysine and the second unnatural amino acid residue is a p-acetylphenylalanine.

2. The antibody conjugate of claim 1, wherein the first and second unnatural amino acids are covalently coupled via a cycloaddition reaction.

3. The antibody conjugate of claim 2, wherein the cycloaddition reaction is a 1,3-cycloaddition reaction.

4. The antibody conjugate of claim 1, wherein the antibody or antibody fragment is selected from the group consisting of humanized antibodies, Fab fragments, and single chain antibody fragments.

5. The antibody conjugate of claim 1, wherein the therapeutic molecule is a therapeutic protein or polypeptide.

6. The antibody conjugate of claim 1, wherein the therapeutic molecule comprises a cytotoxin.

7. The antibody conjugate of claim 1, wherein the therapeutic molecule comprises an ABT-510, a TSP-1, a human neutral endopeptidase (NEP), an antibody, an Fab, an Fv, an alpha-1 antitrypsin, an angiostatin, an antihemolytic factor, an apolipoprotein, an apoprotein, an atrial natriuretic factor, an atrial natriuretic polypeptide, an atrial peptide, a C-X-C chemokine, a T39765, a NAP-2, an ENA-78, a gro-a, a gro-b, a gro-c, an IP-10, a GCP-2, a NAP-4, an SDF-1, a PF4, a MIG, a calcitonin, a c-kit ligand, a cytokine, a CC chemokine, a monocyte chemoattractant protein-1, a monocyte chemoattractant protein-2, a monocyte chemoattractant protein-3, a monocyte inflammatory protein-1 alpha, a monocyte inflammatory protein-1 beta, a RANTES, an 1309, an R83915, an R91733, an HCC1, a T58847, a D31065, a T64262, a CD40, a CD40 ligand, a c-kit ligand, a collagen, a colony stimulating factor (CSF), a complement factor 5a, a complement inhibitor, a complement receptor 1, an epithelial neutrophil activating peptide-78, a GRO'.UPSILON., a MGSA, a GRO.beta., a GRO.gamma., an MIP1-.alpha., an MIP1-.beta., an MCP-1, a human epidermal growth factor (hEGF), an epithelial neutrophil activating peptide, an erythropoietin (EPO), an exfoliating toxin, a factor IX, a factor VII, a factor VIII, a factor X, a fibroblast growth factor (FGF), an FGF21, a fibrinogen, a fibronectin, a G-CSF, a GM-CSF, a human glucocerebrosidase, a gonadotropin variant, a growth factor, a growth factor receptor, a hedgehog protein, a hemoglobin, a hepatocyte growth factor (HGF), a Hirudin, a human serum albumin (HSA), an ICAM-1, an ICAM-1 receptor, an LFA-1, an LFA-1 receptor, a human insulin, a human insulin-like growth factor (hIGF), an hIGF-I, an hIGF-II, a human interferon, an IFN-.alpha., an IFN-.beta., an IFN-.gamma., an interleukin, an IL-1, an IL-2, an IL-3, an IL-4, an IL-5, an IL-6, an IL-7, an IL-8, an IL-9, an IL-10, an IL-11, an IL-12, a keratinocyte growth factor (KGF), a lactoferrin, a leukemia inhibitory factor, a luciferase, a neurturin, a neutrophil inhibitory factor (NIF), a human oncostatin M (OSM), an osteogenic protein, an oncogene product, a parathyroid hormone, a PD-ECSF, a PDGF, a peptide hormone, a human growth hormone (hGH), a pleiotropin, a protein A, a protein G, a pyrogenic exotoxin A, a pyrogenic exotoxin B, a pyrogenic exotoxin C, a relaxin, a renin, an SCF/c-kit, a soluble complement receptor I, a soluble I-CAM 1, a soluble interleukin receptor, a soluble TNF receptor, a somatomedin, a somatostatin, a somatotropin, a streptokinase, a superantigen, a staphylococcal enterotoxin, an SEA, an SEB, an SEC1, an SEC2, an SEC3, an SED, an SEE, a steroid hormone receptor, a superoxide dismutase, a toxic shock syndrome toxin, a thymosin alpha 1, a tissue plasminogen activator, a tumor growth factor (TGF), a TGF-.alpha., a TGF-.beta., a human tumor necrosis factor (hTNF), a human tumor necrosis factor alpha, a human tumor necrosis factor beta, a human tumor necrosis factor receptor (TNFR), a VLA-4 protein, a VCAM-1 protein, a human vascular endothelial growth factor (hVEGEF), hVEGF165, a Urokinase, a Mos, a Ras, a Raf, a Met, a p53, a Tat, a Fos, a Myc, a Jun, a Myb, a Rel, an estrogen receptor, a progesterone receptor, a testosterone receptor, an aldosterone receptor, an LDL receptor, an inflammatory molecule, a signal transduction molecule, a transcriptional activator, a transcriptional suppressor, a hyalurin, a CD44, a corticosterone, a human thyroid peroxidase (hTPO), a tetanus toxin fragment C, a bovine pancreatic trypsin inhibitor (BPTI), a human amyloid precursor protein (APP), a human antithrombin III, a BP320 antigen, a human caspase-3, a hepatitis B surface antigen, a human sex steroid-binding protein (hSBP), a human endostatin, or a gp120.

8. The antibody conjugate of claim 1, wherein the first unnatural amino acid is incorporated into the antibody or antibody fragment during translation.

9. The antibody conjugate of claim 1, wherein the second unnatural amino acid is incorporated into the therapeutic molecule during synthesis.

10. The antibody conjugate of claim 1, wherein the therapeutic molecule is a TSP-1 variant comprising the second unnatural amino acid.

11. The antibody conjugate of claim 1, wherein the therapeutic molecule is an ABT-510 variant comprising the second unnatural amino acid.

12. The antibody conjugate of claim 1, wherein the antibody or antibody fragment, or the therapeutic molecule, is produced in a *Candida* cell, a *Hansenula* cell, a *Pichia* cell, or a *Torulopsis* cell.

13. A composition comprising the antibody conjugate of claim 1.

14. A cell comprising the antibody conjugate of claim 1.

* * * * *